United States Patent
Stanek et al.

(10) Patent No.: US 10,760,079 B2
(45) Date of Patent: Sep. 1, 2020

(54) VARIANT RNAI

(71) Applicant: Genzyme Corporation, Cambridge, MA (US)

(72) Inventors: Lisa M. Stanek, Natick, MA (US); Adam Palermo, Boston, MA (US); Brenda Richards, Hopkinton, MA (US); Sergio Pablo Sardi, Newton, MA (US); Catherine O'Riordan, Bridgewater, NJ (US); Antonius Song, Dublin, CA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 16/566,565

(22) Filed: Sep. 10, 2019

(65) Prior Publication Data

US 2020/0109401 A1  Apr. 9, 2020

Related U.S. Application Data

(62) Division of application No. 15/549,895, filed as application No. PCT/US2016/017207 on Feb. 9, 2016, now Pat. No. 10,450,563.

(60) Provisional application No. 62/114,578, filed on Feb. 10, 2015.

(51) Int. Cl.
*C07H 21/04* (2006.01)
*C12N 15/113* (2010.01)

(52) U.S. Cl.
CPC ........ *C12N 15/113* (2013.01); *C12N 2310/14* (2013.01); *C12N 2310/531* (2013.01); *C12N 2310/533* (2013.01)

(58) Field of Classification Search
None
See application file for complete search history.

(56) References Cited

U.S. PATENT DOCUMENTS

| | | | |
|---|---|---|---|
| 6,566,118 B1 | 5/2003 | Atkinson et al. |
| 6,596,535 B1 | 7/2003 | Carter |
| 6,723,551 B2 | 4/2004 | Kotin et al. |
| 6,989,264 B2 | 1/2006 | Atkinson et al. |
| 6,995,006 B2 | 2/2006 | Atkinson et al. |
| 7,125,717 B2 | 10/2006 | Carter |
| 7,465,583 B2 | 12/2008 | Samulski et al. |
| 7,785,888 B2 | 8/2010 | Carter |
| 7,790,154 B2 | 9/2010 | Samulski et al. |
| 7,846,729 B2 | 12/2010 | Carter |
| 8,093,054 B2 | 1/2012 | Carter |
| 8,283,151 B2 | 10/2012 | Schmidt et al. |
| 8,361,457 B2 | 1/2013 | Samulski et al. |
| 2009/0130751 A1 | 5/2009 | Davidson et al. |
| 2012/0066783 A1 | 3/2012 | Kay et al. |
| 2012/0164106 A1 | 6/2012 | Schaffer et al. |
| 2013/0323226 A1 | 12/2013 | Wilson et al. |
| 2014/0163214 A1 | 6/2014 | Davidson et al. |
| 2014/0335054 A1 | 11/2014 | Gao et al. |
| 2015/0099793 A1 | 4/2015 | Wang |
| 2018/0023082 A1 | 1/2018 | Stanek et al. |

FOREIGN PATENT DOCUMENTS

| | | |
|---|---|---|
| JP | WO2004101787 A1 | 7/2006 |
| JP | 2010500025 A | 1/2010 |
| JP | 2011517339 A | 6/2011 |
| WO | WO-1998/010088 A1 | 3/1998 |
| WO | WO-2003/042397 A2 | 5/2003 |
| WO | WO-2003/042397 A3 | 5/2003 |
| WO | WO-2004/029212 A2 | 4/2004 |
| WO | WO2008021136 A2 | 2/2008 |
| WO | WO2008021136 A3 | 7/2008 |
| WO | WO-2008/150897 A2 | 12/2008 |
| WO | WO-2009/100502 A1 | 8/2009 |
| WO | WO2009098196 A2 | 8/2009 |
| WO | WO2009098196 A3 | 11/2009 |
| WO | WO-2011/034811 A1 | 3/2011 |

OTHER PUBLICATIONS

Ahi, Y. et al. (Aug. 2011). "Adenoviral Vector Immunity: Its Implications and Circumvention Strategies," Curr. Gene Ther. 11(4):307-320.
Alba, R. et al. (Oct. 2005). "Gutless Adenovirus: Last-Generation Adenovirus for Gene Therapy," Gene Ther. 12(Suppl 1):S18-27.
Ambros, V. (Sep. 16, 2004). "The Functions of Animal MicroRNAs," Nature 431(7006):350-355.
Andersen, J.K. et al. (1993). "Herpesvirus-Mediated Gene Delivery into the Rat Brain: Specificity and Efficiency of the Neuron-Specific Enolase Promoter," Cell. Mol. Neurobiol. 13:503-515.
Arrasate, M. et al. (2004). "Inclusion Body Formation Reduces Levels of Mutant Huntingtin and the Risk of Neuronal Death," Nature 431(7010):805-810.
Augood, S.J. et al. (Aug. 1997). "Dopamine D1 and D2 Receptor Gene Expression in the Striatum in Huntington's Disease", Ann. Neural. 42(2):215-221.

(Continued)

*Primary Examiner* — Kimberly Chong
(74) *Attorney, Agent, or Firm* — Morrison & Foerster LLP

(57) ABSTRACT

Provided herein are RNAi molecules including a first strand containing a guide sequence and a second strand comprising a non-guide sequence where the non-guide sequence contains a bulge opposite the seed region of the guide sequences; e.g., opposite the cleavage sequence. In some aspects, the invention provides RNAi for treating Huntington's disease. Further provided herein are expression cassettes, vectors (e.g., rAAV, recombinant adenoviral, recombinant lentiviral, and recombinant HSV vectors), cells, viral particles, and pharmaceutical compositions containing the RNAi. Yet further provided herein are methods and kits related to the use of the RNAi, for example, to treat Huntington's disease.

41 Claims, 16 Drawing Sheets

Specification includes a Sequence Listing.

(56) References Cited

OTHER PUBLICATIONS

Bates, G. (May 10, 2003). "Huntingtin Aggregation and Toxicity in Huntington's Disease", Lancet 361(9369):1642-1644.
Benn, C.L. et al. (2008). "Huntingtin Modulates Transcription, Occupies Gene Promoters In Vivo, and Binds Directly to DNA in a Polyglutamine-Dependent Manner," J. Neurosci. 28(42):10720-10733.
Bhide, P.G. et al. (Sep. 1, 1996). "Expression of Normal and Mutant Huntingtin in the Developing Brain," J. Neurosci. 16(17):5523-5535.
Boison, D. (Sep. 2010). "Inhibitory RNA in epilepsy: Research Tool and Therapeutic Perspectives," Epilepsia 51(9):1659-1668.
Boshart, M. et al. (Jun. 1985). "A Very Strong Enhancer is Located Upstream of an Immediate Early Gene of Human Cytomegalovirus," Cell 41(2):521-530.
Bossis, I. et al. (Jun. 2003). "Cloning of an Avian Adeno-Associated Virus (AAAV) and Generation of Recombinant AAAV Particles," J. Virol. 77(12):6799-6810.
Boudreau R.L. et al. (Aug. 31, 2012). "siSPOTR: a Tool for Designing Highly Specific and Potent siRNAs for Human and Mouse," Nucleic Acids Res. 41(1):e9, 12 pages.
Boudreau, R.L. et al. (Jan. 2013, e-pub. Aug. 31, 2012). "siSPOTR: A Tool for Designing Highly Specific and Potent Sirnas for Human and Mouse," Nucleic Acids Res. 41(1):e9, 12 pages.
Boudreau, R.L. et al. (Jun. 2009, e-pub. Feb. 24, 2009). "Nonallele-Specific Silencing of Mutant and Wild-Type Huntingtin Demonstrates Therapeutic Efficacy in Huntington's Disease Mice", Mol. Ther. 17(6):1053-1063.
Castanotto, D. et al. (Jan. 22, 2009). "The Promises and Pitfalls of RNA-Interference-Based Therapeutics," Nature 457(7228):426-433.
Cattaneo, E. et al. (Dec. 2005). "Normal Huntingtin Function: An Alternative Approach to Huntington's Disease," Nat. Rev. Neurosci. 6(12):919-930.
Cha, J.H. (Sep. 2000). "Transcriptional Dysregulation in Huntington's Disease," Trends Neurosci. 23(9):387-392.
Chiu Y-L et al: "RNAi in Human Cells: Basic Structural and Functional Features of Small Interfering RNA", Molecular Cell, Cell Press, Cambridge, MA, US,vol. 10, Sep. 1, 2002 (Sep. 1, 2002), pp. 549-561.
Clark, K.R. et al. (Apr. 10, 1999). "Highly Purified Recombinant Adeno-Associated Virus Vectors are Biologically Active and Free of Detectable Helper and Wild-Type Viruses," Hum. Gene Ther. 10(6):1031-1039.
Clark, P. R. et al: "Knockdown of TNFR1 by,the sense strand of an ICAM-1 siRNA: dissection of an off-target effect", Nucleic Acids Research,vol. 36, No. 4, Jan. 1, 2007 (Jan. 1, 2007), pp. 1081-1097.
Conway, J.E. et al. (Nov. 1997). "Recombinant Adeno-Associated Virus Type 2 Replication and Packaging is Entirely Supported by a Herpes Simplex Virus Type 1 Amplicon Expressing Rep and Cap," J. Virology 71(11):8780-8789.
Cronin, J. et al. (Aug. 2005). "Altering the Tropism of Lentiviral Vectors Through Pseudotyping," Curr. Gene Ther. 5(4):387-398.
Cryan, J.F. et al. (Feb. 2, 2002). "Noradrenergic Lesions Differentially Alter the Antidepressant-Like Effects of Reboxetine in a Modified Forced Swim Test," Eur. J. Pharmacol. 436(2002):197-205.
Cryan, J.F. et al. (May 2002) "Assessing Antidepressant Activity in Rodents: Recent Developments and Future Needs," Trends Pharmacol. Sci. 23(5):238-245.
Danthinne, X et al. (2000). "Production of First Generation Adenovirus Vectors: A Review," Viral Transfer Technology 7:1707-1714.
Davidson, B.L. et al. (Aug. 31, 2012). "Singles Engage the RNA Interference Pathway", Cell 150:873-875.
Davidson, B.L. et al. (Mar. 28, 2000). "Recombinant Adeno-Associated Virus Type 2, 4, and 5 Vectors: Transduction of Variant Cell Types and Regions in the Mammalian Central Nervous System," PNAS 97(7):3428-3432.

Desplats, P.A. et al. (2006). "Selective deficits in the expression of striatal-enriched mRNAs in Huntington's disease", J. Neurochem. 96:743-757.
Difiglia, M. et al. (Oct. 23, 2007). "Therapeutic Silencing of Mutant Huntingtin with siRNA Attenuates Striatal and Cortical Neuropathology and Behavioral Deficits," Proc. Natl. Acad. Sci. USA 104(43):17204-17209.
Difiglia, M. et al. (Sep. 26, 1997). "Aggregation of Huntingtin in Neuronal Intranuclear Inclusions and Dystrophic Neurites in Brain," Science 277(5334):1990-1993.
Drouet, V. et al. (Mar. 2009). "Sustained Effects of Nonallele-Specific Huntingtin Silencing", Ann. Neurol. 65(3):276-285.
Dull, T. et al. (Nov. 1998) "A Third-Generation Lentivirus Vector with a Conditional Packaging System," J. Viral. 72:8463-8471.
Durand, S. et al. (2011). "The Inside Out of Lentiviral Vectors," Viruses 3:132-59.
Fisher, K.J. et al. (Jan. 1996). "Transduction with Recombinant Adeno-Associated Virus for Gene Therapy Is Limited by Leading-Strand Synthesis" J. Virol. 70:520-532.
Fukuda, A.M. et al. (Sep. 5, 2013). "siRNA Treatment: "A Sword-in-the-Stone" for Acute Brain Injuries," Genes 4:435-456.
Gantier, M. et al. (Apr. 1, 2020). "Rational Design of Immunostimulatory siRNAs," Mol Ther. 18(4):785-795.
Gao, G. et al. (Jun. 2004). "Clades of Adeno-Associated Viruses are Widely Disseminated in Human Tissues," J. Virol. 78(12):6381-6388.
Gao, G. et al. (May 13, 2003). "Adeno-Associated Viruses Undergo Substantial Evolution in Primates During Natural Infections," PNAS 100(10):6081-6086.
Gao, G. et al. (Sep. 3, 2002). "Novel Adeno-Associated Viruses from Rhesus Monkeys as Vectors for Human Gene Therapy," PNAS 99(18):11854-11856.
GenBank Gene ID 396526.
Goins, W.F. et al. (2014). "Engineering HSV-1 Vectors for Gene Therapy" Chapter 5 in Herpes Simplex Virus: Methods and Protocols, Methods in Molecular Biology, vol. 1144, Diefenbach, R.J. et al. eds., Springer Science+Business Media, New York, pp. 63-79.
Gossen, M. et al. (Jun. 15, 1992). "Tight control of gene expression in mammalian cells by tetracycline-responsive promoters," Proc. Natl. Acad. Sci. USA 89(12):5547-5551.
Gossen, M. et al. (Jun. 23, 1995). "Transcriptional Activation by Tetracyclines in Mammalian Cells," Science 268:1766-1769.
Grondin, R. et al. (Apr. 2012, e-pub. Jan. 16, 20012). "Six-Month Partial Suppression of Huntingtin is Well Tolerated in the Adult Rhesus Striatum," Brain 135(4):1197-1209.
Gu, S. et al. (Nov. 9, 2012). "The Loop Position of shRNAs and Pre-miRNAs Is Critical for the Accuracy of Dicer Processing In Vivo", Cell 151(4):900-911.
Guo Z.S. et al. (Sep. 1996). "Evaluation of Promoter Strength for Hepatic Gene Expression in Vivo Following Adenovirus-Mediated Gene Transfer," Gene Ther. 3(9):802-810.
Gutekunst, C.A. et al. (Apr. 1, 1999). "Nuclear and Neuropil Aggregates in Huntington's Disease: Relationship to Neuropathology," J. Neurosci. 19(7):2522-2534.
Harper, S.Q. et al. (Apr. 19, 2005). "RNA Interference Improves Motor and Neuropathological Abnormalities in a Huntington's Disease Mouse Model," Proc. Natl. Acad. Sci. USA 102(16):5820-5825.
Harvey, D.M. et al. (1998). "Inducible Control of Gene Expression: Prospects for Gene Therapy," Curr. Opin. Chem. Biol. 2:512-518.
Huntington Study Group. (1996). "Unified Huntington's Disease Rating Scale: Reliability and Consistency," Movement Disorders 11:136-142.
International Search Report dated Aug. 8, 2016, for PCT Application No. PCT/US2016/017207, filed on Feb. 9, 2016, 9 pages.
Jackson, A.L. et al. (Jan. 2010). "Recognizing and Avoiding siRNA Off-Target Effects for Target Identification and Therapeutic Application," Nature Rev. Drug Disc. 9(1):57-67.
Kay, M. et al. (Jan. 2001). "Viral Vectors for Gene Therapy: The Art of Turning Infectious Agents into Vehicles of Therapeutics," Nat. Med. 7(1):33-40.

(56) References Cited

OTHER PUBLICATIONS

Kim, D.W. et al. (1990). "Use of the Human Elongation Factor 1α Promoter as a Versatile and Efficient Expression System," Gene 91(2):217-223.
Kordasiewicz, H.B. et al. (Jun. 21, 2012). "Sustained Therapeutic Reversal of Huntington's Disease by Transient Repression of Huntingtin Synthesis," Neuron 74(6):1031-1044.
Kotin, R.M. (1994). "Prospects for the Use of Adeno-Associated Virus as a Vector for Human Gene Therapy," Hum. Gene Ther. 5:793-801.
Krol, J. et al. (Sep. 2010, e-pub. Jul. 7, 2010). "The Widespread Regulation of MicroRNA Biogenesis, Function and Decay," Nat. Rev. Genet. 11:597-610.
Lagos-Quintana, M. et al. (Apr. 30, 2002). "Identification of tissue-specific MicroRNAs from Mouse," Curr. Biol. 12:735-739.
Lansbury, P.T. et al. (Oct. 19, 2006). "A Century-Old Debate on Protein Aggregation and Neurodegeneration Enters the Clinic," Nature 443:774-779.
Machida, Y. et al. (Apr. 28, 2006, e-pub. Mar. 3, 2006). "rAAV-mediated shRNA Ameliorated Neuropathology in Huntington Disease Model Mouse," Biochem. Biophys. Res. Commun. 343(1):190-197.
Magari, S.R. et al. (1997). "Pharmacologic Control of a Humanized Gene Therapy System Implanted into Nude Mice," J. Clin. Invest. 100:2865-2872.
Manservigi, R. et al. (2010). "HSV Recombinant Vectors for Gene Therapy," Open Virol. J. 4:123-156.
Martin, J. et al. (Aug. 2013). "Generation and Characterization of Adeno-Associated Virus Producer Cell Lines for Research and Preclinical Vector Production," Human Gene Therapy Methods 24:253-269.
Matsui, M. et al. (May 2012). "Allele-selective inhibition of trinucleotide repeat genes," Drug Discov. Today 17(9-10):443-450.
McBride, J.L. et al. (Apr. 15, 2008). "Artificial miRNAs mitigate shRNA-mediated toxicity in the brain: Implications for the therapeutic development of RNAi," Proc. Natl. Acad. Sci. USA 105(15):5868-5873.
McBride, J.L. et al. (Dec. 2011). "Preclinical Safety of RNAi-Mediated HTT Suppression in the Rhesus Macaque as a Potential Therapy for Huntington's Disease," Mol. Ther. 19(12):2152-2162.
McLaughlin, S.K. et al. (Jun. 1988). "Adeno-Associated Virus General Transduction Vectors: Analysis of Proviral Structures," J. Virol. 62(6):1963-1973.
Meignier, B. et al. (May 1987). "Immunization of Experimental Animals with Reconstituted Glycoprotein Mixtures of Herpes Simplex Virus 1 and 2: Protection Against Challenge with Virulent Virus," J. Infect. Dis. 155(5):921-930.
Mittoux, V. et al. (Jun. 1, 2002). "Corticostriatopallidal Neuroprotection by Adenovirus-Mediated Ciliary Neurotrophic Factor Gene Transfer in a Rat Model of Progressive Striatal Degeneration", J. Neurosci. 22:4478-4486.
Miyagishi, M. et al. (Jul. 2004). "Optimization of an siRNA-expression systems with an improved hairpin and its significant suppressive effects in mammalian cells", Journal of Gene Medicine 6:715-723.
Miyazaki, J. et al. (1989). "Expression Vector System Based on the Chicken β-actin Promoter Directs Efficient Production of Interleukin-5," Gene 79(2):269-77.
Niwa, H. et al. (1991). "Efficient Selection for High-Expression Transfectants with a Novel Eukaryotic Vector," Gene 108(2):193-199.
No, D. et al. (Apr. 1996). "Ecdysone-Inducible Gene Expression in Mammalian Cells and Transgenic Mice," Proc. Natl. Acad. Sci. USA 93:3346-3351.
Passini, M.A. et al. (Dec. 2001). "Widespread Gene Delivery and Structure-Specific Patterns of Expression in the Brain after Intraventricular Injections of Neonatal Mice with an Adeno-Associated Virus Vector," J. Viral. 75(24):12382-12392.
Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," J. Virol. 77(12):7034-7040.
Pechan, P. et al. (2009, e-pub. Jul. 17, 2008). "Novel anti-VEGF Chimeric Molecules Delivered by AAV Vectors for Inhibition of Retinal Neovascularization," Gene Ther. 16:10-16.
Piccioli, P. et al. (1991). "Neuroantibodies: Molecular Cloning of a Monoclonal Antibody Against Substance P For Expression in the Central Nervous System," Proc. Natl. Acad. Sci. IDSA 88:5611-5615.
Piccioli, P. et al. (Aug. 1995). "Neuroantibodies: Ectopic Expression of a Recombinant Anti-Substance P Antibody in the Central Nervous System of Transgenic Mice," Neuron 15:373-384.
Porsolt, R.D. et al. (Oct. 1977). "Behavioral Despair in Mice: A Primary Screening test for Antidepressants," Arch. Int. Pharmacodyn. Ther. 229(2):327-336.
Pouladi, M.A. et al. (2009). "Prevention of Depressive Behaviour in the YAC128 Mouse Model of Huntington Disease by Mutation at Residue 586 of Huntingtin," Brain 132:919-932.
Pouladi, M.A. et al. (2012, e-pub. Feb. 9, 2012). "Marked Differences in Neurochemistry and Aggregates Despite Similar Behavioural and Neuropathological Features of Huntington Disease in the Full-Length BACHD and YAC128 Mice," Hum. Mol. Genet. 21(10):2219-2232.
Ramaswamy, S. et al. (2007) "Animal Models of Huntington's Disease", ILAR J. 48(4):356-373.
Reiner, A. et al. (Dec. 2003). "Wild-Type Huntingtin Plays a Role in Brain Development and Neuronal Survival", Mol. Neurobiol. 28(3):259-276.
Richfield, E.K. et al. (Mar. 1995). "Reduced expression of Preproenkephalin in Striatal Neurons from Huntington's Disease Patients", Ann. Neural. 37:335-343.
Rodriguez-Lebron, E. et al. (Oct. 2005). "Intrastriatal rAAV-Mediated Delivery of Anti-huntingtin shRNAs Induces Partial Reversal of Disease Progression in R6/1 Huntington's Disease Transgenic Mice", Mol. Ther. 12(4):618-633.
Rosas, H.D. et al. (2002). "Regional and Progressive Thinning of the Cortical Ribbon in Huntington's Disease", Neurology 58(5):695-701.
Sah, D.W.Y. et al. (Feb. 1, 2011). "Oligonucleotide Therapeutic Approaches for Huntington Disease", J. Clin. Invest. 121(2):500-507.
Samaniego, L.A. et al. (Apr. 1998). "Persistence and Expression of the Herpes Simplex Virus Genome in the Absence of Immediate-Early Proteins", J. Virol. 72(4):3307-3320.
Saudou, F. et al. (Oct. 2, 1998). "Huntingtin Acts in the Nucleus to Induce Apoptosis but Death Does Not Correlate with the Formation of Intranuclear Inclusions", Cell 95(1):55-66.
Schaffar, G. et al. (Jul. 2, 2004). "Cellular Toxicity of Polyglutamine Expansion Proteins: Mechanism of Transcription Factor Deactivation", Mol. Cell. 15(1):95-105.
Scherzinger, E. et al. (Aug. 8, 1997). "Huntingtin-Encoded Polyglutamine Expansions form Amyloid-Like Protein Aggregates in vitro and in vivo", Cell 90(3):549-558.
Segura, M.M. et al. (Jul. 2013, e-pub Apr. 16, 2013). "New Developments in Lentiviral Vector Design, Production and Purification", Expert Opin Biol Ther. 13(7):987-1011.
Slow, E.J. et al. (Jul. 1, 2003). "Selective Striatal Neuronal Loss in a YAC128 Mouse Model of Huntington Disease", Hum. Mol. Genet. 12(13):1555-1567.
Stanek, L. et al. (May 2014). "Silencing Mutant Huntingtin by Adeno Associated Virus-Mediated RNA Interference Ameliorates Disease Manifestations in the YAC128 Mouse Model of Huntington's Disease," Hum Gene Ther. 25:461-474.
Sugars, K.L. et al. (Feb. 6, 2004, e-pub Nov. 18, 2003). "Decreased cAMP Response Element-Mediated Transcription: An Early Event in Exon 1 and Full-Length Cell Models of Huntington's Disease that Contributes to Polyglutamine Pathogenesis", J. Biol. Chem. 279(6):4988-4999.
Tatsis, N. et al. (Oct. 2004, e-pub Aug. 14, 2004). "Adenoviruses as Vaccine Vectors", Mol. Ther. 10(4):616-629.

(56) References Cited

OTHER PUBLICATIONS

Terasawa, K. et al. (2011, e-pub Jul. 12, 2011). "Synthetic Pre-miRNA-Based shRNA as Potent RNAi Triggers", Journal of Nucleic Acids 2011:131579, 6 pages.

Treleaven, C.M. et al. (Sep. 4, 2012, e-pub Jun. 26, 2012). "Gene Transfer to the CNS Is Efficacious in Immune-primed Mice Harboring Physiologically Relevant Titers of Anti-AAV Antibodies", Mol. Ther. 20(9):1713-1723.

Van Raamsdonk, J.M. et al. (2005, e-pub Nov. 2005). "Selective Degeneration and Nuclear Localization of Mutant Huntingtin in the YAC128 Mouse Model of Huntington Disease", Hum. Mal. Genet. 14(24):3823-3835.

Van Raamsdonk, J.M. et al. (Apr. 2007, e-pub Dec. 29, 2006). "Phenotypic Abnormalities in the YAC128 Mouse Model of Huntington Disease are Penetrant on Multiple Genetic Backgrounds and Modulated by Strain", Neurobiol Dis. 26(1):189-200.

Veldwijk, M.R. et al. (Aug. 2002). "Development and Optimization of a Real-Time Quantitative PCR-Based Method for the Titration of AAV-2 Vector Stocks", Mol. Ther. 6(2):272-278.

Von Hörsten, S. et al. (Mar. 15, 2003). "Transgenic Rat Model of Huntington's Disease", Hum. Mol. Genet. 12(6):617-624.

Vonsattel, J.P. et al. (Nov. 1985). "Neuropathological Classification of Huntington's Disease", J. Neuropathol. Exp. Neural. 44(6):559-577.

Wang, Y. et al. (Mar. 1997). "Ligand-Inducible and Liver-Specific Target Gene Expression in Transgenic Mice", Nat. Biotech. 15(3):239-243.

Wang, Y. et al. (May 1997). "Positive and Negative Regulation of Gene Expression in Eukaryotic Cells with an Inducible Transcriptional Regulator", Gene Ther. 4(5):432-441.

Wang, Z. et al. (Dec. 2003). "Rapid and Highly Efficient Transduction by Double-Stranded Adeno-Associated Virus Vectors In Vitro and In Vivo", Gene Ther 10(26):2105-2111.

Written Opinion of the International Searching Authority dated Aug. 8, 2016, for PCT Application No. PCT/US2016/017207, filed on Feb. 9, 2016, 11 pages.

Xiao, X. et al. (Mar. 1997). "Gene Transfer by Adeno-Associated Virus Vectors into the Central Nervous System", Exp. Neurobiol. 144(1):113-124.

Xiao, X. et al. (Mar. 1998). "Production of High-Titer Recombinant Adeno-Associated Virus Vectors in the Absence of Helper Adenovirus", J. Virol. 72(3):2224-2232.

Yamamoto, A. et al. (Mar. 21, 2000). "Reversal of Neuropathology and Motor Dysfunction in a Conditional Model of Huntington's Disease", Cell 101(1):57-66.

Yang, S.H. et al. (Jun. 12, 2008, May 18, 2000). "Towards a Transgenic Model of Huntington's Disease in a Non-Human Primate", Nature 453(7197):921-924.

Yu, D. et al. (Aug. 31, 2012). "Single-Stranded RNAs Use RNAi to Potently and Allele-Selectively Inhibit Mutant Huntingtin Expression", Cell 150(5):895-908.

Zhong, L. et al. (Jun. 3, 2008). "Next Generation of Adeno-Associated Virus 2 Vectors: Point Mutations in Tyrosines Lead to High-Efficiency Transduction at Lower Doses", Proc Natl Acad Sci USA 105(22):7827-7832.

Zuccato, C. et al. (Sep. 2003, Jul. 27, 2003). "Huntingtin Interacts with REST/NRSF to Modulate the Transcription of NRSE-Controlled Neuronal Genes", Nat. Genet. 35(1):76-83.

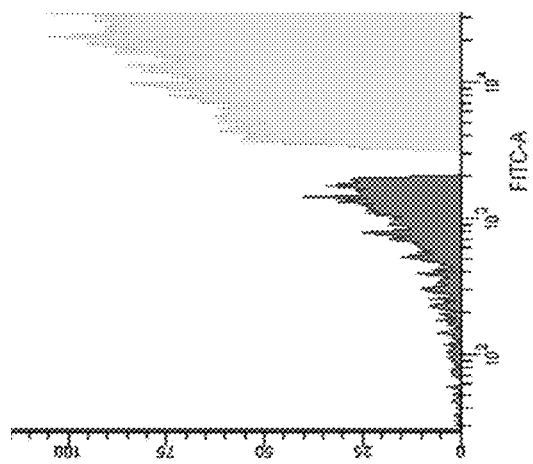
FIG. 3A  FIG. 3B  FIG. 3C
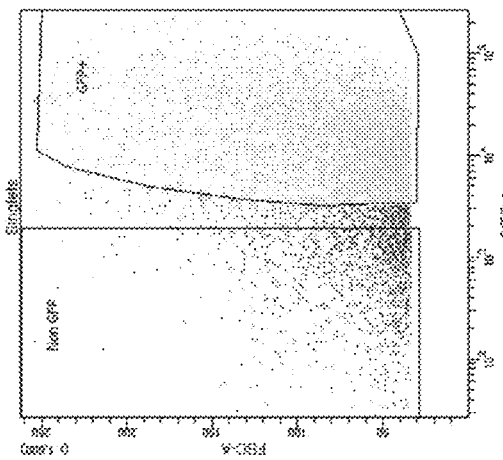
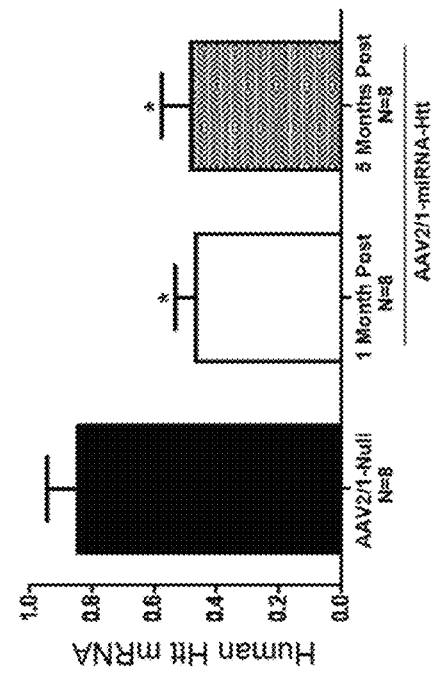
FIG. 3E
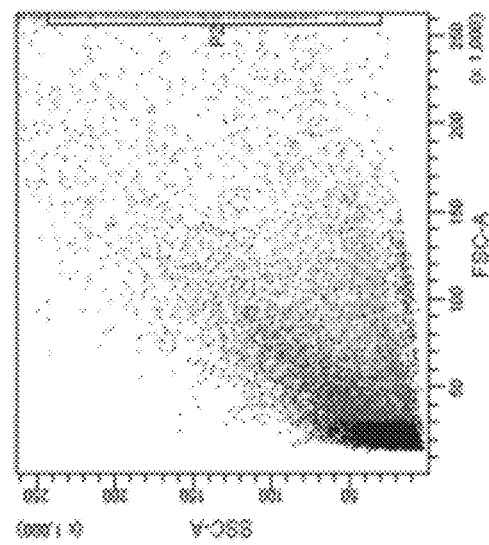
FIG. 3D
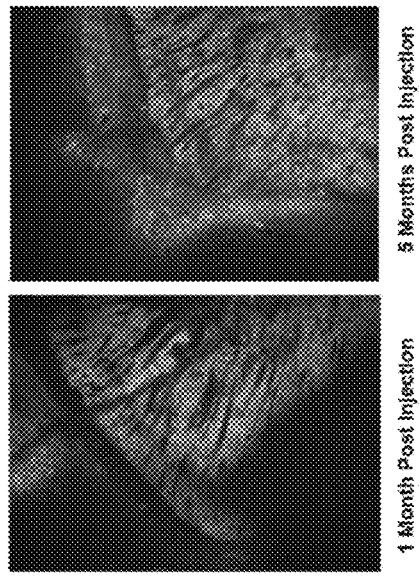

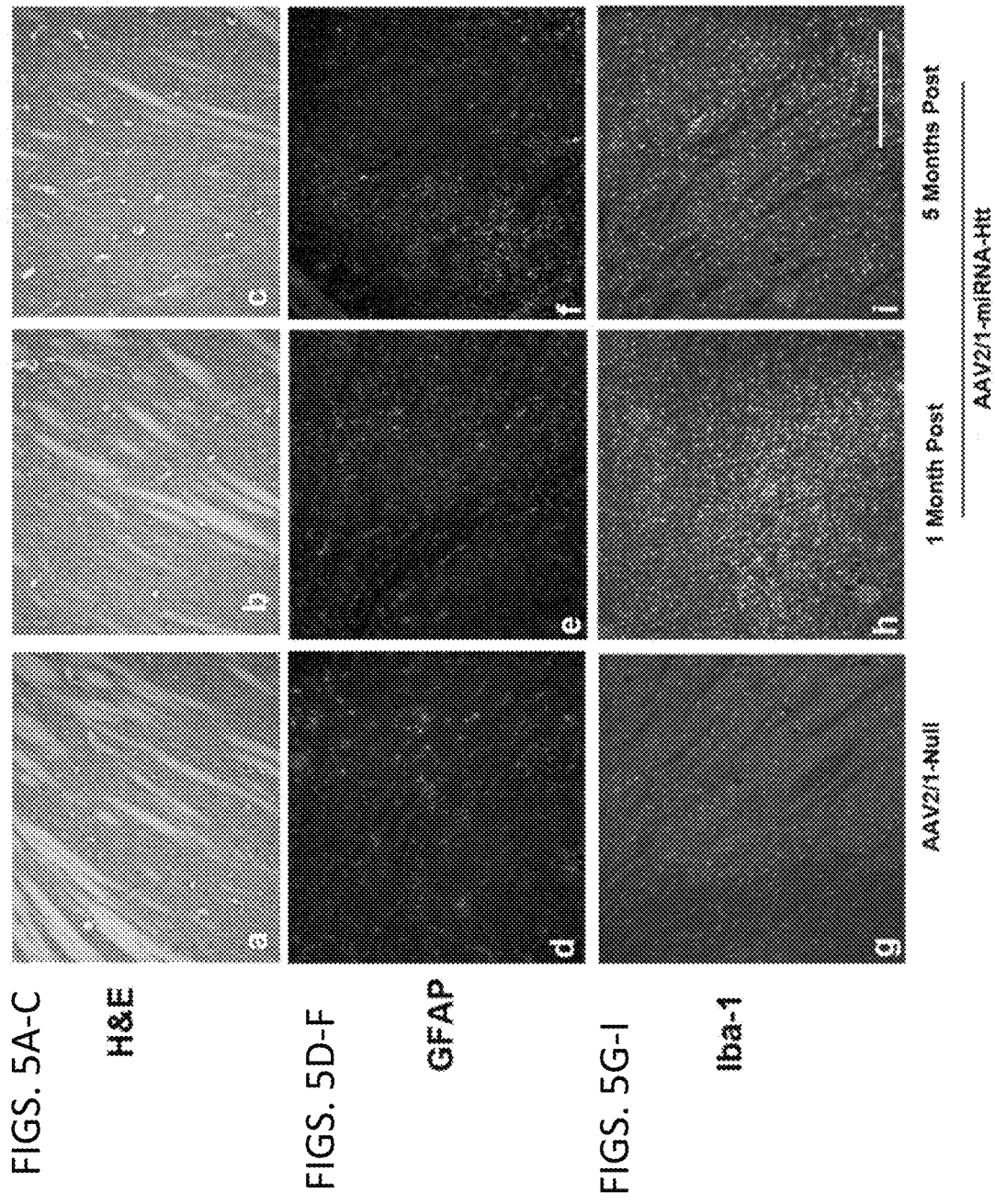

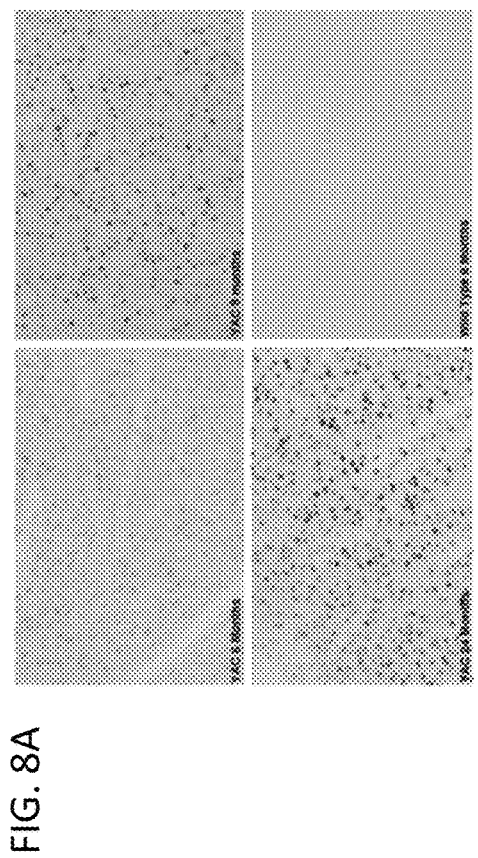
FIG. 8A
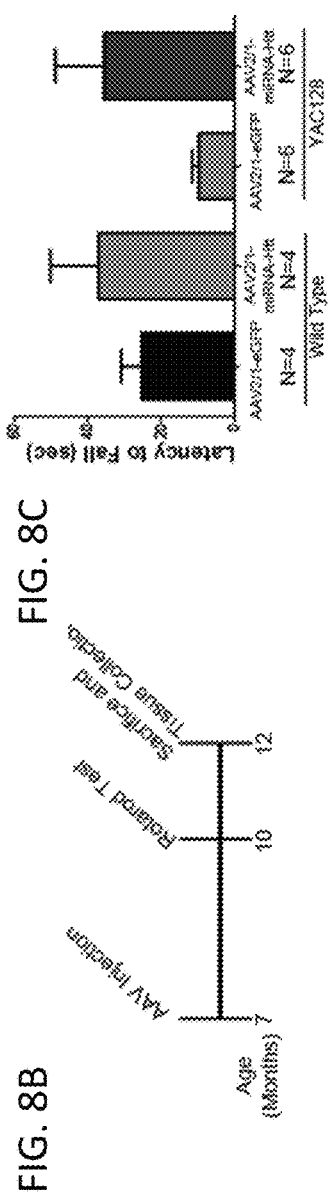
FIG. 8B
FIG. 8C
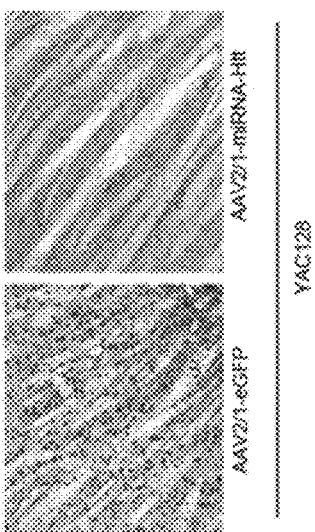
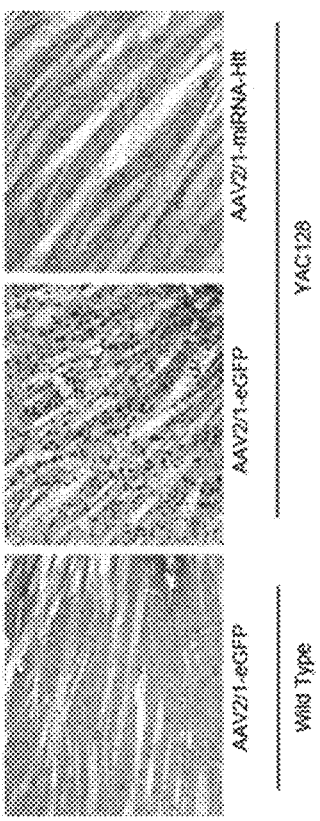
FIG. 8D

VARIANT RNAI

CROSS-REFERENCE TO RELATED APPLICATIONS

This application is a divisional of U.S. patent application Ser. No. 15/549,895, which adopts the international filing date of Feb. 9, 2016, which is a National Phase application under 35 U.S.C. § 371 of International Application No. PCT/US2016/017207, filed Feb. 9, 2016, which claims priority to U.S. Provisional Application No. 62/114,578, filed Feb. 10, 2015, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792010110SEQLIST.TXT, date recorded: Sep. 3, 2019, size: 11 KB).

FIELD OF THE INVENTION

The present invention relates to variant RNAi molecules. In some aspects, the invention relates to variant RNAi to treat Huntington's disease.

BRIEF SUMMARY OF THE INVENTION

RNA interference (RNAi) has been shown to be a useful tool for gene silencing in basic research of gene function and shows great promise as a therapeutic agent to suppress genes associated with the development of a number of diseases. In nature, gene regulation by RNAi occurs through small RNAs known as microRNAs (miRNAs) (Ambros, (2004) Nature 431:350-355; Krol et al., (2010) Nat. Rev. Genet. 11:597-610). MicroRNAs have emerged as powerful regulators of diverse cellular processes, and when delivered by viral vectors, artificial miRNAs are continually expressed, resulting in a robust and sustained suppression of target genes. The elucidation of the mechanisms involved in miRNA processing has allowed scientists to co-opt the endogenous cellular RNAi machinery and direct the degradation of a target gene product with the use of artificial miRNAs (see, e.g., US PG Pub. 2014/0163214 and Davidson et al., (2012) Cell 150:873-875).

A hurdle to the clinical development of RNAi is the potential for off-target silencing where the seed region of the RNAi (typically nucleotides 1-7 or 1-8) pairs with sequences in non-target mRNAs in the 3' untranslated region (UTR) leading to transcript destabilization. Attempts to reduce off-target silencing include the use of algorithms to identify candidate seed sequences with high specificity for the target mRNA with minimal off-target potential (Boudreau R L et al., (2012) *Nucl. Acids Res.* 41(1):e9) and placing an internal bulge in the guide region of the RNAi (Terasawa et al., (2011) *Journal of nucleic acids* 2011:131579).

RNAi has been investigated as a therapeutic to treat Huntington's disease (HD). HD is an inherited neurodegenerative disease caused by an expansion of the CAG repeat in exon 1 of the huntingtin gene (HTT). The resulting extension of the polyglutamine tract in the N-terminal region confers a toxic gain-of-function to the mutant huntingtin protein (mHtt). The potential of silencing mHtt expression as a therapeutic strategy for HD was first demonstrated in a conditional mouse model of the disease (Yamamoto et al., (2000) Cell 101:57-66.). When the expression of mHtt was induced in these mice, pathological and behavioral aberrations became apparent. Subsequent tetracycline-mediated repression of the mHtt transgene reversed these abnormalities, indicating that a reduction of mHtt levels allowed protein clearance mechanisms within neurons to normalize mHtt-induced changes. Hence, therapeutic strategies that reduce mHtt levels could potentially halt disease progression and alleviate HD symptoms.

In some aspects, the invention provides an RNAi comprising a first strand and a second strand, wherein a) the first strand and the second strand form a duplex; b) the first strand comprises a guide region of at least 19 bases, wherein the guide region comprises a seed region comprising bases 1–N of the guide strand, N=7 or N=8; and c) the second strand comprises a non-guide region of at least 11 bases (e.g., at least 19 bases) the non-guide region comprises a bulge sequence opposite of any one or more of bases 1–(N+2) of the guide region in the duplex. In some embodiments, N=7 and the bulge is opposite base 1, 2, 3, 4, 5, 6, 7, 8, or 9 of the guide region. In other embodiments, N=8 and the bulge is opposite base 1, 2, 3, 4, 5, 6, 7, 8, 9, or 10 of the guide region. In some embodiments, the bulge is opposite base 1 or base N+2 of the guide region.

In some aspects, the invention provides an RNAi comprising a first strand and a second strand, wherein a) the first strand and the second strand form a duplex; b) the first strand comprises a guide region of at least 11 bases (e.g., at least 19 bases), wherein the guide region comprises a seed region comprising bases 1–N of the guide strand, N=7 or N=8; and c) the second strand comprises a non-guide region of at least 11 bases (e.g., at least 19 bases), wherein the non-guide region comprises a bulge sequence opposite of any one or more of bases 1–(N+1) of the guide region in the duplex. In some embodiments, N=7 and the bulge is opposite base 1, 2, 3, 4, 5, 6, 7, or 8 of the guide region. In other embodiments, N=8 and the bulge is opposite base 1, 2, 3, 4, 5, 6, 7, 8, or 9 of the guide region. In some embodiments, the bulge is opposite base 1 or base N+1 of the guide region.

In some aspects, the invention provides an RNAi comprising a first strand and a second strand, wherein a) the first strand and the second strand form a duplex; b) the first strand comprises a guide region of at least 11 bases (e.g., at least 19 bases), wherein the guide region comprises a seed region comprising bases 1–N of the guide strand, N=7 or N=8; and c) the second strand comprises a non-guide region of at least 11 bases (e.g., at least 19 bases), wherein the non-guide region comprises a bulge sequence opposite of any one or more of bases 1–N of the guide region in the duplex. In some embodiments, N=7 and the bulge is opposite base 1, 2, 3, 4, 5, 6 or 7 of the guide region. In other embodiments, N=8 and the bulge is opposite base 1, 2, 3, 4, 5, 6, 7 or 8 of the guide region. In some embodiments, the bulge is opposite base 1 or base N of the guide region. In some embodiments, the bulge is opposite base 1 of the guide region.

In some embodiments of the above aspects and embodiments, the bulge is formed by one or more bases of the non-guide strand in the duplex that lack a complementary base on the guide region, wherein the bulge is flanked by bases that do basepair with the guide strand. In some embodiments, the bulge comprises 1 to 10 nucleotides. In some embodiments, the bulge comprises 1-3 nucleotides. In further embodiments, the RNAi comprises a second bulge, wherein the second bulge is located on the first strand in the guide region located 3' to the seed region.

In some embodiments of the above aspects and embodiments, the duplex is between 19 and 25 or 19 and 23 base pairs in length. In some embodiments, the first and/or second strand further comprises a 3' overhang region, a 5' overhang region, or both 3' and 5' overhang regions. In some embodiments, the first strand and the second strand are linked by means of RNA linker capable of forming a loop structure. In some embodiments, the RNA linker comprises from 4 to 50 nucleotides. In some embodiments, the loop structure comprises 4 to 20 nucleotides. In some embodiments, the RNAi comprises 5' to 3' the second strand, the RNA linker, and the first strand. In some embodiments, the RNAi comprises 5' to 3' the first strand, the RNA linker, and the second strand. In some embodiments, the RNAi is a small inhibitory RNA (siRNA), a microRNA (miRNA), or a small hairpin RNA (shRNA).

In some embodiments of the above aspects, the nucleotide sequence of the RNAi is improved to reduce off-target gene silencing (e.g., improved to reduce silencing genes wherein the seed region pairs with sequences in 3'-UTRs of unintended mRNAs and directs translational repression and destabilization of those transcripts). In some embodiments, the nucleic acid sequence comprises one or more CpG motifs. In some embodiments, the nucleic acid sequence comprises one or more CpG motifs in the seed region.

In some embodiments of the above aspects and embodiments, the RNAi targets RNA encoding a polypeptide associated with a disorder. In some embodiments, the disorder is a CNS disorder. In some embodiments, the disorder is lysosomal storage disease (LSD), Huntington's disease, epilepsy, Parkinson's disease, Alzheimer's disease, stroke, corticobasal degeneration (CBD), corticogasal ganglionic degeneration (CBGD), frontotemporal dementia (FTD), multiple system atrophy (MSA), progressive supranuclear palsy (PSP) or cancer of the brain. In some embodiments, the disorder is Huntington's Disease. In further embodiments, the polypeptide is huntingtin. In yet further embodiments, the huntingtin comprises a mutation associated with Huntington's Disease. In some embodiments, the guide region comprises the sequence 5'-UAGACAAUGAUUCA-CACGGU-3' (SEQ ID NO:1) and the non-guide region comprises the sequence 5'-ACCGUGUGUCAUUGUC-UAA-3' (SEQ ID NO:2). In some embodiments, the guide region comprises the sequence 5'-UCGACAAUGAUUCA-CACGGU-3' (SEQ ID NO:15) and the non-guide region comprises the sequence 5'-ACCGUGUGUCAUUGUC-GAA-3' (SEQ ID NO:16). In some embodiments, the guide region comprises the sequence 5'-UAGACGAUGAUUCA-CACGGU-3' (SEQ ID NO:17) and the non-guide region comprises the sequence 5'-ACCGUGUGUCAUCGUC-UAA-3' (SEQ ID NO:18).

In some embodiments, the invention provides a method to reduce the toxicity of a RNAi comprising introducing a bulge in the non-guide region of the RNAi to generate a RNAi as described herein.

In some aspects, the invention provides an expression construct comprising nucleic acid encoding the RNAi as described herein. In some embodiments, the nucleic acid encoding the RNAi comprises a miRNA scaffold. In some embodiments, the nucleic acid encoding the RNAi is operably linked to a promoter. In some embodiments, the promoter is selected from a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a 13-actin promoter. In some embodiments, the expression construct further comprises a polyadenylation signal. In some embodiments, the polyadenylation signal is a bovine growth hormone polyadenylation signal, an SV40 polyadenylation signal, or a HSV TK pA.

In some embodiments, the invention provides a vector comprising the expression construct as described herein. In some embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5. In other embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In other embodiments, the vector is a rHSV vector. In some embodiments, the rHSV vector is derived from rHSV-1 or rHSV-2.

In some embodiments of the above aspects and embodiments, the invention provides a rAAV vector comprising expression construct encoding an RNAi as described herein. In some embodiments, the expression construct is flanked by one or more AAV inverted terminal repeat (ITR) sequences. In some embodiments, the expression construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffer nucleic acid. In some embodiments, the stuffer nucleic acid is located between the promoter and the nucleic acid encoding the RNAi. In some embodiments, the vector is a self-complementary rAAV vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence. In some embodiments, the invention provides a cell comprising a vector (e.g., a rAAV vector) as described herein.

In some embodiments of the above aspects and embodiments, the invention provides a viral particle comprising the vector encoding an RNAi as described herein wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector. In some embodiments, the viral particle is an adenovirus particle encapsidating the recombinant adenoviral vector. In some embodiments, the adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the adenovirus particle comprises an adenovirus serotype 2 capsid or a variant of an adenoviral serotype 5 capsid. In other embodiments, the viral particle is a lentiviral particle encapsidating the recombinant lentiviral vector. In some embodiments, the lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In other embodiments, the viral particle is a HSV particle. In some embodiments, the HSV particle is a rHSV-1 particle or a rHSV-2 particle.

In some embodiments, the invention provides a recombinant AAV particle comprising a rAAV vector encoding an RNAi as described herein. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In other embodiments, the ITR and the capsid of the rAAV viral particle are derived from different AAV serotypes. In some embodiments, the ITR is derived from AAV2 and the capsid of the rAAV particle is derived from AAV1.

In some embodiments, the invention provides a composition comprising the viral particle (e.g., rAAV particle) comprising a vector encoding a RNAi as described herein. In some embodiments, the composition further comprises a pharmaceutically acceptable carrier.

In some aspects the invention provides a method for inhibiting or reducing the expression of a polypeptide in a mammal disease comprising administering to the mammal a RNAi, an expression construct, a vector, a rAAV vector, a viral particle, a rAAV particle, or a composition as described herein, wherein the RNAi targets an RNA encoding the polypeptide. In some embodiments, the invention provides a method for inhibiting the accumulation of a polypeptide in a cell of a mammal comprising administering to the mammal a RNAi, an expression construct, a vector, a rAAV vector, a viral particle, a rAAV particle, or a composition as described herein, wherein the RNAi targets an RNA encoding the polypeptide. In some embodiments, the mammal is a human.

In some embodiments the invention provides the use of a RNAi, an expression construct, a vector, a rAAV vector, a viral particle, a rAAV particle, or a composition as described herein in the manufacture of a medicament for use in any of the method described herein. In some embodiments, the invention provides a RNAi, an expression construct, a vector, a rAAV vector, a viral particle, a rAAV particle, or a composition as described herein for use in any of the method described herein. In some embodiments, the invention provides a kit for inducing RNA interference in a mammal comprising a RNAi, an expression construct, a vector, a rAAV vector, a viral particle, a rAAV particle, or a composition as described herein. In some embodiments, the mammal is a human. In some embodiments, the kit is for use in any of the methods as described herein.

In some aspects, the invention provides an RNAi comprising a first strand comprising a guide region comprising the sequence 5'-UAGACAAUGAUUCACACGGU-3' (SEQ ID NO:1) and a second strand comprising a non-guide region comprising the sequence 5'-ACCGUGUGUCAUUGUCUAA-3' (SEQ ID NO:2), wherein the first strand and second strand form a duplex and wherein the A residue at residue 18 or residue 19 of the second strand forms a bulge in the non-guide region. In some embodiments, the guide region comprises a nucleic acid sequence having about 90% identity to SEQ ID NO:1. In some embodiments, the non-guide region comprises a nucleic acid sequence having about 90% identity to SEQ ID NO:2. In some embodiments, U residues at residues 11 and 12 of the guide region forms a bulge in the guide region. In some embodiments, the duplex is between 19 and 25 or 19 and 23 base pairs in length. In some embodiments, the first and/or second strand further comprises a 3' overhang region, a 5' overhang region, or both 3' and 5' overhang regions. In some embodiments, the first strand and the second strand are linked by means of a RNA linker capable of forming a loop structure. In some embodiments, the RNA linker capable of forming a loop structure comprises from 4 to 50 nucleotides. In some embodiments, the RNA linker capable of forming a loop structure comprises from 4 to 20 nucleotides. In some embodiments, RNA linker capable of forming a loop structure comprises 13 nucleotides. In some embodiments, the RNAi comprises the nucleotide sequence of SEQ ID NO:3. In other embodiments, the RNAi comprises a nucleotide sequence about 90% identical to the nucleotide sequence of SEQ ID NO:3. In some embodiments, the RNAi is a small inhibitory RNA (siRNA), a microRNA (miRNA), or a small hairpin RNA (shRNA).

In some embodiments of the above aspects, the nucleic acid sequence of the RNAi is improved to reduce off-target gene silencing. In some embodiments, the sequence comprises one or more CpG motifs. In some embodiments, the sequence comprises one or more CpG motifs in the seed region. In some embodiments, the RNAi comprises a first strand comprising a guide region comprising the sequence 5'-UCGACAAUGAUUCACACGGU-3' (SEQ ID NO:15) and a non-guide region comprising the sequence 5'-ACCGUGUGUCAUUGUCGAA-3' (SEQ ID NO:16), wherein the first strand and second strand form a duplex and wherein the A residue at residue 18 or residue 19 of the second strand forms a bulge in the non-guide region. In some embodiments, the RNAi comprises a first strand comprising a guide region comprising the sequence 5'-UAGACGAUGAUUCACACGGU-3' (SEQ ID NO:17) and a non-guide region comprising the sequence 5'-ACCGUGUGUCAUCGUCUAA-3' (SEQ ID NO:18), wherein the first strand and second strand form a duplex and wherein the A residue at residue 18 or residue 19 of the second strand forms a bulge in the non-guide region. In some embodiments, the guide region comprises a nucleic acid sequence having about 90% identity to SEQ ID NO:15 and the non-guide region comprises a nucleic acid sequence having about 90% identity to SEQ ID NO:16 or a nucleic acid sequence having about 90% identity to SEQ ID NO:17 and the non-guide region comprises a nucleic acid sequence having about 90% identity to SEQ ID NO:18.

In some embodiments, the invention provides an expression construct comprising nucleic acid encoding the RNAi as described above. In some embodiments, the nucleic acid encoding the RNAi comprises a miRNA scaffold. In some embodiments, the nucleic acid encoding the RNAi comprises a miR-155 scaffold. In some embodiments, the nucleic acid encoding the RNAi is operably linked to a promoter. In some embodiments, the promoter is capable of expressing the RNAi in the brain of a mammal. In some embodiments, the promoter is selected from a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a 13-actin promoter. In some embodiments, the promoter is a hybrid chicken β-actin promoter. In some embodiments, the expression construct further comprises a polyadenylation signal. In some embodiments, the polyadenylation signal is a bovine growth hormone polyadenylation signal.

In some embodiments, the invention provides a vector comprising the expression construct as described above. In some embodiments, the vector is a recombinant adeno-associated virus (rAAV) vector, a recombinant adenoviral vector, a recombinant lentiviral vector or a recombinant herpes simplex virus (HSV) vector. In some embodiments, a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5. In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the vector is a rHSV vector. In some embodiments, the rHSV vector is derived from rHSV-1 or rHSV-2.

In some embodiments, the invention provides a recombinant AAV (rAAV) vector comprising an expression construct encoding the RNAi as described above. In some embodiments, the expression construct is flanked by one or more AAV inverted terminal repeat (ITR) sequences. In some embodiments, the expression construct is flanked by two AAV ITRs. In some embodiments, the AAV ITRs are AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the rAAV vector comprises 5' to 3' an AAV2 ITR, a promoter, nucleic acid encoding the RNAi, a polyadenylation signal, and an AAV2 ITR. In some embodiments, the promoter is a CBA promoter. In some embodiments, the polyadenylation signal is a bovine growth hormone polyadenylation signal. In some embodiments, the rAAV vector comprises 5' to 3' an AAV2 ITR, the CBA promoter, nucleic acid encoding the RNAi, a bovine growth hormone polyadenylation signal, and an AAV2 ITR. In some embodiments, the vector further comprise a stuffer nucleic acid. In some embodiments, the stuffer nucleic acid comprises nucleic acid encoding a green fluorescent protein (GFP). In some embodiments, the stuffer nucleic acid is located between the promoter and the nucleic acid encoding the RNAi. In some embodiments, the RNAi comprises the nucleotide sequence of SEQ ID NO:3. In other embodiments, the RNAi comprises a nucleotide sequence about 90% identical to the nucleotide sequence of SEQ ID NO:3. In some embodiments, the vector is a self-complementary vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments, the invention provides a cell comprising the vector or the rAAV vector as described herein. In some embodiments, the cell is a central nervous system (CNS) cell.

In some embodiments, the invention provides a viral particle comprising a vector encoding an RNAi as described above, wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector. In some embodiments, the viral particle is an adenovirus particle encapsidating the recombinant adenoviral vector. In some embodiments, the adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the adenovirus particle comprises an adenovirus serotype 2 capsid or a variant of an adenoviral serotype 5 capsid. In other embodiments, the viral particle is a lentiviral particle encapsidating the recombinant lentiviral vector. In some embodiments, the lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In other embodiments, the viral particle is a HSV particle. In some embodiments, the HSV particle is a rHSV-1 particle or a rHSV-2 particle.

In some embodiments, the invention provides a recombinant AAV particle comprising the rAAV vector encoding a RNAi as described above. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/ 2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In other embodiments, the ITR and the capsid of the rAAV viral particles are derived from different AAV serotypes. In some embodiments, the rAAV viral particle comprises AAV2 capsid. In some embodiments, the rAAV viral particle comprises an AAV1 capsid, and wherein the vector comprises AAV2 ITRs.

In some embodiments, the invention provides a composition comprising the viral particle or the rAAV particle as described above. In further embodiments, the composition comprises a pharmaceutically acceptable carrier. In some embodiments, the invention provides a method for treating Huntington's disease in a mammal comprising administering to the mammal the composition. In some embodiments, the invention provides a method for inhibiting the expression of htt in a mammal with Huntington's disease comprising administering to the mammal the composition. In some embodiments, the invention provides a method for inhibiting the accumulation of htt in a cell of a mammal with Huntington's disease comprising administering to the mammal the composition.

In some aspects, the invention provides methods for treating Huntington's disease in a mammal comprising administering to the mammal an RNAi comprising a first strand comprising a first nucleic acid comprising the sequence 5'-UAGACAAUGAUUCACACGGU-3' (SEQ ID NO:1) and a second strand comprising a second nucleic acid comprising the sequence 5'-ACCGUGUGUCAUUGUC-UAA-3' (SEQ ID NO:2), wherein the A residue at residue 18 or residue 19 of the second strand does not form a basepair with a residue in the first strand. In some aspects, the invention provides a method for inhibiting the expression of htt in a mammal with Huntington's disease comprising administering to the mammal an RNAi comprising a first strand comprising a first nucleic acid comprising the sequence 5'-UAGACAAUGAUUCACACGGU-3' (SEQ ID NO:1) and a second strand comprising a second nucleic acid comprising the sequence 5'-ACCGUGUGUCAUUGUC-UAA-3' (SEQ ID NO:2), wherein the A residue at residue 18 or residue 19 of the second strand does not form a basepair with a residue in the first strand. In some aspects, the invention provides a method for inhibiting the accumulation of htt in a cell of a mammal with Huntington's disease comprising administering to the mammal an RNAi comprising a first strand comprising a first nucleic acid comprising the sequence 5'-UAGACAAUGAUUCACACGGU-3' (SEQ ID NO:1) and a second strand comprising a second nucleic acid comprising the sequence 5'-ACCGUGUGUCAUUGU-CUAA-3' (SEQ ID NO:2), wherein the A residue at residue 18 or residue 19 of the second strand does not form a basepair with a residue in the first strand.

In some embodiments of the above methods, the guide region comprises a nucleic acid sequence having about 90% identity to SEQ ID NO:1. In some embodiments, the non-guide region comprises a nucleic acid sequence having about 90% identity to SEQ ID NO:2. In some embodiments, U residues at residues 11 and 12 of the guide region forms a bulge in the guide region. In some embodiments, the duplex is between 19 and 25 or 19 and 23 base pairs in length. In some embodiments, the first and/or second strand further comprises a 3' overhang region, a 5' overhang region, or both 3' and 5' overhang regions. In some embodiments, the first strand and the second strand are linked by means of a RNA linker capable of forming a loop structure. In some embodiments, the RNA linker capable of forming a loop structure comprises from 4 to 50 nucleotides. In some embodiments, the RNA linker capable of forming a loop structure comprises from 4 to 20 nucleotides. In some embodiments, RNA linker capable of forming a loop structure comprises 13 nucleotides. In some embodiments, the RNAi comprises the nucleotide sequence of SEQ ID NO:3. In other embodiments, the RNAi comprises a nucleotide sequence about 90% identical to the nucleotide sequence of SEQ ID NO:3. In some embodiments, the RNAi is a small inhibitory RNA (siRNA), a microRNA (miRNA), or a small hairpin RNA (shRNA).

In some embodiments of the above methods, the nucleic acid is improved to reduce off-target gene silencing. In some embodiments, the nucleic acid comprises one or more CpG motifs. In some embodiments, the nucleic acid comprises one or more CpG motifs in a seed region.

In some embodiments the invention provides methods for treating Huntington's disease in a mammal comprising administering to the mammal an RNAi comprising a first strand comprising a first nucleic acid comprising the sequence 5'-UCGACAAUGAUUCACACGGU-3' (SEQ ID NO:15) and a second strand comprising a second nucleic acid comprising the sequence 5'-ACCGUGUGUCAUUGU-CGAA-3' (SEQ ID NO:16), wherein the A residue at residue 18 or residue 19 of the second strand does not form a basepair with a residue in the first strand. In some embodiments the invention provides methods for inhibiting the expression of htt in a mammal with Huntington's disease comprising administering to the mammal an RNAi comprising a first strand comprising a first nucleic acid comprising the sequence 5'-UCGACAAUGAUUCACACGGU-3' (SEQ ID NO:15) and a second strand comprising a second nucleic acid comprising the sequence 5'-ACCGUGUGUCAUUGU-CGAA-3' (SEQ ID NO:16), wherein the A residue at residue 18 or residue 19 of the second strand does not form a basepair with a residue in the first strand. In some embodiments the invention provides methods for inhibiting the accumulation of htt in a cell of a mammal with Huntington's disease comprising administering to the mammal an RNAi comprising a first strand comprising a first nucleic acid comprising the sequence 5'-UCGACAAUGAUUCA-CACGGU-3' (SEQ ID NO:15) and a second strand comprising a second nucleic acid comprising the sequence 5'-ACCGUGUGUCAUUGUCGAA-3' (SEQ ID NO:16), wherein the A residue at residue 18 or residue 19 of the second strand does not form a basepair with a residue in the first strand. In some embodiments, the first strand comprises a nucleic acid sequence having about 90% identity to SEQ ID NO:15 but maintains the CpG motif. In some embodiments, the second strand comprises a nucleic acid sequence having about 90% identity to SEQ ID NO:16 but maintains the CpG motif.

In some embodiments the invention provides methods for treating Huntington's disease in a mammal comprising administering to the mammal an RNAi comprising a first strand comprising a first nucleic acid comprising the sequence 5'-UAGACGAUGAUUCACACGGU-3' (SEQ ID NO:17) and a second strand comprising a second nucleic acid comprising the sequence 5'-ACCGUGUGUCAUCGU-CUAA-3' (SEQ ID NO:18), wherein the A residue at residue 18 or residue 19 of the second strand does not form a basepair with a residue in the first strand. In some embodiments the invention provides methods for inhibiting the expression of htt in a mammal with Huntington's disease comprising administering to the mammal an RNAi comprising a first strand comprising a first nucleic acid comprising the sequence 5'-UAGACGAUGAUUCACACGGU-3' (SEQ ID NO:17) and a second strand comprising a second nucleic acid comprising the sequence 5'-ACCGUGUGUCAUCGU-CUAA-3' (SEQ ID NO:18), wherein the A residue at residue 18 or residue 19 of the second strand does not form a basepair with a residue in the first strand. In some embodiments the invention provides methods for inhibiting the accumulation of htt in a cell of a mammal with Huntington's disease comprising administering to the mammal an RNAi comprising a first strand comprising a first nucleic acid comprising the sequence 5'-UAGACGAUGAUUCA-CACGGU-3' (SEQ ID NO:17) and a second strand comprising a second nucleic acid comprising the sequence 5'-ACCGUGUGUCAUCGUCUAA-3' (SEQ ID NO:18), wherein the A residue at residue 18 or residue 19 of the second strand does not form a basepair with a residue in the first strand. In some embodiments, the first strand comprises a nucleic acid sequence having about 90% identity to SEQ ID NO:17 but maintains the CpG motif. In some embodiments, the second strand comprises a nucleic acid sequence having about 90% identity to SEQ ID NO:18 but maintains the CpG motif.

In some embodiments of the above methods, the expression construct comprising nucleic acid encoding the RNAi as described above. In some embodiments, the nucleic acid encoding the RNAi comprises a miRNA scaffold. In some embodiments, the nucleic acid encoding the RNAi comprises a miR-155 scaffold. In some embodiments, the nucleic acid encoding the RNAi is operably linked to a promoter. In some embodiments, the promoter is capable of expressing the RNAi in the brain of a mammal. In some embodiments, the promoter is selected from a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a 13-actin promoter. In some embodiments, the promoter is a hybrid chicken β-actin promoter. In some embodiments, the expression construct further comprises a polyadenylation signal. In some embodiments, the polyadenylation signal is a bovine growth hormone polyadenylation signal. In some embodiments, In some embodiments of the above methods, the vector comprising the expression construct as described above. In some embodiments, the vector is a recombinant adeno-associated virus (rAAV) vector, a recombinant adenoviral vector, a recombinant lentiviral vector or a recombinant herpes simplex virus (HSV) vector. In some embodiments, a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5. In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the vector is a rHSV vector. In some embodiments, the rHSV vector is derived from rHSV-1 or rHSV-2.

In some embodiments of the above methods, the recombinant AAV (rAAV) vector comprising an expression construct encoding the RNAi as described above. In some embodiments, the expression construct is flanked by one or more AAV inverted terminal repeat (ITR) sequences. In some embodiments, the expression construct is flanked by two AAV ITRs. In some embodiments, the AAV ITRs are AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the rAAV vector comprises 5' to 3' an AAV2 ITR, a promoter, nucleic acid encoding the RNAi, a polyadenylation signal, and an AAV2 ITR. In some embodiments, the promoter is a CBA promoter. In some embodiments, the polyadenylation signal is a bovine growth hormone polyadenylation signal. In some embodiments, the rAAV vector comprises 5' to 3' an AAV2 ITR, the CBA promoter, nucleic acid encoding the RNAi, a bovine growth hormone polyadenylation signal, and an AAV2 ITR. In some embodiments, the vector further comprise a stuffer nucleic acid. In some embodiments, the stuffer nucleic acid comprises nucleic acid encoding a green fluorescent protein (GFP). In some embodiments, the stuffer nucleic acid is located between the promoter and the nucleic acid encoding the RNAi. In some embodiments, the RNAi comprises the nucleotide sequence of SEQ ID NO:3. In other embodiments, the RNAi comprises a nucleotide sequence about 90% identical to the nucleotide sequence of SEQ ID NO:3. In some embodiments, the vector is a self-complementary vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above methods, the viral particle comprising a vector encoding an RNAi as described above, wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector. In some embodiments, the viral particle is an adenovirus particle encapsidating the recombinant adenoviral vector. In some embodiments, the adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the adenovirus particle comprises an adenovirus serotype 2 capsid or a variant of an adenoviral serotype 5 capsid. In other embodiments, the viral particle is a lentiviral particle encapsidating the recombinant lentiviral vector. In some embodiments, the lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In other embodiments, the viral particle is a HSV particle. In some embodiments, the HSV particle is a rHSV-1 particle or a rHSV-2 particle.

In some embodiments of the above methods, the recombinant AAV particle comprising the rAAV vector encoding a RNAi as described above. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In other embodiments, the ITR and the capsid of the rAAV viral particles are derived from different AAV serotypes. In some embodiments, the rAAV viral particle comprises AAV2 capsid. In some embodiments, the rAAV viral particle comprises an AAV1 capsid, and wherein the vector comprises AAV2 ITRs.

In some embodiments of the above methods the viral particle or the rAAV particle is in a composition. In some embodiments, the composition further comprises a pharmaceutically acceptable carrier.

In some embodiments the invention provides the use of a RNAi, an expression construct, a vector, a rAAV vector, a viral particle, a rAAV particle, or a composition as described herein in the manufacture of a medicament for use in any of the method to treat Huntington's disease described herein. In some embodiments, the invention provides a RNAi, an expression construct, a vector, a rAAV vector, a viral particle, a rAAV particle, or a composition as described herein for use in any of the method to treat Huntington's disease described herein. In some embodiments, the invention provides a kit for inducing RNA interference to treat Huntington's disease in a mammal comprising a RNAi, an expression construct, a vector, a rAAV vector, a viral particle, a rAAV particle, or a composition as described herein. In some embodiments, the mammal is a human. In some embodiments, the kit is for use in any of the methods as described herein.

All references cited herein, including patent applications and publications, are incorporated by reference in their entirety.

BRIEF DESCRIPTION OF THE DRAWINGS

(FIG. 1A) Schematic of the previral construct used to generate AAV2/1-miRNA-Htt. The plasmid was designed to express GFP and a miRNA sequence against Htt under the transcriptional control of the chicken β-actin (CBA) promoter. ITR, inverted terminal repeat. eGFP, enhanced green fluorescent protein. PolyA, bovine growth hormone polyA.

(FIG. 2A) Flow cytometric scatter profile of HEK293 cells with eGFP. Forward light scatter A (FSC-A) represents relative cell size, area and SSC-A represents relative cell complexity, area with each dot representing one cell. (FIG. 2B) A fluorescence plot of eGFP fluorescent intensities of cells with each color demarcating cells sorted as GFP−, GFP+, GFP++, or GFP+++, respectively. (FIG. 2C) FACS histogram of HEK293 cells expressing eGFP. (FIG. 2D) Table of cell counts following FACS sorting.

FIGS. 3A-E show widespread striatal transduction and Htt reduction following intrastriatal injection of AAV2/1-miRNA-Htt injection in YAC128 mice. (FIG. 3A) Flow cytometric scatter profile of striatal cells with eGFP. Forward light scatter A (FSC-A) represents relative cell size, area and SSC-A represents relative cell complexity, area with each dot representing one cell. (FIG. 3B) Dot plot using a FSC-A versus FITC-A analysis. Dead cells were sorted out and eGFP+ and eGFP− cells were selected. GFP expression from these cells was evaluated and quantified and shown in FIG. 3C. (FIG. 3C) A fluorescence plot of eGFP fluorescent intensity collected with a 530/30BP filter 505LP. (FIG. 3D) Fluorescence microscopy showing widespread eGFP expression throughout the striatum following intracranial administration of AAV2/1-eGFP-miRNA-Htt. (FIG. 3E) Quantitative PCR analysis evaluating Htt mRNA levels in the striatum 1 and 5 months after injection of AAV2/1-miRNA-Htt or AAV2/1-null control vector. PPIA served as a normalization control gene. Values are given as the means±SEM. *$p<0.05$. AAV2/1-miRNA-Htt-treated YAC128 mice (N=8) showed an approximately 50% reduction in Htt mRNA levels in the striatum when compared to AAV2/1-Null-injected mice (N=8 per time point) at 1 and 5 months post-treatment.

FIGS. 5A-I demonstrate that sustained lowering of Htt levels in YAC128 mice by AAV2/1-miRNA-Htt did not cause overt neuroinflammation. (FIGS. 5A-C) Hematoxylin and Eosin (H&E) staining of striatal tissue sections from YAC128 mice treated using AAV2/1-miRNA-Htt at 1 (FIG. 5B) or 5 months (FIG. 5C) post AAV-miRNA-Htt injection, compared to YAC128 mice treated using AAV2/1-Null vectors (FIG. 5A). (FIGS. 5D-F) GFAP immunohistochemical staining of striatal tissue sections from YAC128 mice treated using AAV2/1-miRNA-Htt at 1 (FIG. 5E) or 5 months (FIG. 5F) post AAV-miRNA-Htt injection, compared to YAC128 mice treated using AAV2/1-Null vectors (FIG. 5D). (FIGS. 5G-I) Iba-1immunohistochemical staining of striatal tissue sections from YAC128 mice treated using AAV2/1-miRNA-Htt at 1 (FIG. 5H) or 5 months (FIG. 5I) post AAV-miRNA-Htt injection, compared to YAC128 mice treated using AAV2/1-Null vectors (FIG. 5G). All photographs were exposure-matched for accurate comparisons. Scale bar: 0.25 mm.

(FIG. 5J) Striatal levels of GFAP mRNA levels by QPCR at 1 or 5 months following the injection of AAV2/1-miRNA-Htt.

(FIG. 6A) Illustration of experimental timeline. Two month-old YAC128 and wild-type mice received bilateral striatal injections of either AAV2/1-miRNA-Htt (N=8 YAC and N=8 WT) or AAV2/1-Null control (N=8 YAC and N=8 WT) and were subjected to a rotarod test and the Porsolt swim test at 4 and 5 months of age, respectively. All mice were sacrificed at 5 months old, and tissues were then collected for biochemical and histological analyses. (FIG. 6B) Fluorescent microscopy showing eGFP expression in the striatum at 3 months post-treatment. Mouse (FIG. 6C) and Human (FIG. 6D) Htt protein levels by Western blot 3 months following AAV2/1-miRNA-Htt-treatment.

(FIG. 6E) Accelerating rotarod test at 2 months following the injection of AAV2/1-miRNA-Htt.

(FIG. 7A) Striatal DARPP-32 mRNA levels in YAC128 and FVB wild-type littermate mice following AAV2/1-Null or AAV2/1-miRNA-Htt treatment.

FIGS. 8A-D show intracranial administration of AAV2/1-miRNA-Htt ameliorated motor deficits and reduced mutant Htt aggregates in the striatum of aged YAC128 mice. (FIG. 8A) Immunohistochemical staining of YAC128 mouse brain sections showing mutant Htt aggregates in the striatum. Aggregates were observed in 6, 9, 12 (not shown) and 24-month old YAC128 mice. Wild type mice exhibited no aggregates at all ages tested. (FIG. 8B) An illustration of the experimental timeline for testing AAV2/1-miRNA-HTT in aged YAC 128 and wild-type mice. Seven-month-old mice received bilateral intrastriatal injections of AAV2/1-miRNA-Htt (N=6 YAC and N=4 WT) or AAV2/1-GFP control (N=6 YAC and N=4 WT) and were then subjected to behavioral testing at 10 months of age. Brains were harvested at 5 months post-injection (when the mice were 12 months old). (FIG. 8C) Performance of aged YAC128 mice on the rotarod test at 3 months following injection of AAV-miRNA-Htt. (FIG. 8D) EM-48 immunohistochemical analysis of brain sections of AAV2/1-miRNA-Htt or AAV2/1-eGFO treated YAC 128 mice at 5 months post-treatment.

DETAILED DESCRIPTION

Figure 1A:
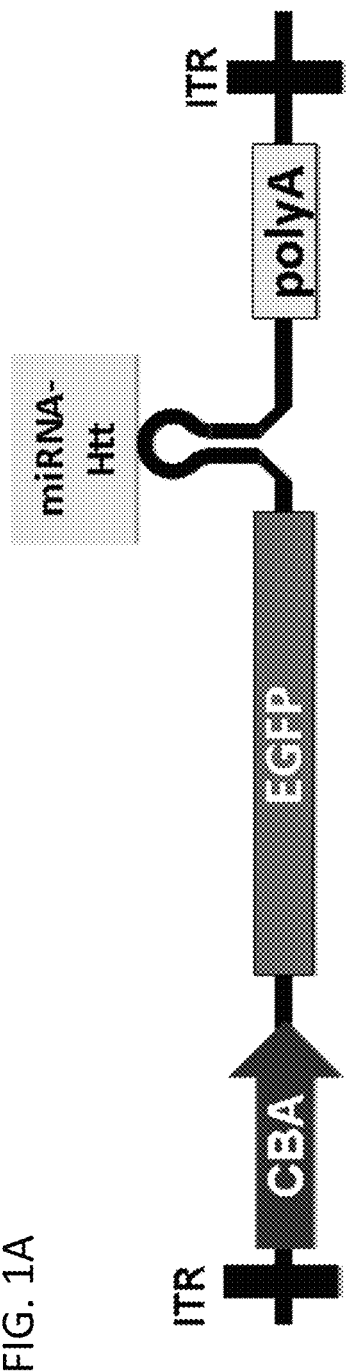
FIGS. 1A&B show AAV2/1-miRNA-Htt mediated reduction of Htt levels in vitro.

In some aspects the invention provides improved RNAi; for example, improved RNAi for therapeutic uses. In some embodiments, the RNAi comprises a first strand and a second strand, wherein a) the first strand and the second form a duplex; b) the first strand comprises a guide region of at least 11 bases, wherein the guide region comprises a seed region comprising bases 1–N of the guide strand, wherein N=7 or N=8; and c) the second strand comprises a non-guide region of at least 11 bases, wherein the non-guide region comprises a bulge sequence opposite of any one or more of bases 1–(N+2) of the guide region in the duplex. In some embodiments, the RNAi comprises a first strand and a second strand, wherein a) the first strand and the second form a duplex; b) the first strand comprises a guide region of at least 10 bases, wherein the guide region comprises a seed region comprising bases 1–N of the guide strand, wherein N=7 or N=8; and c) the second strand comprises a non-guide region of at least 10 bases, wherein the non-guide region comprises a bulge sequence opposite of any one or more of bases 1–(N+1) of the guide region in the duplex. In some embodiments, the RNAi comprises a first strand and a second strand, wherein a) the first strand and the second form a duplex, b) the first strand comprises a guide region of at least 9 bases, wherein the guide region comprises a seed region comprising bases 2-7 or 2-8 of the guide strand, and c) the second strand comprises a non-guide region of at least 9 bases, wherein the non-guide region comprises a bulge sequence opposite of base 1 or base 9 of the guide region in the duplex. In some embodiments, the RNAi comprises a first strand and a second strand, wherein a) the first strand and the second form a duplex, b) the first strand comprises a guide region of at least 9 bases, wherein the guide region comprises a seed region comprising bases 2-7 or 2-8 of the guide strand, and c) the second strand comprises a non-guide region of at least 9 bases, wherein the non-guide region comprises a bulge sequence opposite of base 1 of the guide region in the duplex. In some embodiments, the RNAi is an artificial RNAi.

In some aspects, the invention provides expression cassettes, vectors (e.g., recombinant AAV, adenoviral, lentiviral, or HSV vectors), cells, viral particles (e.g., AAV, adenoviral, lentiviral, or HSV viral particles), and pharmaceutical compositions comprising an RNAi of the present disclosure. In further aspects, the invention provides methods for treating a disease or disorder in a mammal comprising administering to the mammal a pharmaceutical composition comprising an RNAi of the present disclosure. In yet further aspects, the invention provides kits comprising an RNAi of the present disclosure.

In some aspects, the invention provides RNAi for treating Huntington's disease. In some embodiments, the RNAi comprises a first strand comprising a first nucleic acid comprising the sequence 5'-UAGACAAUGAUUCA-CACGGU-3' (SEQ ID NO:1) and a second strand comprising a second nucleic acid comprising the sequence 5'-AC-CGUGUGCAUUGUCUAA-3' (SEQ ID NO:2), where the first strand and second strand form a duplex and wherein the A residue at residue 18 or residue 19 of SEQ ID NO:2 the second strand does not form a basepair with a residue in the first strand. In some aspects, the invention provides expression cassettes, vectors (e.g., recombinant AAV, adenoviral, lentiviral, or HSV vectors), cells, viral particles (e.g., AAV, adenoviral, lentiviral, or HSV viral particles), and pharmaceutical compositions comprising an RNAi of the present disclosure. In further aspects, the invention provides methods for treating Huntington's disease, inhibiting the expression of htt, and inhibiting the accumulation of htt in a cell in a mammal comprising administering to the mammal a pharmaceutical composition comprising an RNAi of the present disclosure. In still further aspects, the invention provides for the use of a pharmaceutical composition comprising an RNAi of the present disclosure to treat Huntington's disease (e.g., ameliorate the symptoms of Huntington's disease), inhibit the expression of htt, or inhibit the accumulation of htt in a cell in a mammal with Huntington's disease. In yet further aspects, the invention provides kits for treating Huntington's disease in a mammal comprising an RNAi of the present disclosure.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); Short Protocols in Molecular Biology (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—$NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one and in embodiments two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, and in embodiments two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV vector can be in any of a number of forms, including, but not limited to, plasmids, linear artificial chromosomes, complexed with lipids, encapsulated within liposomes, and encapsidated in a viral particle, particularly an AAV particle. A rAAV vector can be packaged into an AAV virus capsid to generate a "recombinant adeno-associated viral particle (rAAV particle)".

A "recombinant adenoviral vector" refers to a polynucleotide vector comprising one or more heterologous sequences (i.e., nucleic acid sequence not of adenovirus origin) that are flanked by at least one adenovirus inverted terminal repeat sequence (ITR). In some embodiments, the recombinant nucleic acid is flanked by two inverted terminal repeat sequences (ITRs). Such recombinant viral vectors can be replicated and packaged into infectious viral particles when present in a host cell that is expressing essential adenovirus genes deleted from the recombinant viral genome (e.g., E1 genes, E2 genes, E4 genes, etc.). When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of adenovirus packaging functions. A recombinant viral vector can be in any of a number of forms, including, but not limited to, plasmids, linear artificial chromosomes, complexed with lipids, encapsulated within liposomes, and encapsidated in a viral particle, for example, an adenovirus particle. A recombinant viral vector can be packaged into an adenovirus virus capsid to generate a "recombinant adenoviral particle."

A "recombinant lentivirus vector" refers to a polynucleotide vector comprising one or more heterologous sequences (i.e., nucleic acid sequence not of lentivirus origin) that are flanked by at least one lentivirus terminal repeat sequences (LTRs). In some embodiments, the recombinant nucleic acid is flanked by two lentiviral terminal repeat sequences (LTRs). Such recombinant viral vectors can be replicated and packaged into infectious viral particles when present in a host cell that has been infected with a suitable helper functions. A recombinant lentiviral vector can be packaged into a lentivirus capsid to generate a "recombinant lentiviral particle."

A "recombinant herpes simplex vector (recombinant HSV vector)" refers to a polynucleotide vector comprising one or more heterologous sequences (i.e., nucleic acid sequence not of HSV origin) that are flanked by HSV terminal repeat sequences. Such recombinant viral vectors can be replicated and packaged into infectious viral particles when present in a host cell that has been infected with a suitable helper functions. When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of HSV packaging functions. A recombinant viral vector can be in any of a number of forms, including, but not limited to, plasmids, linear artificial chromosomes, complexed with lipids, encapsulated within liposomes, and encapsidated in a viral particle, for example, an HSV particle. A recombinant viral vector can be packaged into an HSV capsid to generate a "recombinant herpes simplex viral particle."

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA.

"Chicken β-actin (CBA) promoter" refers to a polynucleotide sequence derived from a chicken β-actin gene (e.g., *Gallus gallus* beta actin, represented by GenBank Entrez Gene ID 396526). As used herein, "chicken β-actin promoter" may refer to a promoter containing a cytomegalovirus (CMV) early enhancer element, the promoter and first exon and intron of the chicken β-actin gene, and the splice acceptor of the rabbit beta-globin gene, such as the sequences described in Miyazaki, J. et al. (1989) *Gene* 79(2):269-77. As used herein, the term "CAG promoter" may be used interchangeably. As used herein, the term "CMV early enhancer/chicken beta actin (CAG) promoter" may be used interchangeably.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting the expression of a gene may refer to any act leading to a blockade, reduction, elimination, or any other antagonism of expression of the gene, including reduction of mRNA abundance (e.g., silencing mRNA transcription), degradation of mRNA, inhibition of mRNA translation, and so forth. In some embodiments, inhibiting the expression of HTT may refer a blockade, reduction, elimination, or any other antagonism of expression of HTT, including reduction of HTT mRNA abundance (e.g., silencing HTT mRNA transcription), degradation of HTT mRNA, inhibition of HTT mRNA translation, and so forth. As another example, inhibiting the accumulation of a protein in a cell may refer to any act leading to a blockade, reduction, elimination, or other antagonism of expression of the protein, including reduction of mRNA abundance (e.g., silencing mRNA transcription), degradation of mRNA, inhibition of mRNA translation, degradation of the protein, and so forth. In some embodiments, inhibiting the accumulation of HTT protein in a cell refers to a blockade, reduction, elimination, or other antagonism of expression of the HTT protein in a cell, including reduction of HTT mRNA abundance (e.g., silencing HTT mRNA transcription), degradation of HTT mRNA, inhibition of HTT mRNA translation, degradation of the HTT protein, and so forth The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

"AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

A "helper virus" for AAV refers to a virus that allows AAV (which is a defective parvovirus) to be replicated and packaged by a host cell. A helper virus provides "helper functions" which allow for the replication of AAV. A number of such helper viruses have been identified, including adenoviruses, herpesviruses and, poxviruses such as vaccinia and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Examples of adenovirus helper functions for the replication of AAV include E1A functions, E1B functions, E2A functions, VA functions and E4orf6 functions. Baculoviruses available from depositories include *Autographa californica* nuclear polyhedrosis virus.

A preparation of rAAV is said to be "substantially free" of helper virus if the ratio of infectious AAV particles to infectious helper virus particles is at least about $10^2$:1; at least about $10^4$:1, at least about $10^6$:1; or at least about $10^8$:1 or more. In some embodiments, preparations are also free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

"Huntington's disease (HD)" refers to the progressive brain disorder typically caused by mutations in the HTT gene (aka huntingtin, HD or IT15). It may be characterized by symptoms including abnormal movements (termed chorea), gradual loss of motor function, emotional or psychiatric illnesses, and progressively impaired cognition. Although most symptoms appear in the 30 s and 40 s, juvenile forms of the disease have also been observed. For further description of HD, see OMIM Entry No. 143100.

"Huntingtin (HTT)" may refer either to the gene or to a polypeptide product thereof associated with most cases of Huntington's disease. The normal function of huntingtin is not fully understood. However, mutations in the huntingtin gene are known to cause HD. These mutations are typically inherited in an autosomal dominant fashion and involve expansion of trinucleotide CAG repeats in the HTT gene, leading to a polyglutamine (polyQ) tract in the Htt protein.

As used herein, an "RNAi" may refer to any RNA molecule that induces RNA interference in a cell. Examples of RNAi include without limitation small inhibitory RNAs (siRNAs), microRNAs (miRNAs), and small hairpin RNAs (shRNAs).

"miRNA scaffold" may refer to a polynucleotide containing (i) a double-stranded sequence targeting a gene of interest for knockdown by RNAi and (ii) additional sequences that form a stem-loop structure resembling that of endogenous miRNAs. A sequence targeting a gene of interest for RNAi (e.g., a short, ~20-nt sequence) may be ligated to sequences that create a miRNA-like stem-loop and a sequence that base pairs with the sequence of interest to form a duplex when the polynucleotide is assembled into the miRNA-like secondary structure. As described herein, this duplex may hybridize imperfectly, e.g., it may contain one or more unpaired or mispaired bases. Upon cleavage of this polynucleotide by Dicer, this duplex containing the sequence targeting a gene of interest may be unwound and incorporated into the RISC complex. A miRNA scaffold may refer to the miRNA itself or to a DNA polynucleotide encoding the miRNA. An example of a miRNA scaffold is the miR-155 sequence (Lagos-Quintana, M. et al. (2002) Curr. Biol. 12:735-9). Commercially available kits for cloning a sequence into a miRNA scaffold are known in the art (e.g., the Invitrogen™ BLOCK-iT™ Pol II miR RNAi expression vector kit from Life Technologies, Thermo Fisher Scientific; Waltham, Mass.).

As used herein, a "bulge" refers to a region of nucleic acid that is non-complementary to nucleic acid opposite it in a duplex nucleic acid. For example, a bulge may refer to a nucleic acid sequence that is noncomplementary to nucleic acid opposite in a duplex nucleic acid where the bulge is flanked by regions of nucleic acid that are complementary to nucleic acid opposite in a duplex nucleic acid. In some examples, the bulge may be any of 1, 2, 3, 4, 5, 6, 7, 8, 9 10 or greater than 10 bases in length. In some examples, the bulge may be the result of mispairing (e.g., the opposite strand contains a base that is noncomplementary) or the bulge may be the result of nonpairing (e.g., the opposite strand comprises nucleic acid complementary to nucleic acid flanking the bulge but the opposite strand does not contain nucleic acid opposite the bulge).

As used herein, the term "sense" nucleic acid is a nucleic acid comprising a sequence that encodes all or a part of a transgene. In some examples, mRNA for a transgene is a sense nucleic acid.

As used herein, "antisense" nucleic acid is a sequence of nucleic acid that is complementary to a "sense" nucleic acid. For example, an antisense nucleic acid may be complementary to a mRNA encoding a transgene.

As used herein, the "guide region" of an RNAi is the strand of the RNAi that binds the target mRNA, typically on the basis of complementarity. The region of complementarity may encompass the all or a portion of the guide region. Typically, the region of complementarity includes at least the seed region. In many cases, the antisense region of a RNAi is the guide region.

As used herein, the "passenger region," or "non-guide region," used interchangeably herein, of an RNAi is the region of the RNAi that is complementary to the guide region. In many cases, the sense region of a RNAi is the passenger region.

As used herein, the "seed region" of a RNAi (e.g., miRNA) is a region of about 1-8 nucleotides in length of a microRNA. In some examples, the seed region and the 3'-UTR of its target mRNA may be a key determinant in RNAi recognition.

As used herein, "off-target gene silencing" refers to the pairing of a seed region of an RNAi with sequences in 3'-UTRs of unintended mRNAs and directs translational repression and destabilization of those transcripts (e.g., reduces expression of the unintended mRNAs).

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. RNAi

In some aspects, the invention provides improved RNAi. In some embodiments, the RNAi is a small inhibitory RNA (siRNA), a microRNA (miRNA), or a small hairpin RNA (shRNA). A small inhibitory or interfering RNA (siRNA) is known in the art as a double-stranded RNA molecule of approximately 19-25 (e.g., 19-23) base pairs in length that induces RNAi in a cell. A small hairpin RNA (shRNA) is known in the art as an RNA molecule comprising approximately 19-25 (e.g., 19-23) base pairs of double stranded RNA linked by a short loop (e.g., ~4-11 nucleotides) that induces RNAi in a cell.

A microRNA (miRNA) is known in the art as an RNA molecule that induces RNAi in a cell comprising a short (e.g., 19-25 base pairs) sequence of double-stranded RNA linked by a loop and containing one or more additional sequences of double-stranded RNA comprising one or more bulges (e.g., mispaired or unpaired base pairs). As used herein, the term "miRNA" encompasses endogenous miRNAs as well as exogenous or heterologous miRNAs. In some embodiments, "miRNA" may refer to a pri-miRNA or a pre-miRNA. During miRNA processing, a pri-miRNA transcript is produced. The pri-miRNA is processed by Drosha-DGCR8 to produce a pre-miRNA by excising one or more sequences to leave a pre-miRNA with a 5'flanking region, a guide strand, a loop region, a non-guide strand, and a 3'flanking region; or a 5'flanking region, a non-guide strand, a loop region, a guide strand, and a 3'flanking region. The pre-miRNA is then exported to the cytoplasm and processed by Dicer to yield a siRNA with a guide strand and a non-guide (or passenger) strand. The guide strand is then used by the RISC complex to catalyze gene silencing, e.g., by recognizing a target RNA sequence complementary to the guide strand. Further description of miRNAs may be found, e.g., in WO 2008/150897. The recognition of a target sequence by a miRNA is primarily determined by pairing between the target and the miRNA seed sequence, e.g., nucleotides 1-8 (5' to 3') of the guide strand (see, e.g., Boudreau, R. L. et al. (2013) *Nucleic Acids Res.* 41:e9).

In the pri/pre-miRNA structure, the guide strand:non-guide strand interface in a duplex is formed in part through complementary base pairing (e.g., Watson-Crick base pairing). However, in some embodiments, this complementary base pairing does not extend through the entire duplex. In some embodiments, a bulge in the interface may exist at one or more nucleotide positions. As used herein, the term "bulge" may refer to a region of nucleic acid that is non-complementary to the nucleic acid opposite it in a duplex. In some embodiments, the bulge is formed when the regions of complementary nucleic acids bind to each other, whereas the regions of central non-complementary region do not bind. In some embodiments, the bulge is formed when the two strands of nucleic acid positioned between the two complementary regions are of different lengths. As described below, a bulge may 1 or more nucleotides.

During miRNA processing, the miRNA is cleaved at a cleavage site adjacent to the guide strand:non-guide strand interface, thus releasing the siRNA duplex of the guide and non-guide strands. In some embodiments, the miRNA comprises a bulge in the sense or antisense strand adjacent to the cleavage site. To state another way, in some embodiments, the miRNA comprises a bulge in the guide or non-guide strand adjacent to the seed sequence. A bulge in this position is indicated by an arrow in the exemplary embodiment shown in FIG. 9B.

In some embodiments, the miRNA comprises a bulge in the guide strand opposite the 5' cleavage site of the mature non-guide strand. In some embodiments, the miRNA comprises a bulge opposite the 5' nucleotide of the non-guide strand. In some embodiments, the miRNA comprises a bulge in the sense strand opposite the 3' cleavage site of the mature guide strand. In some embodiments, the miRNA comprises a bulge opposite the 3' nucleotide of the guide strand.

In some embodiments, the RNAi comprises a first strand and a second strand, wherein a) the first strand and the second form a duplex; b) the first strand comprises a guide region of at least 11 bases, wherein the guide region comprises a seed region comprising bases 1–N of the guide strand, wherein N=7 or N=8; and c) the second strand comprises a non-guide region of at least 11 bases, wherein the non-guide region comprises a bulge sequence opposite of any one or more of bases 1–(N+2) of the guide region in the duplex. In some embodiments, wherein N=7 and the bulge is opposite base 1, 2, 3, 4, 5, 6, 7, 8, or 9 of the guide region. In other embodiments, N=8 and the bulge is opposite base 1, 2, 3, 4, 5, 6, 7, 8, 9, or 10 of the guide region.

In some embodiments, the RNAi comprises a first strand and a second strand, wherein a) the first strand and the second form a duplex; b) the first strand comprises a guide region of at least 10 bases, wherein the guide region comprises a seed region comprising bases 1–N of the guide strand, wherein N=7 or N=8; and c) the second strand comprises a non-guide region of at least 10 bases, wherein the non-guide region comprises a bulge sequence opposite of any one or more of bases 1–(N+1) of the guide region in the duplex. In some embodiments, wherein N=7 and the bulge is opposite base 1, 2, 3, 4, 5, 6, 7, or 8 of the guide region. In other embodiments, N=8 and the bulge is opposite base 1, 2, 3, 4, 5, 6, 7, 8, or 9 of the guide region.

In some embodiments, the non-guide region comprises a bulge sequence opposite of any one or more of bases 1–N of the guide region in the duplex. In some embodiments, N=7 and the bulge is opposite base 1, 2, 3, 4, 5, 6 or 7 of the guide region. In other embodiments, N=8 and the bulge is opposite base 1, 2, 3, 4, 5, 6, 7 or 8 of the guide region.

In some embodiments, the RNAi comprises a first strand and a second strand, wherein a) the first strand and the second form a duplex, b) the first strand comprises a guide region of at least 9 bases, wherein the guide region comprises a seed region comprising bases 2-7 or 2-8 of the guide strand, and c) the second strand comprises a non-guide region of at least 9 bases, wherein the non-guide region comprises a bulge sequence opposite of base 1 or base 9 of the guide region in the duplex.

In some embodiments, the RNAi comprises a first strand and a second strand, wherein a) the first strand and the second form a duplex, b) the first strand comprises a guide region of at least 9 bases, wherein the guide region comprises a seed region comprising bases 2-7 or 2-8 of the guide strand, and c) the second strand comprises a non-guide region of at least 9 bases, wherein the non-guide region comprises a bulge sequence opposite of base 1 of the guide region in the duplex.

In some embodiments, the bulge is formed by one or more bases of the non-guide strand in the duplex that lack a complementary base on the guide region, wherein the bulge is flanked by bases that do basepair with the guide strand. In some embodiments, the bulge sequence has about 1-10 nucleotides. In some embodiments, the bulge sequence has about 2-15 nucleotides. In some embodiments, the bulge sequence has about 1, about 2, about 3, about 4, about 5, about 6, about 7, about 8, about 9, about 10, about 11, about 12, about 13, about 14, or about 15 nucleotides.

The safety of RNAi-based therapies can be hampered by the ability of small inhibitory RNAs (siRNAs) to bind to unintended mRNAs and reduce their expression, an effect known as off-target gene silencing. Off-targeting primarily occurs when the seed region (nucleotides 2-8 of the small RNA) pairs with sequences in 3'-UTRs of unintended mRNAs and directs translational repression and destabilization of those transcripts. Reduced off-targeting RNAi may be designed by substituting bases within the guide and nonguide sequences; e.g., by creating CpG motifs. Potential substitutions that may result in a significantly lower off-target score can be evaluated using the SiSPOTR algorithm, a specificity-focused siRNA design algorithm which identifies candidate sequences with minimal off-targeting potentials and potent silencing capacities (Boudreau et al, *Nucleic Acids Res.* 2013 January; 41(1) e9. A reduced SiSPOTR score predicts sequences that have a lower number of potential human off targets compared parent RNAi molecules. In some embodiments of the invention, the RNAi is improved to reduce off-target gene silencing. In some embodiments, the RNAi comprises one or more CpG motifs. In some embodiments, the RNAi comprises one or more CpG motifs in a seed region.

In some embodiments, the first strand and the second strand are linked by means of a RNA (e.g., a RNA linker) capable of forming a loop structure. As is commonly known in the art, an RNA loop structure (e.g., a stem-loop or hairpin) is formed when an RNA molecule comprises two sequences of RNA that basepair together separated by a sequence of RNA that does not base pair together. For example, a loop structure may form in the RNA molecule A-B-C if sequences A and C are complementary or partially complementary such that they base pair together, but the bases in sequence B do not base pair together.

In some embodiments, the RNA capable of forming a loop structure comprises from 4 to 50 nucleotides. In certain embodiments, the RNA capable of forming a loop structure comprises 13 nucleotides. In some embodiments, the number of nucleotides in the RNA capable of forming a loop is from 4 to 50 nucleotides or any integer therebetween. In some embodiments, from 0-50% of the loop can be complementary to another portion of the loop. As used herein, the term "loop structure" is a sequence that joins two complementary strands of nucleic acid. In some embodiments, 1-3 nucleotides of the loop structure are contiguous to the complementary strands of nucleic acid and may be complementary to 1-3 nucleotides of the distal portion of the loop structure. For example, the three nucleotides at the 5' end of the loop structure may be complementary to the three nucleotides at the 3' end of the loop structure.

In some embodiments, nucleic acid encoding an RNAi of the present disclosure comprises a heterologous miRNA scaffold. In some embodiments, use of a heterologous miRNA scaffold is used to modulate miRNA expression; for example, to increase miRNA expression or to decrease miRNA expression. Any miRNA scaffold known in the art may be used. In some embodiments, the miRNA scaffold is derived from a miR-155 scaffold (see, e.g., Lagos-Quintana, M. et al. (2002) *Curr. Biol.* 12:735-9 and the Invitrogen™ BLOCK-iT™ Pol II miR RNAi expression vector kit from Life Technologies, Thermo Fisher Scientific; Waltham, Mass.).

IV. Huntington's Disease and Experimental Models Thereof

Huntington's disease (HD) is an inherited neurodegenerative disease caused by an expansion of the CAG repeat in exon 1 of the huntingtin gene (HTT). The resulting extension of the polyglutamine tract in the N-terminal region confers a toxic gain-of-function to the mutant huntingtin protein (mHtt). mHtt toxicity may arise from the formation of insoluble mHtt-containing aggregates, transcriptional dysregulation, and perturbations in protein homeostasis, all of which can lead to neuronal death (Saudou et al. (1998) *Cell,* 95:55-66; Zuccato et al. (2003) *Nat. Genet.* 35:76-83; Schaffar et al. (2004) *Mol. Cell.* 15:95-105; Benn et al., (2008) *J. Neurosci.* 28:10720-10733). Pathological findings in patients with HD include cortical thinning and a striking progressive loss of striatal neurons (Rosas et al., (2002) *Neurology* 58:695-701). Disease onset typically occurs during the third to fourth decade of life; symptoms include choreiform movements, impaired coordination, progressive dementia, and other psychiatric disturbances (Vonsattel et al., (1985) *J. Neuropathol. Exp. Neurol.* 44:559-577). In most cases, symptoms begin to appear between 30 and 40 years of age with subtle disruptions in motor skills, cognition, and personality. Over time, these progress into jerky, uncontrollable movements and loss of muscle control, dementia, and psychiatric illnesses such as depression, aggression, anxiety, and obsessive-compulsive behaviors. Death typically occurs 10-15 years after the onset of symptoms. Less than 10% of HD cases involve a juvenile-onset form of the disease, characterized by a faster disease progression. It is thought that approximately 1 in 10,000 Americans has HD.

Although the genetic basis of HD has been known for almost 20 years, current therapies are largely palliative and do not address the underlying cause of the disease. This is likely due in part to the fact that the etiology of this disease is complex, with detrimental effects observed in a wide variety of cellular processes. Hence, the focus of drug development has been directed at addressing the primary offending trigger, namely, the mutant HTT gene itself.

Most cases of HD are associated with a trinucleotide CAG repeat expansion in the HTT gene. The number of CAG repeats in the HTT gene is strongly correlated with the manifestation of HD. For example, individuals with 35 or fewer repeats typically do not develop HD, but individuals with between 27 and 35 repeats have a greater risk of having offspring with HD. Individuals with between 36 and 40-42 repeats have an incomplete penetrance of HD, whereas individuals with more than 40-42 repeats show complete penetrance. Cases of juvenile-onset HD may be associated with CAG repeat sizes of 60 or more.

The polyQ-expanded Htt protein resulting from this CAG repeat expansion is associated with cellular aggregates or inclusion bodies, perturbations to protein homeostasis, and transcriptional dysregulation. While these toxic phenotypes may be associated with several parts of the body, they are most typically associated with neuronal cell death. HD patients often display cortical thinning and a striking, progressive loss of striatal neurons. The striatum appears to be the most vulnerable region of the brain to HD (particularly the striatal medium spiny neurons), with early effects seen in the putamen and caudate nucleus. Cell death in the striatal spiny neurons, increased numbers of astrocytes, and activation of microglia are observed in the brains of HD patients. HD may also affect certain regions of the hippocampus, cerebral cortex, thalamus, hypothalamus, and cerebellum.

Proposed approaches to blocking Htt expression include the use of antisense oligonucleotides (ASOs) as well as RNA interference (RNAi) that uses either duplex RNAs (dsRNAs) or chemically modified single-stranded RNAs (ssRNAs) (Harper et al., (2005) *Proc. Natl. Acad. Sci. USA* 102:5820-5825; DiFiglia et al., (2007) *Proc. Natl. Acad. Sci. USA* 104:17204-17209; Boudreau et al., (2009b) *Mol. Ther.* 17:1053-1063; Drouet et al., (2009) *Ann. Neurol.* 65:276-285; Sah et al., (2011) *J. Clin. Invest.* 121:500-507; Matsui et al., (2012) *Drug Discov. Today* 17:443-450; Yu et al., (2012) *Cell* 150:895-908). However, hurdles to translating an ASO approach into the clinic may include the need to incorporate a device to facilitate repeated and chronic infusions of ASO into the CNS, and to the need to adequately distribute the drug to target regions in a large brain.

To circumvent these potential issues with ASO, employing AAV-mediated expression of an RNAi (e.g., siRNA), which offers the potential for increased safety, increased efficiency, and longer-lasting efficacy, may be advantageous. As HD patients express both mutant and wild-type Htt alleles, a majority of siRNA targeting sequences will likely degrade both alleles. However, non-allele-specific Htt silencing in HD mice has been shown to be well tolerated and can afford the same benefit as reducing mutant Htt alone (Boudreau et al., (2009b) *Mol. Ther.* 17:1053-1063; Drouet et al., (2009) *Ann. Neurol.* 65:276-285; Kordasiewicz et al., (2012) *Neuron* 74(6):1031-1044). Moreover, the partial and sustained suppression of wild-type Htt in the putamen of non-human primates following AAV-mediated RNAi reportedly did not have any untoward effects, which suggests that the adult brain can tolerate reduced levels of wild-type Htt (McBride et al., (2011) *Mol. Ther.* 19:2152-2162; Grondin et al., (2012) *Brain* 135:1197-1209).

Animal models of HD may be used to test potential therapeutic strategies, such as the compositions and methods of the present disclosure. Mouse models for HD are known in the art. These include mouse models with fragments of mutant HTT such as the R6/1 and N171-82Q HD mice (Harper et al., (2005) *Proc. Natl. Acad. Sci. USA* 102:5820-5825, Rodriguez-Lebron et al., (2005) *Mol. Ther.* 12:618-633, Machida et al., (2006) *Biochem. Biophys. Res. Commun.* 343:190-197). Another example of a mouse HD model described herein is the YAC128 mouse model. This model bears a yeast artificial chromosome (YAC) expressing a mutant human HTT gene with 128 CAG repeats, and YAC128 mice exhibit significant and widespread accumulation of Htt aggregates in the striatum by 12 months of age (Slow et al., (2003) *Hum. Mol. Genet.* 12:1555-1567, Pouladi et al., (2012) *Hum. Mol. Genet.* 21:2219-2232).

Other animal models for HD may also be used. For example, transgenic rat (von Horsten, S. et al. (2003) *Hum. Mol. Genet.* 12:617-24) and rhesus monkey (Yang, S. H. et al. (2008) *Nature* 453:921-4) models have been described. Non-genetic models are also known. These most often involve the use of excitotoxic compounds (such as quinolinic acid or kainic acid) or mitochondrial toxins (such as 3-nitropropionic acid and malonic acid) to induce striatal neuron cell death in rodents or non-human primates (for more description and references, see Ramaswamy, S. et al. (2007) *ILAR J.* 48:356-73).

V. Methods to Treat Huntington's Disease

In some aspects, the invention provides methods and compositions for treating Huntington's disease in a mammal comprising administering to the mammal a pharmaceutical composition of the present disclosure (e.g., a pharmaceutical composition comprising a viral particle of the present disclosure). In some aspects, the invention provides methods and compositions for inhibiting the expression of htt in a mammal with Huntington's disease comprising administering to the mammal a pharmaceutical composition of the present disclosure (e.g., a pharmaceutical composition comprising a viral particle of the present disclosure). In some aspects, the invention provides methods and compositions for inhibiting the accumulation of htt in a cell of a mammal with Huntington's disease comprising administering to the mammal a pharmaceutical composition of the present disclosure (e.g., a pharmaceutical composition comprising a viral particle of the present disclosure).

In some aspects, the invention provides methods and compositions for ameliorating a symptom of HD, comprising administration of an effective amount of recombinant viral particles comprising a vector encoding an RNAi of the present disclosure to the brain of a mammal. In some embodiments, the symptoms of HD include, but are not limited to, chorea, rigidity, uncontrollable body movements, loss of muscle control, lack of coordination, restlessness, slowed eye movements, abnormal posturing, instability, ataxic gait, abnormal facial expression, speech problems, difficulties chewing and/or swallowing, disturbance of sleep, seizures, dementia, cognitive deficits (e.g., diminished abilities related to planning, abstract thought, flexibility, rule acquisition, interpersonal sensitivity, self-control, attention, learning, and memory), depression, anxiety, changes in personality, aggression, compulsive behavior, obsessive-compulsive behavior, hypersexuality, psychosis, apathy, irritability, suicidal thoughts, weight loss, muscle atrophy, heart failure, reduced glucose tolerance, testicular atrophy, and osteoporosis.

In some aspects, the invention provides methods to prevent or delay progression of HD. Autosomal dominant HD is a genetic disease that can be genotyped. For example, the number of CAG repeats in HTT may be determined by PCR-based repeat sizing. This type of diagnosis may be performed at any stage of life through directly testing juveniles or adults (e.g., along with presentation of clinical symptoms), prenatal screening or prenatal exclusion testing (e.g., by chorionic villus sampling or amniocentesis), or preimplantation screening of embryos. As such, the methods described herein may be used as a prophylactic treatment of HD since diagnosis may occur before symptom onset. For example, HD may be diagnosed by genetic testing (prenatal testing, testing at birth, etc.) and treated prophylactically (e.g., using a rAAV particle described herein) prior to symptom onset (e.g., CNS cell loss) to prevent HD symptom onset and/or progression. Additionally, HD may be diagnosed by brain imaging, looking for shrinkage of the caudate nuclei and/or putamen and/or enlarged ventricles. These symptoms, combined with a family history of HD and/or clinical symptoms, may indicate HD.

Means for determining amelioration of the symptoms of HD are known in the art. For example, the Unified Huntington's Disease Rating Scale (UHDRS) may be used to assess motor function, cognitive function, behavioral abnormalities, and functional capacity (see, e.g., Huntington Study Group (1996) *Movement Disorders* 11:136-42). This rating scale was developed to provide a uniform, comprehensive test for multiple facets of the disease pathology, incorporating elements from tests such as the HD Activities and Daily Living Scale, Marsden and Quinn's chorea severity scale, the Physical Disability and Independence scales, the HD motor rating scale (HDMRS), the HD functional capacity scale (HDFCS), and the quantitated neurological exam (QNE). Other test useful for determining amelioration of HD symptoms may include without limitation the Montreal Cognitive Assessment, brain imaging (e.g., MRI), Category Fluency Test, Trail Making Test, Map Search, Stroop Word Reading Test, Speeded Tapping Task, and the Symbol Digit Modalities Test.

In some aspects of the invention, the methods and compositions are used for the treatment of humans with HD. As described above, HD is inherited in an autosomal dominant manner and caused by CAG repeat expansion in the HTT gene. Juvenile-onset HD is most often inherited from the paternal side. Huntington disease-like phenotypes have also been correlated with other genetic loci, such as HDL1, PRNP, HDL2, HDL3, and HDL4. It is thought that other genetic loci may modify the manifestation of HD symptoms, including mutations in the GRIN2A, GRIN2B, MSX1, GRIK2, and APOE genes.

In some aspects, the invention provides an improved RNAi for targeting htt mRNA in a mammal with Huntington's disease. In some embodiments, the RNAi comprises a first strand comprising a first nucleic acid comprising the sequence 5'-UAGACAAUGAUUCACACGGU-3' (SEQ ID NO:1) and a second strand comprising a second nucleic acid comprising the sequence 5'-ACCGUGUGUCAUUGUC-UAA-3' (SEQ ID NO:2), where the first strand and second strand form a duplex and wherein the A residue at residue 18 or residue 19 of SEQ ID NO:2 of the second strand does not form a basepair with a residue in the first strand. An RNAi described herein (e.g., as part of a rAAV vector) may find use, inter alia, in treating Huntington's disease.

In some embodiments of the invention, the RNAi is improved to reduce off-target gene silencing. In some embodiments, the RNAi comprises one or more CpG motifs. In some embodiments, the RNAi comprises one or more CpG motifs in a seed region.

In some embodiments the invention provides methods for treating Huntington's disease in a mammal comprising administering to the mammal an RNAi comprising a first strand comprising a first nucleic acid comprising the sequence 5'-UCGACAAUGAUUCACACGGU-3' (SEQ ID NO:15) and a second strand comprising a second nucleic acid comprising the sequence 5'-ACCGUGUGUCAUUGU-CGAA-3' (SEQ ID NO:16), wherein the A residue at residue 18 or residue 19 of the second strand does not form a basepair with a residue in the first strand. In some embodiments the invention provides methods for inhibiting the expression of htt in a mammal with Huntington's disease comprising administering to the mammal an RNAi comprising a first strand comprising a first nucleic acid comprising the sequence 5'-UCGACAAUGAUUCACACGGU-3' (SEQ ID NO:15) and a second strand comprising a second nucleic acid comprising the sequence 5'-ACCGUGUGUCAUUGU-CGAA-3' (SEQ ID NO:16), wherein the A residue at residue 18 or residue 19 of the second strand does not form a basepair with a residue in the first strand. In some embodiments the invention provides methods for inhibiting the accumulation of htt in a cell of a mammal with Huntington's disease comprising administering to the mammal an RNAi comprising a first strand comprising a first nucleic acid comprising the sequence 5'-UCGACAAUGAUUCA-CACGGU-3' (SEQ ID NO:15) and a second strand comprising a second nucleic acid comprising the sequence 5'-ACCGUGUGUCAUUGUCGAA-3' (SEQ ID NO:16), wherein the A residue at residue 18 or residue 19 of the second strand does not form a basepair with a residue in the first strand. In some embodiments, the first strand comprises a nucleic acid sequence having more than about any of 75%, 80%, 85%, 90%, 95%, 96%, 97%, 98% or 99% identity to SEQ ID NO:15 but maintains the CpG motif. In some embodiments, the second strand comprises a nucleic acid sequence having more than about any of 75%, 80%, 85%, 90%, 95%, 96%, 97%, 98% or 99% identity to SEQ ID NO:16 but maintains the CpG motif.

In some embodiments the invention provides methods for treating Huntington's disease in a mammal comprising administering to the mammal an RNAi comprising a first strand comprising a first nucleic acid comprising the sequence 5'-UAGACGAUGAUUCACACGGU-3' (SEQ ID NO:17) and a second strand comprising a second nucleic acid comprising the sequence 5'-ACCGUGUGUCAUCGU-CUAA-3' (SEQ ID NO:18), wherein the A residue at residue 18 or residue 19 of the second strand does not form a basepair with a residue in the first strand. In some embodiments the invention provides methods for inhibiting the expression of htt in a mammal with Huntington's disease comprising administering to the mammal an RNAi comprising a first strand comprising a first nucleic acid comprising the sequence 5'-UAGACGAUGAUUCACACGGU-3' (SEQ ID NO:17) and a second strand comprising a second nucleic acid comprising the sequence 5'-ACCGUGUGUCAUCGU-CUAA-3' (SEQ ID NO:18), wherein the A residue at residue 18 or residue 19 of the second strand does not form a basepair with a residue in the first strand. In some embodiments the invention provides methods for inhibiting the accumulation of htt in a cell of a mammal with Huntington's disease comprising administering to the mammal an RNAi comprising a first strand comprising a first nucleic acid comprising the sequence 5'-UAGACGAUGAUUCA-CACGGU-3' (SEQ ID NO:17) and a second strand comprising a second nucleic acid comprising the sequence 5'-ACCGUGUGUCAUCGUCUAA-3' (SEQ ID NO:18), wherein the A residue at residue 18 or residue 19 of the second strand does not form a basepair with a residue in the first strand. In some embodiments, the first strand comprises a nucleic acid sequence having more than about any of 75%, 80%, 85%, 90%, 95%, 96%, 97%, 98% or 99% identity to SEQ ID NO:17 but maintains the CpG motif. In some embodiments, the second strand comprises a nucleic acid sequence having more than about any of 75%, 80%, 85%, 90%, 95%, 96%, 97%, 98% or 99% identity to SEQ ID NO:18 but maintains the CpG motif.

In some embodiments, the RNAi is a small inhibitory RNA (siRNA), a microRNA (miRNA), or a small hairpin RNA (shRNA). A small inhibitory or interfering RNA (siRNA) is known in the art as a double-stranded RNA molecule of approximately 19-25 (e.g., 19-23) base pairs in length that induces RNAi in a cell. A small hairpin RNA (shRNA) is known in the art as an RNA molecule comprising approximately 19-25 (e.g., 19-23) base pairs of double stranded RNA linked by a short loop (e.g., ~4-11 nucleotides) that induces RNAi in a cell.

In some embodiments, the miRNA comprises a guide sequence that is about 90% identical to SEQ ID NO:1. In some embodiments, the miRNA comprises a guide sequence that is about any of 90% identical, 91% identical, 92% identical, 93% identical, 94% identical, 95% identical, 96% identical, 97% identical, 98% identical, 99% identical, or 100% identical to SEQ ID NO:1.

In some embodiments, the miRNA comprises a non-guide sequence that is about 90% identical to SEQ ID NO:2. In some embodiments, the miRNA comprises a non-guide sequence that is about any of 90% identical, 91% identical, 92% identical, 93% identical, 94% identical, 95% identical, 96% identical, 97% identical, 98% identical, 99% identical, or 100% identical to SEQ ID NO:2.

In some embodiments, U residues at residues 11 and 12 of SEQ ID NO:1 of the first nucleic acid do not form a basepair with a residue in the second strand. In some embodiments, the duplex is between 18 and 25 base pairs in length. In some embodiments, the first and/or second strand further comprises a 3' overhang region, a 5' overhang region, or both 3' and 5' overhang regions. In some embodiments, the invention provides RNAi, as well as methods and compositions for use thereof, comprising a first strand comprising a first nucleic acid comprising the sequence 5'-UAGA-CAAUGAUUCACACGGU-3' (SEQ ID NO:1) and a second strand comprising a second nucleic acid comprising the sequence 5'-ACCGUGUGUCAUUGUCUAA-3' (SEQ ID NO:2), where the first strand and second strand form a duplex and wherein the A residue at residue 18 or residue 19 of SEQ ID NO:2 does not form a basepair with a residue in the first strand and the U residues at residues 11 and 12 of SEQ ID NO:1 of the first nucleic acid do not form a basepair with a residue in the second strand.

In some embodiments, the first strand and the second strand are linked by means of RNA capable of forming a loop structure. As is commonly known in the art, an RNA loop structure (e.g., a stem-loop or hairpin) is formed when an RNA molecule comprises two sequences of RNA that basepair together separated by a sequence of RNA that does not base pair together. For example, a loop structure may form in the RNA molecule A-B-C if sequences A and C are complementary or partially complementary such that they base pair together, but the bases in sequence B do not base pair together.

In some embodiments, the RNA capable of forming a loop structure comprises from 4 to 50 nucleotides. In certain embodiments, the RNA capable of forming a loop structure comprises 13 nucleotides. In certain embodiments, the RNA capable of forming a loop structure comprises the nucleotide sequence of SEQ ID NO:7. In some embodiments, the vector genome comprises a nucleotide sequence that is at least about any of 80%, 85%, 90%, 91%, 92%, 93%, 94%, 95%, 96%, 97%, 98%, or 99% identical to the sequence of SEQ ID NO:13.

In some aspects, the invention provides methods comprising administering to a mammal (e.g., a mammal with HD) an RNAi comprising a first strand comprising a first nucleic acid comprising the sequence 5'-UAGA-CAAUGAUUCACACGGU-3' (SEQ ID NO:1) and a second strand comprising a second nucleic acid comprising the sequence 5'-ACCGUGUGUCAUUGUCUAA-3' (SEQ ID NO:2), where the A residue at residue 18 or residue 19 of the SEQ ID NO:2 does not form a basepair with a residue in the first strand. In some embodiments, the U residues at positions 11 and 12 of SEQ ID NO:1 of the first nucleic acid do not basepair with residues of the second strand. In some embodiments, the A residue at residue 18 or residue 19 of the SEQ ID NO:2 does not form a basepair with a residue in the first strand and the U residues at positions 11 and 12 of SEQ ID NO:1 of the first nucleic acid do not basepair with residues of the second strand. In some embodiments, a recombinant viral particle comprises the RNAi. In some embodiments, the recombinant viral particle is an AAV particle encapsidating a rAAV vector, an adenovirus particle encapsidating a recombinant adenoviral vector, a lentiviral particle encapsidating a recombinant lentiviral vector or an HSV particle encapsidating a recombinant HSV vector wherein the rAAV vector, the adenoviral vector, the lentiviral vector or the HSV vector encodes the RNAi.

In some embodiments, delivery of recombinant viral particles is by injection of viral particles to the brain. In some embodiments, delivery of recombinant viral particles is by injection of viral particles to the striatum. Intrastriatal administration delivers recombinant viral particles to an area of the brain, the striatum (including the putamen and caudate nucleus), that is highly affected by HD. In addition, and without wishing to be bound to theory, it is thought that recombinant viral particles (e.g., rAAV particles) injected into the striatum may be also dispersed (e.g., through retrograde transport) to other areas of the brain, including without limitation projection areas (e.g., the cortex). In some embodiments, the recombinant viral particles are delivered by convection enhanced delivery (e.g., convection enhanced delivery to the striatum).

In some aspects, the invention provides methods for treating Huntington's disease in a mammal comprising administering to the mammal the pharmaceutical composition of the present disclosure. In some aspects, the invention provides methods for inhibiting the accumulation of htt in a cell of a mammal with Huntington's disease comprising administering to the mammal the pharmaceutical composition of the present disclosure. In some aspects, the invention provides methods for inhibiting the expression of htt in a mammal with Huntington's disease comprising administering to the mammal the pharmaceutical composition of the present disclosure. In some embodiments, the htt is a mutant htt (e.g., an htt comprising greater than 35, greater than 36, greater than 37, greater than 38, greater than 39, greater than 40, greater than 41, or greater than 42 CAG repeats). In some embodiments, expression and/or accumulation of a wild-type htt is also inhibited. As described herein, and without wishing to be bound to theory, it is thought that inhibition of expression and/or accumulation of mutant htt in a mammal with HD is highly beneficial, but the inhibition of expression and/or accumulation of wild-type htt in the same mammal as a side effect (e.g., of an RNAi of the present disclosure) may be well tolerated (e.g., produces few or no unintended side effects).

In some embodiments, a cell comprises a vector (e.g., a vector comprising an expression construct encoding an RNAi of the present disclosure). In some embodiments, the vector is a rAAV vector. In some embodiments, the vector is a recombinant adenoviral vector, a recombinant lentiviral vector or a recombinant herpes simplex virus (HSV) vector. In some embodiments, the cell is a central nervous system (CNS) cell.

In some embodiments, the administration of an effective amount of recombinant viral particles comprising a vector encoding an RNAi of the present disclosure transduces neurons (e.g., striatal neurons, such as spiny neurons) at or near the site of administration. In some embodiments, more than about any of 5%, 10%, 15%, 20%, 25%, 30%, 35%, 40%, 45%, 50%, 55%, 60%, 65%, 70%, 75% or 100% of neurons are transduced. In some embodiments, about 5% to about 100%, about 10% to about 50%, about 10% to about 30%, about 25% to about 75%, about 25% to about 50%, or about 30% to about 50% of the neurons are transduced. Methods to identify neurons transduced by recombinant viral particles expressing miRNA are known in the art; for example, immunohistochemistry, RNA detection (e.g., qPCR, Northern blotting, RNA-seq, in situ hybridization, and the like) or the use of a co-expressed marker such as enhanced green fluorescent protein can be used to detect expression.

In some embodiments of the invention, the methods comprise administration to the brain of a mammal an effective amount of recombinant viral particles comprising a vector encoding an RNAi of the present disclosure for treating a mammal, e.g., a human, with HD. In some embodiments, the composition is injected to one or more locations in the brain to allow expression of an RNAi of the present disclosure in at least the neurons. In some embodiments, the composition is injected into any one of one, two, three, four, five, six, seven, eight, nine, ten or more than ten locations in the brain. In some embodiments, the composition is injected into the striatum. In some embodiments, the composition is injected into the dorsal striatum. In some embodiments, the composition is injected into the putamen. In some embodiments, the composition is injected into the caudate nucleus. In some embodiments, the composition is injected into the putamen and into the caudate nucleus.

In some embodiments, the recombinant viral particles are administered to one hemisphere of the brain. In some embodiments, the recombinant viral particles are administered to both hemispheres of the brain.

In some embodiments the recombinant viral particles are administered to more than one location simultaneously or sequentially. In some embodiment, multiple injections of recombinant viral particles are no more than one hour, two hours, three hours, four hours, five hours, six hours, nine hours, twelve hours or 24 hours apart.

In some embodiments, the invention provides a method for treating a human with HD by administering an effective amount of a pharmaceutical composition comprising a recombinant viral vector encoding an RNAi of the present disclosure to suppress the activity of a mutant HTT. In some embodiments, the pharmaceutical composition comprises one or more pharmaceutically acceptable excipients.

In some embodiments, the methods comprise administering an effective amount of a pharmaceutical composition comprising a recombinant viral vector encoding an RNAi of the present disclosure to suppress the activity of a mutant HTT. In some embodiments, the viral titer of the viral particles (e.g., rAAV particles) is at least about any of $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$, or $50\times10^{12}$ genome copies/mL. In some embodiments, the viral titer of the viral particles (e.g., rAAV particles) is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, $20\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL. In some embodiments, the viral titer of the viral particles (e.g., rAAV particles) is about any of $5\times10^{12}$ to $10\times10^{12}$, $10\times10^{12}$ to $25\times10^{12}$, or $25\times10^{12}$ to $50\times10^{12}$ genome copies/mL. In some embodiments, the viral titer of the viral particles (e.g., rAAV particles) is at least about any of $5\times10^{9}$, $6\times10^{9}$, $7\times10^{9}$, $8\times10^{9}$, $9\times10^{9}$, $10\times10^{9}$, $11\times10^{9}$, $15\times10^{9}$, $20\times10^{9}$, $25\times10^{9}$, $30\times10^{9}$, or $50\times10^{9}$ transducing units/mL. In some embodiments, the viral titer of the viral particles (e.g., rAAV particles) is about any of $5\times10^{9}$ to $6\times10^{9}$, $6\times10^{9}$ to $7\times10^{9}$, $7\times10^{9}$ to $8\times10^{9}$, $8\times10^{9}$ to $9\times10^{9}$, $9\times10^{9}$ to $10\times10^{9}$, $10\times10^{9}$ to $11\times10^{9}$, $11\times10^{9}$ to $15\times10^{9}$, $15\times10^{9}$ to $20\times10^{9}$, $20\times10^{9}$ to $25\times10^{9}$, $25\times10^{9}$ to $30\times10^{9}$, $30\times10^{9}$ to $50\times10^{9}$ or $50\times10^{9}$ to $100\times10^{9}$ transducing units/mL. In some embodiments, the viral titer of the viral particles (e.g., rAAV particles) is about any of $5\times10^{9}$ to $10\times10^{9}$, $10\times10^{9}$ to $15\times10^{9}$, $15\times10^{9}$ to $25\times10^{9}$, or $25\times10^{9}$ to $50\times10^{9}$ transducing units/mL. In some embodiments, the viral titer of the viral particles (e.g., rAAV particles) is at least any of about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$, $40\times10^{10}$, or $50\times10^{10}$ infectious units/mL. In some embodiments, the viral titer of the viral particles (e.g., rAAV particles) is at least any of about $5\times10^{10}$ to $6\times10^{10}$, $6\times10^{10}$ to $7\times10^{10}$, $7\times10^{10}$ to $8\times10^{10}$, $8\times10^{10}$ to $9\times10^{10}$, $9\times10^{10}$ to $10\times10^{10}$, $10\times10^{10}$ to $11\times10^{10}$, $11\times10^{10}$ to $15\times10^{10}$, $15\times10^{10}$ to $20\times10^{10}$, $20\times10^{10}$ to $25\times10^{10}$, $25\times10^{10}$ to $30\times10^{10}$, $30\times10^{10}$ to $40\times10^{10}$, $40\times10^{10}$ to $50\times10^{10}$, or $50\times10^{10}$ to $100\times10^{10}$ infectious units/mL. In some embodiments, the viral titer of the viral particles (e.g., rAAV particles) is at least any of about $5\times10^{10}$ to $10\times10^{10}$, $10\times10^{10}$ to $15\times10^{10}$, $15\times10^{10}$ to $25\times10^{10}$, or $25\times10^{10}$ to $50\times10^{10}$ infectious units/mL.

In some embodiments, the dose of viral particles administered to the individual is at least about any of $1\times10^{8}$ to about $1\times10^{13}$ genome copies/kg of body weight. In some embodiments, the dose of viral particles administered to the individual is about any of $1\times10^{8}$ to about $1\times10^{13}$ genome copies/kg of body weight.

In some embodiments, the total amount of viral particles administered to the individual is at least about any of $1\times10^{9}$ to about $1\times10^{14}$ genome copies. In some embodiments, the total amount of viral particles administered to the individual is about any of $1\times10^{9}$ to about $1\times10^{14}$ genome copies.

In some embodiments of the invention, the volume of the composition injected to the striatum is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

In some embodiments, a first volume of the composition is injected into a first region of the brain, and a second volume of the composition is injected into a second region of the brain. For example, in some embodiments, a first volume of the composition is injected into the caudate nucleus, and a second volume of the composition is injected into the putamen. In some embodiments, a 1× volume of the composition is injected into the caudate nucleus, and a 1.5×, 2×, 2.5×, 3×, 3.5×, or 4× volume of the composition is injected into the putamen, where X is a volume that is more than about any one of 1 µl, 2 µl, 3 µl, 4 µl, 5 µl, 6 µl, 7 µl, 8 μl, 9 μl, 10 μl, 15 μl, 20 μl, 25 μl, 50 μl, 75 μl, 100 μl, 200 μl, 300 μl, 400 μl, 500 μl, 600 μl, 700 μl, 800 μl, 900 μl, or 1 mL, or any amount therebetween.

Compositions of the invention (e.g., recombinant viral particles comprising a vector encoding an RNAi of the present disclosure) can be used either alone or in combination with one or more additional therapeutic agents for treating HD. The interval between sequential administration can be in terms of at least (or, alternatively, less than) minutes, hours, or days.

V. RNAi Expression Constructs and Vectors

The invention provides expression constructs, vectors and viral particles for expression of the RNAi described herein.

In some embodiments, nucleic acid encoding an RNAi of the present disclosure comprises a heterologous miRNA scaffold. In some embodiments, use of a heterologous miRNA scaffold is used to modulate miRNA expression; for example, to increase miRNA expression or to decrease miRNA expression. Any miRNA scaffold known in the art may be used. In some embodiments, the miRNA scaffold is derived from a miR-155 scaffold (see, e.g., Lagos-Quintana, M. et al. (2002) *Curr. Biol.* 12:735-9 and the Invitrogen™ BLOCK-iT™ Pol II miR RNAi expression vector kit from Life Technologies, Thermo Fisher Scientific; Waltham, Mass.). In some embodiments, nucleic acid encoding an RNAi of the present disclosure comprises a miRNA scaffold. In some embodiments, miRNA scaffold is provided by SEQ ID NO:14.

In some embodiments, the RNAi targets RNA encoding a polypeptide associated with a disorder. In some embodiments, the disorder is a CNS disorder. Without wishing to be bound by theory, it is thought that an RNAi may be used to reduce or eliminate the expression and/or activity of a polypeptide whose gain-of-function has been associated with a disorder. Non-limiting examples of CNS disorders of the invention that may be treated by a therapeutic polypeptide or therapeutic nucleic acid of the invention (exemplary genes that may be targeted or supplied are provided in parenthesis for each disorder) include stroke (e.g., caspase-3, Beclin1, Ask1, PAR1, HIF1α, PUMA, and/or any of the genes described in Fukuda, A. M. and Badaut, J. (2013) Genes (Basel) 4:435-456), Huntington's disease (mutant HTT), epilepsy (e.g., SCN1A, NMDAR, ADK, and/or any of the genes described in Boison, D. (2010) *Epilepsia* 51:1659-1668), Parkinson's disease (alpha-synuclein), Lou Gehrig's disease (also known as amyotrophic lateral sclerosis; SOD1), Alzheimer's disease (tau, amyloid precursor protein), corticobasal degeneration or CBD (tau), corticogasal ganglionic degeneration or CBGD (tau), frontotemporal dementia or FTD (tau), progressive supranuclear palsy or PSP (tau), multiple system atrophy or MSA (alpha-synuclein), cancer of the brain (e.g., a mutant or overexpressed oncogene implicated in brain cancer), and lysosomal storage diseases (LSD). Disorders of the invention may include those that involve large areas of the cortex, e.g., more than one functional area of the cortex, more than one lobe of the cortex, and/or the entire cortex. Other non-limiting examples of disorders of the invention that may be treated by a therapeutic polypeptide or therapeutic nucleic acid of the invention include traumatic brain injury, enzymatic dysfunction disorders, psychiatric disorders (including post-traumatic stress syndrome), neurodegenerative diseases, and cognitive disorders (including dementias, autism, and depression). Enzymatic dysfunction disorders include without limitation leukodystrophies (including Canavan's disease) and any of the lysosomal storage diseases described below.

In some embodiments, the transgene (e.g., an RNAi of the present disclosure) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene*, 1991, 108(2):193-9) and the elongation factor 1-alpha promoter (EF1-alpha) promoter (Kim et al., *Gene*, 1990, 91(2):217-23 and Guo et al., *Gene Ther.*, 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the invention provides a recombinant vector comprising nucleic acid encoding a heterologous transgene of the present disclosure operably linked to a CBA promoter. Exemplary promoters and descriptions may be found, e.g., in U.S. PG Pub. 20140335054. In some embodiments, the promoter is a CBA promoter, a minimum CBA promoter, a CMV promoter or a GUSB promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the 13-actin promoter, the phosphoglycerol kinase (PGK) promoter, and the EFla promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art.

Exemplary tissue-specific regulatory sequences include, but are not limited to the following tissue specific promoters: neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. IDSA, 88:5611-5 (1991)), and the neuron-specific vgf gene promoter (Piccioli et al., Neuron, 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). Other appropriate tissue specific promoters will be apparent to the skilled artisan. In some embodiments, the promoter is a chicken Beta-actin promoter.

In some embodiments, the promoter expresses the heterologous nucleic acid in a cell of the CNS. As such, in some embodiments, a therapeutic polypeptide or a therapeutic nucleic acid of the invention may be used to treat a disorder of the CNS. In some embodiments, the promoter expresses the heterologous nucleic acid in a brain cell. A brain cell may refer to any brain cell known in the art, including without limitation a neuron (such as a sensory neuron, motor neuron, interneuron, dopaminergic neuron, medium spiny neuron, cholinergic neuron, GABAergic neuron, pyramidal neuron, etc.), a glial cell (such as microglia, macroglia, astrocytes, oligodendrocytes, ependymal cells, radial glia, etc.), a brain parenchyma cell, microglial cell, ependemal cell, and/or a Purkinje cell. In some embodiments, the promoter expresses the heterologous nucleic acid in a neuron and/or glial cell. In some embodiments, the neuron is a medium spiny neuron of the caudate nucleus, a medium spiny neuron of the putamen, a neuron of the cortex layer IV and/or a neuron of the cortex layer V.

Various promoters that express transcripts (e.g., a heterologous transgene) in CNS cells, brain cells, neurons, and glial cells are known in the art and described herein. Such promoters can comprise control sequences normally associated with the selected gene or heterologous control sequences. Often, useful heterologous control sequences include those derived from sequences encoding mammalian or viral genes. Examples include, without limitation, the SV40 early promoter, mouse mammary tumor virus LTR promoter, adenovirus major late promoter (Ad MLP), a herpes simplex virus (HSV) promoter, a cytomegalovirus (CMV) promoter such as the CMV immediate early promoter recon (CMVIE), a rous sarcoma virus (RSV) promoter, synthetic promoters, hybrid promoters, and the like. In addition, sequences derived from nonviral genes, such as the murine metallothionein gene, may also be used. Such promoter sequences are commercially available from, e.g., Stratagene (San Diego, Calif.). CNS-specific promoters and inducible promoters may be used. Examples of CNS-specific promoters include without limitation those isolated from CNS-specific genes such as myelin basic protein (MBP), glial fibrillary acid protein (GFAP), and neuron specific enolase (NSE). Examples of inducible promoters include DNA responsive elements for ecdysone, tetracycline, metallothionein, and hypoxia, inter alia.

The present invention contemplates the use of a recombinant viral genome for introduction of one or more nucleic acid sequences encoding for a RNAi as described herein or packaging into an AAV viral particle. The recombinant viral genome may include any element to establish the expression of a RNAi, for example, a promoter, a heterologous nucleic acid, an ITR, a ribosome binding element, terminator, enhancer, selection marker, intron, polyA signal, and/or origin of replication. In some embodiments, the rAAV vector comprises one or more of an enhancer, a splice donor/splice acceptor pair, a matrix attachment site, or a polyadenylation signal.

In some embodiments, the administration of an effective amount of rAAV particles comprising a vector encoding a RNAi transduces cells (e.g., CNS cells, brain cells, neurons, and/or glial cells) at or near the site of administration (e.g., the striatum and/or cortex) or more distal to the site of administration. In some embodiments, more than about any of 5%, 10%, 15%, 20%, 25%, 30%, 35%, 40%, 45%, 50%, 55%, 60%, 65%, 70%, 75% or 100% of neurons are transduced. In some embodiments, about 5% to about 100%, about 10% to about 50%, about 10% to about 30%, about 25% to about 75%, about 25% to about 50%, or about 30% to about 50% of the neurons are transduced. Methods to identify neurons transduced by recombinant viral particles expressing miRNA are known in the art; for example, immunohistochemistry, RNA detection (e.g., qPCR, Northern blotting, RNA-seq, in situ hybridization, and the like) or the use of a co-expressed marker such as enhanced green fluorescent protein can be used to detect expression.

In some aspects, the invention provides viral particles comprising a recombinant self-complementing genome (e.g., a self-complementary rAAV vector). AAV viral particles with self-complementing vector genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) Gene Ther 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a heterologous nucleic acid). In some embodiments, the vector comprises first nucleic acid sequence encoding the heterologous nucleic acid and a second nucleic acid sequence encoding a complement of the nucleic acid, where the first nucleic acid sequence can form intrastrand base pairs with the second nucleic acid sequence along most or all of its length.

In some embodiments, the first heterologous nucleic acid sequence encoding a RNAi and a second heterologous nucleic acid sequence encoding the complement of the RNAi are linked by a mutated ITR (e.g., the right ITR). In some embodiments, the ITR comprises the polynucleotide sequence 5'-CACTCCCTCTCTGCGCGCTCGCTCGCT-CACTGAGGCC GGGCGACCAAAGGTCGCCCACGC-CCGGGCTTTGCCCGGGCG-3' (SEQ ID NO:12).

The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

VI. Viral Particles and Methods of Producing Viral Particles

The invention provides, inter alia, recombinant viral particles comprising a nucleic acid encoding an RNAi of the present disclosure, as well as methods of use thereof to treat a disease or disorder in a mammal; e.g., Huntington's disease.

Viral Particles

The invention provides viral particles comprising the RNAi as disclosed herein. In some embodiments, the invention provides viral particles for delivering the RNAi of the invention as disclosed herein. For example, the invention provides methods of using recombinant viral particles to deliver RNAi to treat a disease or disorder in a mammal; e.g., rAAV particles comprising RNAi to treat HD. In some embodiments, the recombinant viral particle is a recombinant AAV particle. In some embodiments, the viral particle is a recombinant AAV particle comprising a nucleic acid comprising a sequence an RNAi of the present disclosure flanked by one or two ITRs. The nucleic acid is encapsidated in the AAV particle. The AAV particle also comprises capsid proteins. In some embodiments, the nucleic acid comprises the coding sequence(s) of interest (e.g., nucleic acid an RNAi of the present disclosure) operatively linked components in the direction of transcription, control sequences including transcription initiation and termination sequences, thereby forming an expression cassette. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10): 6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV further encodes an RNAi as described herein. For example, the nucleic acid in the AAV can comprise at least one ITR of any AAV serotype contemplated herein and can further encode an RNAi comprising a first strand and a second strand, wherein a) the first strand and the second form a duplex; b) the first strand comprises a guide region of at least 11 bases, wherein the guide region comprises a seed region comprising bases 1–N of the guide strand, wherein N=7 or N=8; and c) the second strand comprises a non-guide region of at least 11 bases, wherein the non-guide region comprises a bulge sequence opposite of any one or more of bases 1–(N+2) of the guide region in the duplex. In some embodiments, the rAAV can comprise a first strand comprising a first nucleic acid comprising the sequence 5'-UAGACAAUGAUUCACACGGU-3' (SEQ ID NO:1) and a second strand comprising a second nucleic acid comprising the sequence 5'-ACCGUGUGUCAUUGUCUAA-3' (SEQ ID NO:2). In some embodiments, the nucleic acid in the AAV comprises 5' to 3' nucleic acid encoding the following: an ITR (e.g., an AAV2 ITR), a promoter, a nucleic acid encoding an RNAi as disclosed herein, a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a promoter, a nucleic acid encoding an RNAi comprising a first strand comprising a first nucleic acid comprising the sequence 5'-UAGACAAUGAUUCACACGGU-3' (SEQ ID NO:1) and a second strand comprising a second nucleic acid comprising the sequence 5'-ACCGUGUGUCAUUGUCUAA-3' (SEQ ID NO:2), a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a nucleic acid encoding an RNAi as disclosed herein, a polyadenylation signal (e.g., a bovine growth hormone polyA), and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a nucleic acid encoding an RNAi comprising a first strand comprising a first nucleic acid comprising the sequence 5'-UAGACAAUGAUUCACACGGU-3' (SEQ ID NO:1) and a second strand comprising a second nucleic acid comprising the sequence 5'-ACCGUGUGUCAUUGUC-UAA-3' (SEQ ID NO:2), a polyadenylation signal (e.g., a bovine growth hormone polyA), and an AAV ITR (e.g., an AAV2 ITR). In some embodiments, the first strand and second strand form a duplex, and the A residue at residue 18 or residue 19 of SEQ ID NO:2 of the second strand does not form a basepair with a residue in the first strand. In some embodiments, the U residues as residues 11 and 12 of SEQ ID NO:1 of the first strand do not form basepairs with the second strand. In some embodiments, the A residue at residue 18 or residue 19 of SEQ ID NO:2 of the second strand does not form a basepair with a residue in the first strand and the U residues as residues 11 and 12 of SEQ ID NO:1 of the first strand do not form basepairs with the second strand.

In some embodiments, a vector may include a stuffer nucleic acid. In some embodiments, the stuffer nucleic acid may encode a green fluorescent protein. In some embodiments, the stuffer nucleic acid may be located between the promoter and the nucleic acid encoding the RNAi. In some embodiments, the stuffer nucleic acid may be a human alpha-1-antitrypsin (AAT) stuffer sequence or a C16 P1 chromosome 16 P1 clone (human C16) stuffer sequence.

In some embodiments, the nucleic acid in the AAV comprises the nucleic acid of SEQ ID NO:13. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:13. In further embodiments, the rAAV particle comprises capsid proteins of AAV1, AAV2, AAV3, AAV4, AAV5, AA6, AAV7, AAV5, AAV5, AAVrh.8, AAVrh8R, AAVrh.10, AAV11, AAV12, or mutants of these capsid proteins. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105(22):7827-7832. In further embodiments, the rAAV particle comprises capsid proteins of an AAV serotype from Clades A-F (Gao, et al., *J. Virol.* 2004, 78(12):6381).

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, in some embodiments a rAAV particle can comprise AAV1 capsid proteins and at least one AAV2 ITR or it can comprise AAV2 capsid proteins and at least one AAV1 ITR. Any combination of AAV serotypes for production of a rAAV particle is provided herein as if each combination had been expressly stated herein. In some embodiments, the invention provides rAAV particles comprising an AAV1 capsid and a rAAV vector of the present disclosure (e.g., an expression cassette comprising nucleic acid encoding an RNAi of the present disclosure), flanked by at least one AAV2 ITR. In some embodiments, the invention provides rAAV particles comprising an AAV2 capsid.

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., an RNAi of the present disclosure) and a second heterologous polynucleotide sequence (e.g., antisense strand of an RNAi of the present disclosure) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in miRNA or siRNA molecules. In some embodiments, the first heterologous polynucleotide sequence and a second heterologous polynucleotide sequence are linked by a mutated ITR (e.g., the right ITR).

In some embodiments, the ITR comprises the polynucleotide sequence 5'-CACTCCCTCTCT-GCGCGCTCGCTCGCTCACTGAGGCCGGGCGAC-CAAAGGTCG CCCACGCCCGGGCTTTGCCCGGGCG-3' (SEQ ID NO:12). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the invention provides AAV viral particles comprising a recombinant viral genome comprising a functional AAV2 ITR, a first polynucleotide sequence encoding an RNAi of the present disclosure, a mutated AAV2 ITR comprising a deletion of the D region and lacking a functional terminal resolution sequence, a second polynucleotide sequence comprising the complementary sequence to the sequence encoding an RNAi of the present disclosure, of the first polynucleotide sequence and a functional AAV2 ITR.

In some embodiments, the viral particle is an adenoviral particle. In some embodiments, the adenoviral particle is a recombinant adenoviral particle, e.g., a polynucleotide vector comprising an RNAi of the present disclosure between two ITRs. In some embodiments, the adenoviral particle lacks or contains a defective copy of one or more E1 genes, which renders the adenovirus replication-defective. Adenoviruses include a linear, double-stranded DNA genome within a large (~950A), non-enveloped icosahedral capsid. Adenoviruses have a large genome that can incorporate more than 30 kb of heterologous sequence (e.g., in place of the E1 and/or E3 region), making them uniquely suited for use with larger heterologous genes. They are also known to infect dividing and non-dividing cells and do not naturally integrate into the host genome (although hybrid variants may possess this ability). In some embodiments, the adenoviral vector may be a first generation adenoviral vector with a heterologous sequence in place of E1. In some embodiments, the adenoviral vector may be a second generation adenoviral vector with additional mutations or deletions in E2A, E2B, and/or E4. In some embodiments, the adenoviral vector may be a third generation or gutted adenoviral vector that lacks all viral coding genes, retaining only the ITRs and packaging signal and requiring a helper adenovirus in trans for replication, and packaging. Adenoviral particles have been investigated for use as vectors for transient transfection of mammalian cells as well as gene therapy vectors. For further description, see, e.g., Danthinne, X. and Imperiale, M. J. (2000) *Gene Ther.* 7:1707-14 and Tatsis, N. and Ertl, H. C. (2004) *Mol. Ther.* 10:616-29.

In some embodiments, the viral particle is a recombinant adenoviral particle comprising a nucleic acid encoding an RNAi of the present disclosure. Use of any adenovirus serotype is considered within the scope of the present invention. In some embodiments, the recombinant adenoviral vector is a vector derived from an adenovirus serotype, including without limitation, AdHu2, AdHu 3, AdHu4, AdHu5, AdHu7, AdHu11, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, and porcine Ad type 3. The adenoviral particle also comprises capsid proteins. In some embodiments, the recombinant viral particles comprise an adenoviral particle in combination with one or more foreign viral capsid proteins. Such combinations may be referred to as pseudotyped recombinant adenoviral particles. In some embodiments, foreign viral capsid proteins used in pseudotyped recombinant adenoviral particles are derived from a foreign virus or from another adenovirus serotype. In some embodiments, the foreign viral capsid proteins are derived from, including without limitation, reovirus type 3. Examples of vector and capsid protein combinations used in pseudotyped adenovirus particles can be found in the following references (Tatsis, N. et al. (2004) *Mol. Ther.* 10(4): 616-629 and Ahi, Y. et al. (2011) *Curr. Gene Ther.* 11(4): 307-320). Different adenovirus serotypes can be used to optimize transduction of particular target cells or to target specific cell types within a particular target tissue (e.g., a diseased tissue). Tissues or cells targeted by specific adenovirus serotypes, include without limitation, lung (e.g. HuAd3), spleen and liver (e.g. HuAd37), smooth muscle, synoviocytes, dendritic cells, cardiovascular cells, tumor cell lines (e.g. HuAd11), and dendritic cells (e.g. HuAd5 pseudotyped with reovirus type 3, HuAd30, or HuAd35). For further description, see Ahi, Y. et al. (2011) *Curr. Gene Ther.* 11(4):307-320, Kay, M. et al. (2001) *Nat. Med.* 7(1): 33-40, and Tatsis, N. et al. (2004) *Mol. Ther.* 10(4):616-629. Adenoviral vectors have been administered by intrastriatal administration (see, e.g., Mittoux, V. et al. (2002) *J. Neurosci.* 22:4478-86).

In some embodiments, the viral particle is a lentiviral particle. In some embodiments, the lentiviral particle is a recombinant lentiviral particle, e.g., a polynucleotide vector encoding an RNAi of the present disclosure between two LTRs. Lentiviruses are positive-sense, ssRNA retroviruses with a genome of approximately 10 kb. Lentiviruses are known to integrate into the genome of dividing and nondividing cells. Lentiviral particles may be produced, for example, by transfecting multiple plasmids (typically the lentiviral genome and the genes required for replication and/or packaging are separated to prevent viral replication) into a packaging cell line, which packages the modified lentiviral genome into lentiviral particles. In some embodiments, a lentiviral particle may refer to a first generation vector that lacks the envelope protein. In some embodiments, a lentiviral particle may refer to a second generation vector that lacks all genes except the gag/pol and tat/rev regions. In some embodiments, a lentiviral particle may refer to a third generation vector that only contains the endogenous rev, gag, and pol genes and has a chimeric LTR for transduction without the tat gene (see Dull, T. et al. (1998) *J. Virol.* 72:8463-71). For further description, see Durand, S. and Cimarelli, A. (2011) *Viruses* 3:132-59.

In some embodiments, the viral particle is a recombinant lentiviral particle comprising a nucleic acid encoding an RNAi of the present disclosure. Use of any lentiviral vector is considered within the scope of the present invention. In some embodiments, the lentiviral vector is derived from a lentivirus including, without limitation, human immunodeficiency virus-1 (HIV-1), human immunodeficiency virus-2 (HIV-2), simian immunodeficiency virus (SIV), feline immunodeficiency virus (FIV), equine infectious anemia virus (EIAV), bovine immunodeficiency virus (BIV), Jembrana disease virus (JDV), visna virus (VV), and caprine arthritis encephalitis virus (CAEV). The lentiviral particle also comprises capsid proteins. In some embodiments, the recombinant lentiviral particles comprise a lentivirus vector in combination with one or more foreign viral capsid proteins. Such combinations may be referred to as pseudotyped recombinant lentiviral particles. In some embodiments, foreign viral capsid proteins used in pseudotyped recombinant lentiviral particles are derived from a foreign virus. In some embodiments, the foreign viral capsid protein used in pseudotyped recombinant lentiviral particles is Vesicular stomatitis virus glycoprotein (VSV-GP). VSV-GP interacts with a ubiquitous cell receptor, providing broad tissue tropism to pseudotyped recombinant lentiviral particles. In addition, VSV-GP is thought to provide higher stability to pseudotyped recombinant lentiviral particles. In other embodiments, the foreign viral capsid proteins are derived from, including without limitation, Chandipura virus, Rabies virus, Mokola virus, Lymphocytic choriomeningitis virus (LCMV), Ross River virus (RRV), Sindbis virus, Semliki Forest virus (SFV), Venezuelan equine encephalitis virus, Ebola virus Reston, Ebola virus Zaire, Marburg virus, Lassa virus, Avian leukosis virus (ALV), Jaagsiekte sheep retrovirus (JSRV), Moloney Murine leukemia virus (MLV), Gibbon ape leukemia virus (GALV), Feline endogenous retrovirus (RD114), Human T-lymphotropic virus 1 (HTLV-1), Human foamy virus, Maedi-visna virus (MVV), SARS-CoV, Sendai virus, Respiratory syncytia virus (RSV), Human parainfluenza virus type 3, Hepatitis C virus (HCV), Influenza virus, Fowl plague virus (FPV), or *Autographa californica* multiple nucleopolyhedro virus (AcMNPV). Examples of vector and capsid protein combinations used in pseudotyped Lentivirus particles can be found, for example, in Cronin, J. et al. (2005). *Curr. Gene Ther.* 5(4):387-398. Different pseudotyped recombinant lentiviral particles can be used to optimize transduction of particular target cells or to target specific cell types within a particular target tissue (e.g., a diseased tissue). For example, tissues targeted by specific pseudotyped recombinant lentiviral particles, include without limitation, liver (e.g. pseudotyped with a VSV-G, LCMV, RRV, or SeV F protein), lung (e.g. pseudotyped with an Ebola, Marburg, SeV F and HN, or JSRV protein), pancreatic islet cells (e.g. pseudotyped with an LCMV protein), central nervous system (e.g. pseudotyped with a VSV-G, LCMV, Rabies, or Mokola protein), retina (e.g. pseudotyped with a VSV-G or Mokola protein), monocytes or muscle (e.g. pseudotyped with a Mokola or Ebola protein), hematopoietic system (e.g. pseudotyped with an RD114 or GALV protein), or cancer cells (e.g. pseudotyped with a GALV or LCMV protein). For further description, see Cronin, J. et al. (2005). *Curr. Gene Ther.* 5(4):387-398 and Kay, M. et al. (2001) *Nat. Med.* 7(1):33-40.

In some embodiments, the viral particle is a herpes simplex virus (HSV) particle. In some embodiments, the HSV particle is a rHSV particle, e.g., a polynucleotide vector encoding an RNAi of the present disclosure between two TRs. HSV is an enveloped, double-stranded DNA virus with a genome of approximately 152 kb. Advantageously, approximately half of its genes are nonessential and may be deleted to accommodate heterologous sequence. HSV particles infect non-dividing cells. In addition, they naturally establish latency in neurons, travel by retrograde transport, and can be transferred across synapses, making them advantageous for transfection of neurons and/or gene therapy approaches involving the nervous system. In some embodiments, the HSV particle may be replication-defective or replication-competent (e.g., competent for a single replication cycle through inactivation of one or more late genes). For further description, see Manservigi, R. et al. (2010) *Open Virol. J.* 4:123-56.

In some embodiments, the viral particle is a rHSV particle comprising a nucleic acid encoding an RNAi of the present disclosure. Use of any HSV vector is considered within the scope of the present invention. In some embodiments, the HSV vector is derived from a HSV serotype, including without limitation, HSV-1 and HSV-2. The HSV particle also comprises capsid proteins. In some embodiments, the recombinant viral particles comprise a HSV vector in combination with one or more foreign viral capsid proteins. Such combinations may be referred to as pseudotyped rHSV particles. In some embodiments, foreign viral capsid proteins used in pseudotyped rHSV particles are derived from a foreign virus or from another HSV serotype. In some embodiments, the foreign viral capsid protein used in a pseudotyped rHSV particle is a Vesicular stomatitis virus glycoprotein (VSV-GP). VSV-GP interacts with a ubiquitous cell receptor, providing broad tissue tropism to pseudotyped rHSV particles. In addition, VSV-GP is thought to provide higher stability to pseudotyped rHSV particles. In other embodiments, the foreign viral capsid protein may be from a different HSV serotype. For example, an HSV-1 vector may contain one or more HSV-2 capsid proteins. Different HSV serotypes can be used to optimize transduction of particular target cells or to target specific cell types within a particular target tissue (e.g., a diseased tissue). Tissues or cells targeted by specific adenovirus serotypes include without limitation, central nervous system and neurons (e.g. HSV-1). For further description, see Manservigi, R. et al. (2010) *Open Virol J* 4:123-156, Kay, M. et al. (2001) *Nat. Med.* 7(1):33-40, and Meignier, B. et al. (1987) *J. Infect. Dis.* 155(5):921-930.

Production of Viral Particles rAAV particles can be produced using methods known in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

Methods known in the art for production of rAAV vectors include but are not limited to transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a nucleic acid (such as a therapeutic nucleic acid) flanked by at least one AAV ITR sequences; and 5) suitable media and media components to support rAAV production. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provided by baculovirus and the host cell is an insect cell (e.g., *Spodoptera frugiperda* (Sf9) cells).

In some embodiments, rAAV particles may be produced by a triple transfection method, such as the exemplary triple transfection method provided infra. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified. As such, in some embodiments, the rAAV particle was produced by triple transfection of a nucleic acid encoding the rAAV vector, a nucleic acid encoding AAV rep and cap, and a nucleic acid encoding AAV helper virus functions into a host cell, wherein the transfection of the nucleic acids to the host cells generates a host cell capable of producing rAAV particles.

In some embodiments, rAAV particles may be produced by a producer cell line method, such as the exemplary producer cell line method provided infra (see also (referenced in Martin et al., (2013) *Human Gene Therapy Methods* 24:253-269). Briefly, a cell line (e.g., a HeLa cell line) may be stably transfected with a plasmid containing a rep gene, a capsid gene, and a promoter-heterologous nucleic acid sequence. Cell lines may be screened to select a lead clone for rAAV production, which may then be expanded to a production bioreactor and infected with an adenovirus (e.g., a wild-type adenovirus) as helper to initiate rAAV production. Virus may subsequently be harvested, adenovirus may be inactivated (e.g., by heat) and/or removed, and the rAAV particles may be purified. As such, in some embodiments, the rAAV particle was produced by a producer cell line comprising one or more of nucleic acid encoding the rAAV vector, a nucleic acid encoding AAV rep and cap, and a nucleic acid encoding AAV helper virus functions.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) an rAAV pro-vector comprising a nucleic acid encoding an RNAi of the present disclosure as described herein flanked by at least one AAV ITR, and (iii) an AAV helper function; and (b) recovering the rAAV particles produced by the host cell. In some embodiments, the RNAi comprises the nucleotide sequence of SEQ ID NO:7. In some embodiments, said at least one AAV ITR is selected from the group consisting of AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, said encapsidation protein is selected from the group consisting of AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub.

2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, or an AAV capsid described in U.S. Pat. No. 8,283,151 or International Publication No. WO/2003/042397. In some embodiments, a mutant capsid protein maintains the ability to form an AAV capsid. In some embodiments, the encapsidation protein is an AAV5 tyrosine mutant capsid protein. In further embodiments, the rAAV particle comprises capsid proteins of an AAV serotype from Clades A-F. In some embodiments, the rAAV particles comprise an AAV1 capsid and a recombinant genome comprising AAV2 ITRs, a mutant AAV2 ITR and nucleic acid encoding an RNAi of the present disclosure. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Numerous methods are known in the art for production of adenoviral vector particles. For example, for a gutted adenoviral vector, the adenoviral vector genome and a helper adenovirus genome may be transfected into a packaging cell line (e.g., a 293 cell line).

In some embodiments, the helper adenovirus genome may contain recombination sites flanking its packaging signal, and both genomes may be transfected into a packaging cell line that expresses a recombinase (e.g., the Cre/loxP system may be used), such that the adenoviral vector of interest is packaged more efficiently than the helper adenovirus (see, e.g., Alba, R. et al. (2005) *Gene Ther.* 12 Suppl 1:S18-27). Adenoviral vectors may be harvested and purified using standard methods, such as those described herein.

Numerous methods are known in the art for production of lentiviral vector particles. For example, for a third-generation lentiviral vector, a vector containing the lentiviral genome of interest with gag and pol genes may be co-transfected into a packaging cell line (e.g., a 293 cell line) along with a vector containing a rev gene. The lentiviral genome of interest also contains a chimeric LTR that promotes transcription in the absence of Tat (see Dull, T. et al. (1998) *J. Virol.* 72:8463-71). Lentiviral vectors may be harvested and purified using methods (e.g., Segura M M, et al., (2013) *Expert Opin Biol Ther.* 13(7):987-1011) described herein.

Numerous methods are known in the art for production of HSV particles. HSV vectors may be harvested and purified using standard methods, such as those described herein. For example, for a replication-defective HSV vector, an HSV genome of interest that lacks all of the immediate early (IE) genes may be transfected into a complementing cell line that provides genes required for virus production, such as ICP4, ICP27, and ICP0 (see, e.g., Samaniego, L. A. et al. (1998) *J. Virol.* 72:3307-20). HSV vectors may be harvested and purified using methods described (e.g., Goins, W F et al., (2014) Herpes Simplex Virus Methods in Molecular Biology 1144:63-79).

Also provided herein are pharmaceutical compositions comprising a recombinant viral particle comprising a transgene encoding an RNAi of the present disclosure and a pharmaceutically acceptable carrier. The pharmaceutical compositions may be suitable for any mode of administration described herein. A pharmaceutical composition of a recombinant viral particle comprising a nucleic acid encoding an RNAi of the present disclosure can be introduced to the brain. For example, a recombinant viral particle comprising a nucleic acid encoding an RNAi of the present disclosure can be administered intrastriatally. Any of the recombinant viral particles of the present disclosure may be used, including rAAV, adenoviral, lentiviral, and HSV particles.

In some embodiments, the pharmaceutical compositions comprising a recombinant viral particle comprising a transgene encoding an RNAi of the present disclosure described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for injection into the brain of a mammal (e.g., intrastriatal administration). In some embodiments, the pharmaceutical compositions comprising a recombinant lentiviral particle described herein and a pharmaceutically acceptable carrier is suitable for injection into the brain of a mammal (e.g., intrastriatal administration). In some embodiments, the pharmaceutical compositions comprising a recombinant adenoviral particle described herein and a pharmaceutically acceptable carrier is suitable for injection into the brain of a mammal (e.g., intrastriatal administration). In some embodiments, the pharmaceutical compositions comprising a recombinant HSV particle described herein and a pharmaceutically acceptable carrier is suitable for injection into the brain of a mammal (e.g., intrastriatal administration).

Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VII. Articles of Manufacture and Kits

Also provided are kits or articles of manufacture for use in the methods described herein. In aspects, the kits comprise the compositions described herein (e.g., a recombinant viral particle of the present disclosure, such as a rAAV particle comprising nucleic acid encoding an RNAi of the present disclosure) in suitable packaging. Suitable packaging for compositions (such as intrastriatal compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein. For example, in some embodiments, the kit comprises a composition of recombinant viral particles comprising a transgene encoding an RNAi of the present disclosure for delivery of at least $1 \times 10^9$ genome copies into the brain of a mammal (e.g., through intrastriatal administration) to a primate as described herein, a pharmaceutically acceptable carrier suitable for injection into the brain of a primate, and one or more of: a buffer, a diluent, a filter, a needle, a syringe, and a package insert with instructions for performing injections into the brain of a primate (e.g., intrastriatal administration). In some embodiments, the kit comprising instructions for treating Huntington's disease with the recombinant viral particles described herein. In some embodiments, the kit comprising instructions for using the recombinant viral particles described herein according to any one of the methods described herein.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: AAV2/1-miRNA-Htt Reduces Htt Expression In Vitro

Huntington's disease (HD) is a fatal autosomal dominant neurodegenerative disease caused by an increase in the number of polyglutamine residues in the huntingtin (Htt) protein. With the identification of the underlying basis of HD, therapies are being developed that reduce the expression of the causative mutant Htt. RNA interference (RNAi) that seeks to selectively reduce the expression of such disease-causing agents is emerging as a potential therapeutic strategy for this and similar disorders. In order to examine the merits of RNAi therapy in a mouse model of HD, a targeting sequence that was previously shown to effectively target mouse and human Htt mRNAs (McBride et al., (2008) *Proc. Natl. Acad. Sci. USA* 105:5868-5873) was embedded into an artificial miRNA backbone and cloned into a previral vector.

Methods
Animals

All procedures were performed using a protocol approved by the Institutional Animal Care and Use Committee at Genzyme, a Sanofi Company (Department of Health and Human Services, NIH Publication 86-23). Mice used included YAC128 mice (a yeast artificial chromosome harboring the full-length human mutant HTT transgene with 128 CAG repeats on a pure FVB/NJ background) and FVB/NJ littermate mice (Slow et al., (2003) *Hum. Mol. Genet.* 12:1555-1567; Van Raamsdonk et al., (2005) *Hum. Mol. Genet.* 3823-3835). Both the YAC128 mice and FVB/NJ littermates were obtained from a Genzyme colony that was housed at the Charles River Laboratories. The mice were maintained on a 12 h light/dark cycle with food and water available ad libitum. All behavioral testing was performed during the animals' light cycle (between the hours of 8 am and 4 pm).

Plasmids and Viral Vectors

To generate recombinant AAV2/1 serotype vectors encoding a miRNA-based hairpin against the huntingtin gene (AAV2/1-miRNA-Htt), the miRNA for human HTT was cloned into a shuttle plasmid containing the AAV2 inverted terminal repeats (ITR), the bovine growth hormone polyA, and the 1.6-kb cytomegalovirus enhancer/chicken β-actin (CBA) promoter. The scaffold for the miRNA was from the Invitrogen™ BLOCK-iT™ Pol II miR RNAi expression vector kit (Life Technologies, Thermo Fisher Scientific; Waltham, Mass.). Control vectors contained either an empty vector backbone (AAV2/1-Null) or expressed an enhanced green fluorescent protein under the control of the same promoter (AAV2/1-eGFP). All viral vectors were generated by the triple-plasmid co-transfection of human 293 cells as previously described (Xiao et al. (1998) *J. Virol.* 72:2224-2232), and the recombinant virions were column purified as previously described (Passini et al., (2001) *J. Virol.* 75:12382-12392). The resulting titer of AAV2/1-miRNA-Htt was determined to be $4.5 \times 10^{12}$ vg/ml, and the titer of AAV2/1-Null was $2.3 \times 10^{12}$ vg/ml using quantitative PCR.

Surgical Procedures

Animals were anesthetized using 3% isofluorane and placed into a stereotaxic frame. Intracranial injections were performed as previously described (Treleaven, C. M. et al. (2012) *Mol. Ther.* 20:1713-1723). Briefly, 2 µl of the recombinant viral vectors (AAV2/1-eGFP or AAV2/1-miRNA-Htt) were injected into the striatum (AP, +0.50; ML, ±2.00; DV, −2.5 from bregma and dura; incisor bar, 0.0) using a 10 µl Hamilton syringe at the rate of 0.5 µl/min. The needle was left in place for 1 min following the completion of infusion. One hour before surgery and for 24 h following surgery, the mice were administered ketoprofen (5 mg/kg) subcutaneously for analgesia.

Animal Perfusion and Tissue Collection

The mice were perfused through the heart with phosphate-buffered saline (PBS) to remove all blood. The brains were cut sagittally along the midline, and the left hemisphere was post-fixed in 4% paraformaldehyde followed by 30% sucrose and then sectioned into 20-lam sections using a cryostat. The right hemisphere was cut along the coronal axis into 2-mm slabs using a mouse brain matrix (Harvard Apparatus, Holliston, Mass.) and then flash-frozen in liquid nitrogen and stored at −80° C. until use. For the analysis of Htt aggregates, the brains were post-fixed in 4% paraformaldehyde for 48 h, washed with PBS, and then sectioned into 40-µm coronal sections using a vibratome.

Cell Culture and Transfection

HEK293 cells were infected with 5×109 vg of either AAV2/1-eGFP or AAV2/1-miRNA-Htt and harvested 3 days later. RNA levels were measured by quantitative real-time RT-PCR. Total RNA was isolated using the TaqMan® Cells-to-CT™ Kit (Ambion). Q-PCR reactions were conducted and analyzed on an ABI Prism 7500 Sequence Detector (Applied Biosystems) as described previously (Kordasiewicz, H. B. et al. (2012) *Neuron* 74:1031-1044). Expression levels were normalized to PPIA (peptidylprolyl isomerase) levels.

Quantitative Real-Time PCR (TaqMan)

RNA levels were measured by quantitative real-time RT-PCR. Brain tissue samples from brain slab 2 were used for all RT-PCR analysis. Total RNA was extracted using the QIAGEN RNEasy mini kit and then reverse transcribed and amplified using the TaqMan® One-Step RT-PCR Master Mix Kit (Applied Biosystems) according to the manufacturer's instructions. For detecting mouse Htt mRNA, the following probe set was used: Mm01213820_m1 (Life Technologies Cat. No. 4331182). For detecting human Htt mRNA, the following oligos were used: 5'-ctccgtccggtaga-catgct-3' (forward primer, SEQ ID NO:9); 5'-ggaaatcagaac-cctcaaatgg-3' (reverse primer, SEQ ID NO:10); and 5'-tgag-cactgttcaactgtgtgtatcggga-3' (probe, SEQ ID NO:11). Quantitative RT-PCR reactions were conducted and analyzed on an ABI PRISM® 7500 Real Time PCR System (Applied Biosystems). The expression levels of Htt mRNA were normalized to hypoxanthine guanine phosphoribosyl transferase 1 (Hprt1) mRNA levels. Standard curves were generated using 5-fold serial dilutions of mouse brain cDNA. Each sample was run in duplicate. The relative gene expression was determined by using the standard curve or ΔΔCT method and normalizing to Hprt1 mRNA levels.

Western Blotting

Tissues were homogenized at a final concentration of 50 mg/ml in T-Per lysis buffer (Pierce) and containing the complete protease inhibitor cocktail (Roche). The homogenates were cleared by centrifugation at 10,000×g for 6 min at 4 C. The protein concentration was measured by using BSA assay (Pierce). Twenty to thirty micrograms of the homogenates was resolved on a 3-8% Novex tris-acetate gel and then transferred to a nitrocellulose membrane. The membranes were probed with a mouse anti-huntingtin monoclonal antibody (Mab2166; 1:2,000 dilution, Millipore) and rabbit polyclonal anti-β-tubulin antibody (1:750 dilution, Santa Cruz Biotechnology). The membranes were then incubated with infrared secondary antibodies (1:20,000 dilution, Rockland), and the proteins were visualized by quantitative fluorescence using Odyssey (LI-COR Biosciences). To control for loading variances, Htt protein was normalized to β-tubulin and expressed as a percentage of untreated or saline-treated animals. Molecular weight markers were used to verify the identity of the proteins.

Flow Cytometry and Cell Sorting (FCM Cell Sorting)

Single-cell suspensions were analyzed and isolated using the FACS Aria II cell sorter (BD Biosciences San Jose, Calif.) with a 100 μm nozzle at the Genzyme Flow Cytometry Core Facility (a Sanofi Company). Analysis of cells was performed by discriminating live single cells from debris by gating on the Forward Scatter (FWD-Sc) and Side Scatter (SSC). EGFP positive cells were collected using detector E with a 530/30 BP filter 505LP. EGFP fluorescence data profile was displayed as a single parameter histogram and sorting decisions were based on EGFP⁻ and EGFP⁺. Sorted cells were collected in tissue culture medium containing 5% fetal bovine serum and plated onto 4 well-chambered slides (LabTek, Nalge Nunc International, Naperville, Ill.) at a concentration of 50 000 cells/well.

Immunohistochemistry

Vibratome sections were processed for immunostaining by EM48, an antibody that preferentially recognizes aggregated huntingtin (Gutekunst et al., (1999) *J. Neurosci.* 19:2522-2534). The free floating sections were first treated with Dual Endogenous Enzyme Block (Dako) for 30 min to block endogenous peroxidase activity. They were then washed with 0.01 M PBS (3 min) followed by three washes with 0.5% Triton X-100 in PBS 10 min each. Nonspecific sites were blocked by incubating the sections in Rodent Block M for 1 h at room temperature. Sections were probed with the EM48 antibody (Millipore, 1:25 dilution in PBS) by incubating at 4° C. cold room on a gentle rocker overnight. The next day, sections were incubated with secondary antibody (MM HRP Polymer, Biocare Medical) for 1 h at room temperature on a rocker. After three washers in PBS 15 min each the signal was detected using the DAB Peroxidase Substrate Kit (Vector). After washes, sections were mounted onto superfrost plus slides, dried overnight and coverslip with Acrytol mounting medium.

Behavioral Analysis

Accelerating rotarod test: Motor coordination and motor learning were assessed on an accelerating rotarod apparatus (AccuScan Instruments). Mice were trained on the rotarod with three trials per day for 3 consecutive days. On the first training day, the rotarod was set to accelerate from 0 to 5 RPM over 300 sec. Mice that fell off the rod prior to completion of the 300 sec time period were placed back on the rod until the full 300 sec period had expired. On the second and third days of training, the rotarod was set to accelerate from 0 to 40 RPM over 300 sec, again requiring all mice to complete the full 300 sec on the rod. On the fourth day (test day), the mice were placed on the rotarod set to accelerate from 0 to 40 RPM over 300 sec. Animals were not replaced after falling, and the latency to fall was recorded over 3 trials. Latency to fall was defined by the time elapsed until the animal fell from the rotarod.

Porsolt Swim Test:

Immobility in the Porsolt swim test was used as a measure of depression in rodents (Porsolt et al., (1977) *Arch. Int. Pharmacodyn. Ther.* 229:327-336, Cryan et al., (2002a) *Trends Pharmacol. Sci.* 23:238-245, Cryan et al., (2002b) *Eur. J. Pharmacol.* 436:197-205). The test was conducted by placing mice in individual glass cylinders (20 cm height×10 cm diameter) filled with water at 23° C. up to a height of 15 cm. The mice were placed into the cylinders for a period of 7 min. The first 3 min of this period was considered an acclimation period, during which time no data were collected. During the last 4 min of the test session, the performance of the mice was scored by a blinded observer using a time-sampling technique to rate the predominant behavior over 10 sec intervals. Swimming and immobility behaviors were measured and recorded at the end of every 10 sec, which resulted in 24 data points per test. The percentage of time spent in an immobile state was calculated for each mouse.

Statistics

Mean values were used for statistical analyses. Data are expressed as the mean±SEM. For studies that used two groups, Student's t-test was used for statistical comparison. For comparisons of more than two groups, one-way ANOVA was used followed by Tukey's multiple comparison post-hoc test (Prism GraphPad). $p<0.05$ was considered as a statistically significant difference.

Results

Figure 1B:
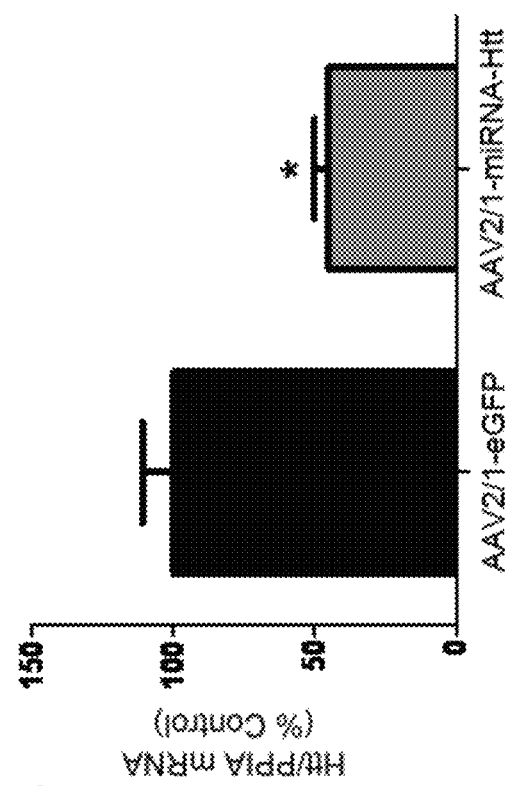
(FIG. 1B) Quantitative PCR analysis evaluating Htt mRNA levels in HEK293 cells 48 hr after AAV-2/1-miRNA-Htt treatment. PPIA served as a normalization control gene. Values are given as the means±SEM. *$p<0.05$.
Figure 2A:
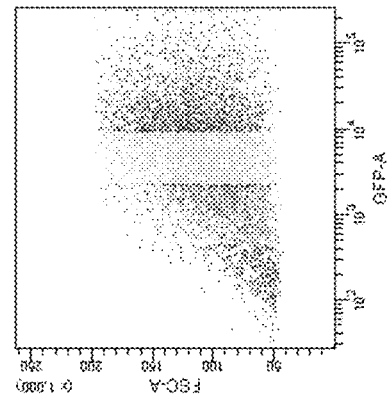
FIGS. 2A-D demonstrate fluorescent activated cell sorting (FACS) following HEK293 Cell infection with AAV2/1-eGFP-miRNA-Htt vector.
Figure 2B:
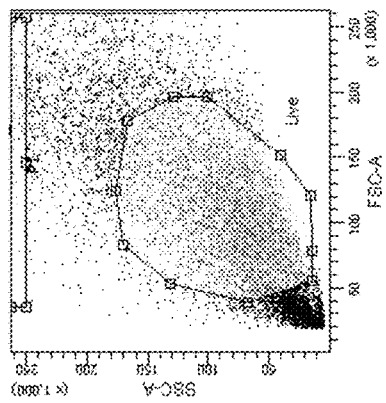
Figure 2C:
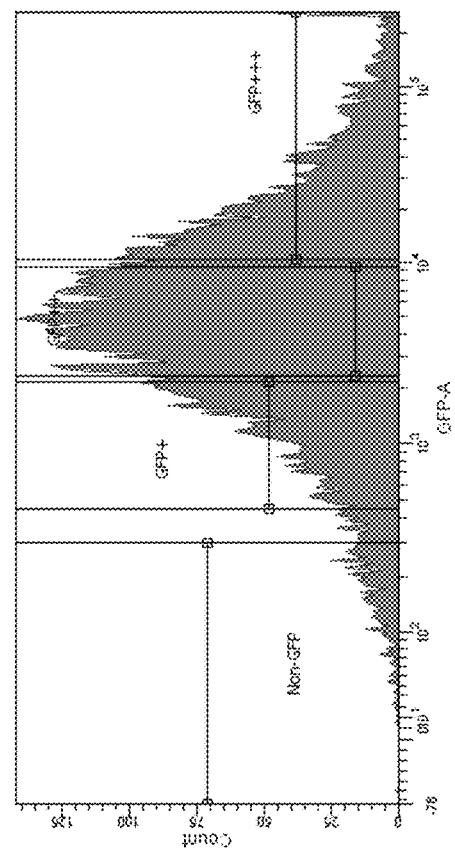
Figure 2D:
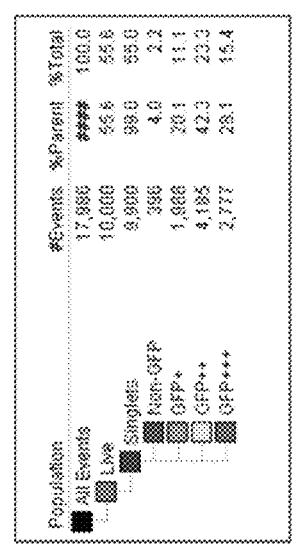

The plasmid was engineered to express the miRNA targeting Htt and an enhanced GFP (eGFP) reporter gene under the transcriptional control of a chicken beta-actin (CBA) promoter (pSP70-CBA-EGFP) as illustrated in FIG. 1A. The candidate targeting sequence, which was selected from the Htt coding region, was 5'-TAGACAATGATTCA-CACGGT-3' (SEQ ID NO: 4). High-titer recombinant AAV2/1-serotype vectors encoding the targeting sequence (AAV2/1-miRNA-Htt) and control vectors (AAV2/1-eGFP and AAV2/1-Null) were generated and their gene silencing activities tested by infecting human embryonic kidney (HEK) 293 cells. Cells were infected with $5 \times 10^9$ vg of AAV vectors. Using fluorescent activated cell sorting (FACS) analysis it was confirmed that this dose resulted in greater than 90% infection efficiencies in HEK293 cells following infection with AAV-eGFP-miRNA-HTT (FIGS. 2A-D). Cells infected with AAV2/1-eGFP did not show any reduction of endogenous Htt levels when analyzed by real-time PCR at 3 days post-infection; however, cells infected with AAV2/1-miRNA-Htt exhibited an approximately 40% reduction in Htt mRNA levels (FIG. 1B).

Example 2: AAV2/1-miRNA-Htt Injection into YAC128 Mice Results in Widespread Striatal Transduction and Reduction of Htt mRNA Following verification of AAV2/1-miRNA-Htt's ability to suppress Htt mRNA levels in vitro, the ability of this vector to silence Htt expression in the striatum of YAC128 mice was evaluated. To determine the percent transduction of cells within the striatum following intra-striatal injections of AAV2/1-miRNA-Htt, fluorescent activated cell sorting (FACS) was employed according to the methods described in Example 1.

Results

Adult YAC128 mice received bilateral intra-striatal injections of AAV2/1-eGFP-miRNA-Htt ($4.5 \times 10^{12}$ vg/ml) or the control vector, AAV2/1-eGFP ($5.6 \times 10^{12}$ vg/ml). One month following injection the striatal region of each animal was micro-dissected and eGFP-versus non-eGFP-containing cells were sorted and quantified by FACS analysis (FIGS. 3A&B). The data showed that greater than 80% of the striatum was transduced by the vector as demonstrated by the presence of eGFP within a majority of the sorted striatal cells (FIG. 3C).

Figure 4:
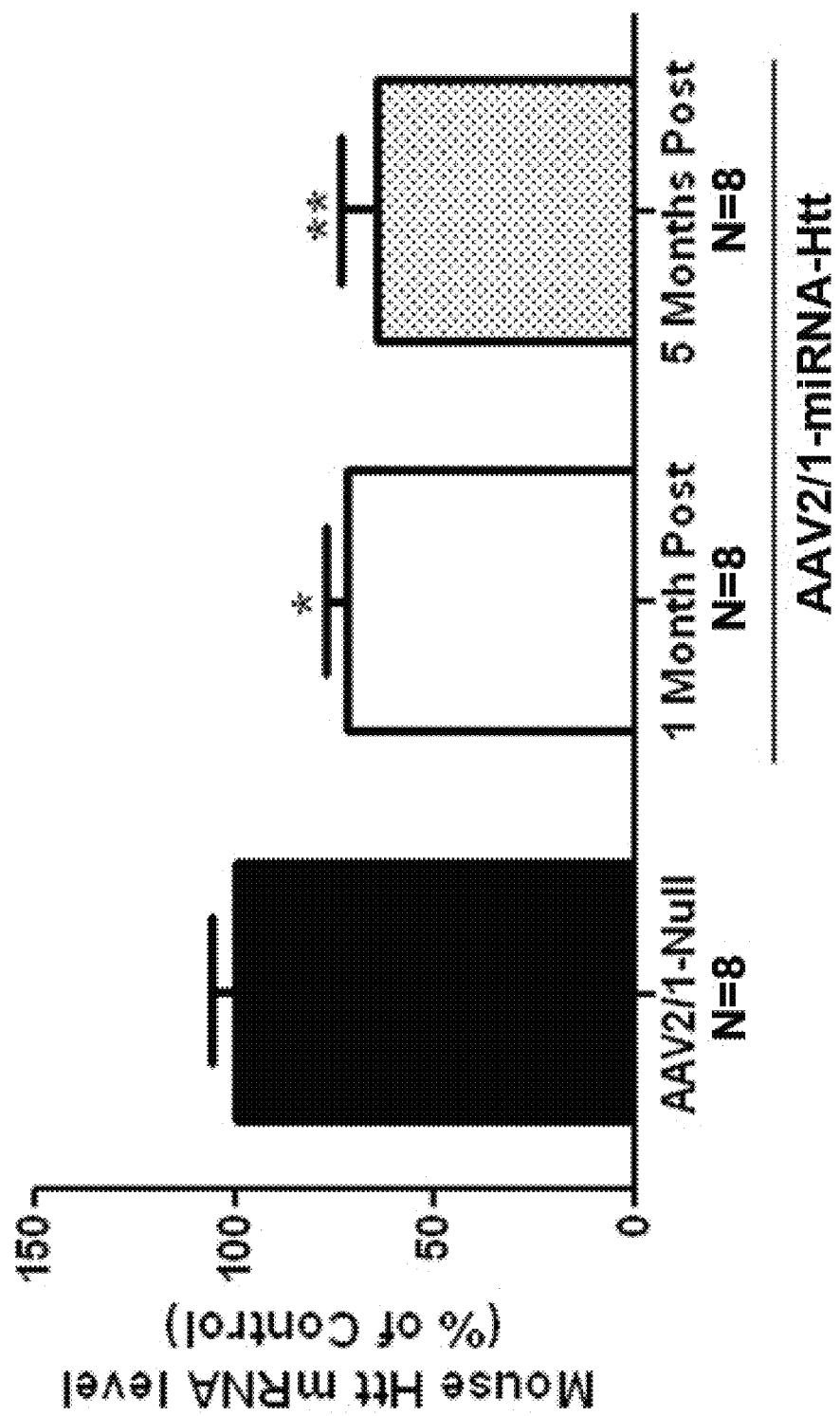
FIG. 4 shows mouse Htt mRNA reduction following intrastriatal injection of AAV2/1-miRNA-Htt injection in YAC128 mice. Quantitative PCR analysis evaluating endogenous mouse Htt mRNA levels in the striatum 1 and 5 months after injection of AAV2/1-miRNA-Htt or AAV2/1-null control vector. PPIA served as a normalization control gene. Values are given as the means±SEM. *$p<0.05$.

In order to evaluate the ability of the vector to reduce Htt in vivo and monitor the longevity of the response, adult mice received bilateral intra-striatal injections of AAV2/1-miRNA-Htt (4.5E12 vg/ml) (N=16, N=8+8 per timepoint) or the AAV2/1-Null control vector (2.3E12 vg/ml) (N=8), and the brains analyzed 1 or 5 months post-treatment. Fluorescence microscopy analysis of brain sections from mice treated with AAV2/1-miRNA-Htt at both time points showed widespread eGFP fluorescence throughout the entire striatum and surrounding brain regions, consistent with the FACS analysis suggesting almost complete striatal transduction (FIG. 3D). The levels of eGFP expression in the brains of mice attained at 1 month post-treatment appeared undiminished at the 5-month time point (FIG. 3D). The striatal levels of mutant human Htt mRNA was significantly reduced in the AAV2/1-miRNA-Htt-injected mice when compared to AAV2/1-Null-treated controls and an equivalent extent of reduction (approximately 45%, $p<0.01$) was noted at both time points (FIG. 3E). The striatal levels of endogenous mouse Htt mRNA were significantly reduced following AAV2/1-miRNA-Htt when compared to AAV2/1-Null-treated controls. An equivalent extent of reduction (approximately 45%, $p<0.01$) was noted at both time points (FIG. 4).

Example 3: AAV2/1-miRNA-Htt Injection into YAC128 Mice does not Cause Overt Toxicity in the Brain To determine whether injections of AAV2/1-miRNA-Htt and the consequent reduction of Htt conferred neurotoxicity and inflammation, cellular morphology and integrity of striatal sections were examined by hematoxylin and eosin (H&E) staining according to the methods described in Example 1. The levels of the neuroinflammatory markers glial fibrillary acidic protein (GFAP, a marker of astrocytes) and Iba-1 (a marker of microglia) were also examined at 1 and 5 months post-treatment.

Results

Figures 5J, 5K:
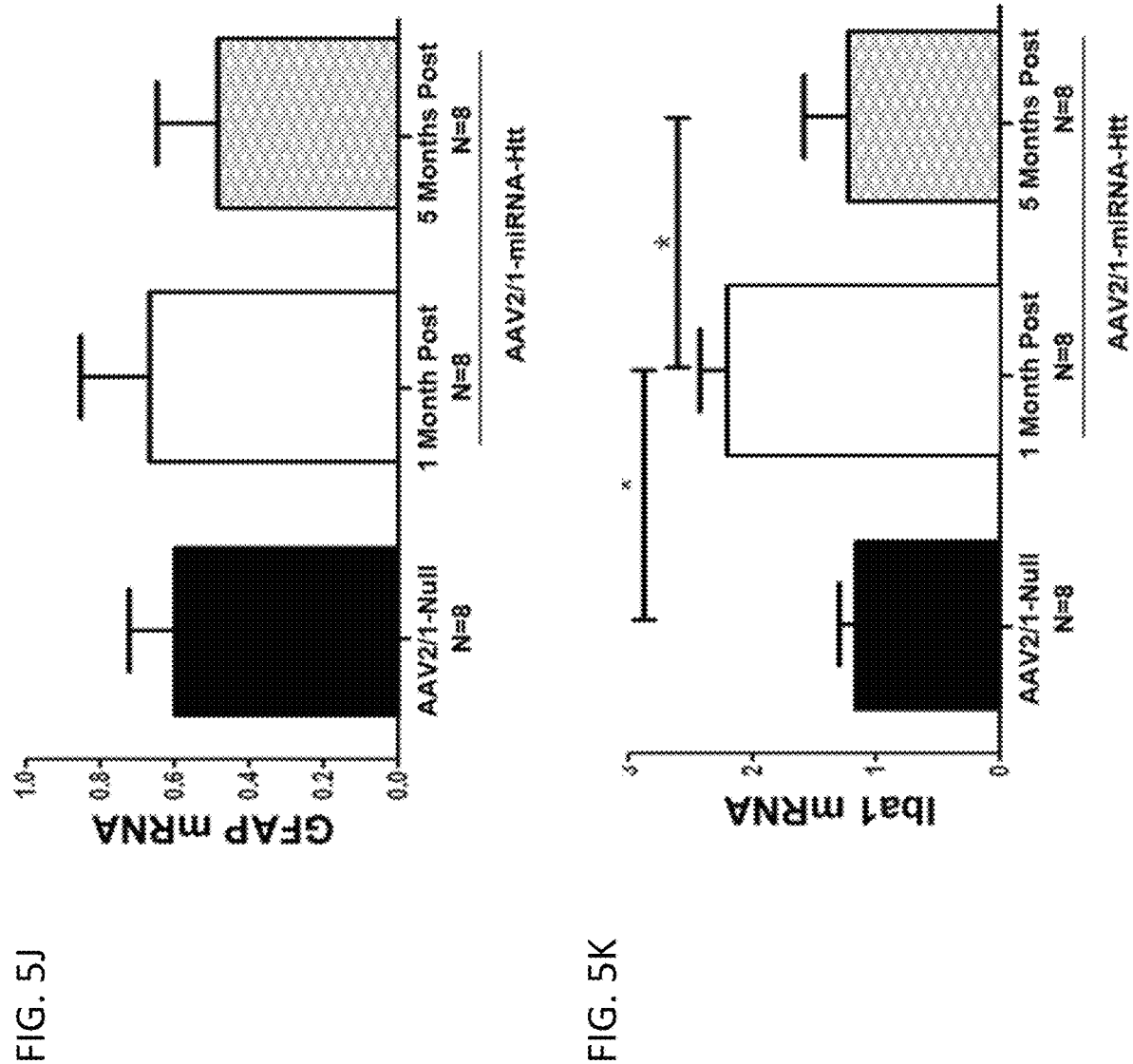
FIGS. 5J&K demonstrate that sustained lowering of Htt levels in YAC128 mice by AAV2/1-miRNA-Htt did not cause overt neuroinflammation.
(FIG. 5K) Iba1 mRNA levels by QPCR at 1 or 5 months following the injection of AAV2/1-miRNA-Htt. Values are given as the means±SEM. *Significantly different from AAV2/1-Null mice, $p<0.05$; ANOVA.

Analysis by H&E showed no remarkable histopathological changes in the injected brain regions (FIGS. 5A-C). No notable increases in either the number of GFAP-positive astrocytes (visualized by immunohistochemistry) or the levels of GFAP mRNA (quantitated by QPCR) were observed in the injected regions at 1 or 5 months post-injection when compared to AAV2/1-Null-treated animals (FIGS. 5D-F; FIG. 5J). However, an increase in the number of activated microglia, as evidenced by an increase in Iba-1 immunostaining (FIG. 5H) and Iba-1 mRNA levels in the striatum were noted at 1 month post-injection (FIG. 5K). Interestingly, at 5 months post injection, microglial activation returned to control levels (FIGS. 5I&5K), suggesting that the response was transient. Without wishing to be bound by theory, as the AAV2/1-Null control vector used in this study did not harbor an eGFP gene, it is thought that the expression of eGFP from AAV2/1-miRNA-Htt was likely responsible for the transient microglial activation.

Taken together, these results corroborate and extend the findings that AAV2/1-miRNA-Htt is capable of mediating sustained Htt silencing not only in vitro but also in the striatum of YAC128 mice. Moreover, partial suppression of Htt levels for up to 5 months did not lead to overt toxicity or neuroinflammation in the mouse brain.

Example 4: Striatal Delivery of AAV2/1-miRNA-Htt Corrects the Aberrant Behavioral and Neurochemical Profiles in YAC128 Mice The impact of AAV-mediated reduction of mutant Htt levels on the well-characterized phenotypic deficits that are present in the YAC128 mouse model of HD were also examined according to the methods described in Example 1. YAC128 mice have been reported to exhibit motor coordination deficits (which can be revealed using the rotarod test) and a depressive phenotype (using the Porsolt swim test) beginning at 3 months of age (Slow et al., (2003) *Hum. Mol. Genet.* 12:1555-1567; Van Raamsdonk et al., (2007) *Neurobiol Dis* 26:189-200).

Results

Figure 6A:
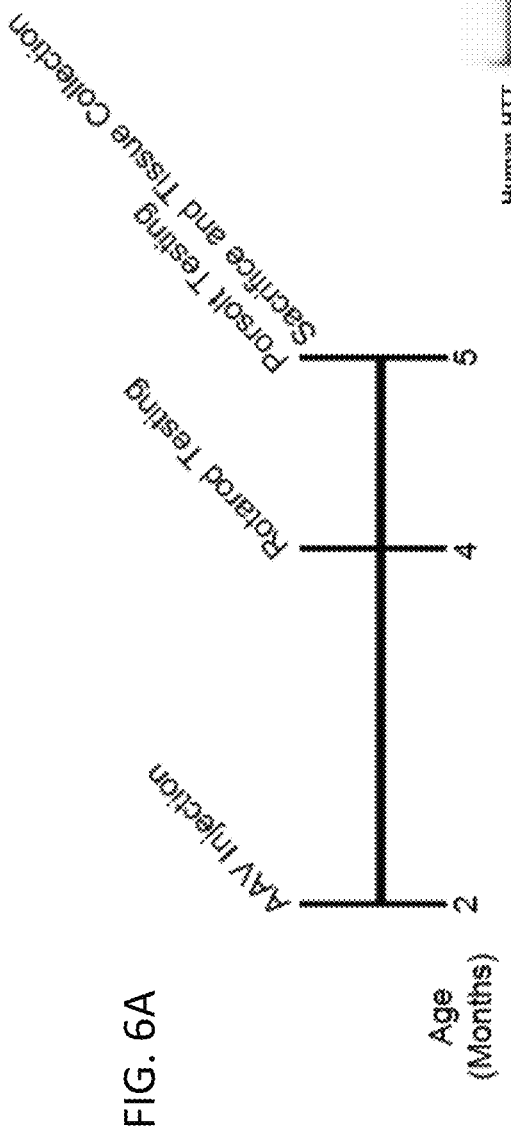
FIGS. 6A-D show the experimental design for testing the effect of striatal administration of AAV2/1-miRNA-Htt in YAC128 mice on behavioral deficits.
Figure 6B:
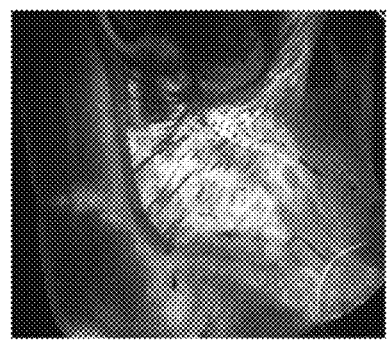
Figure 6C:
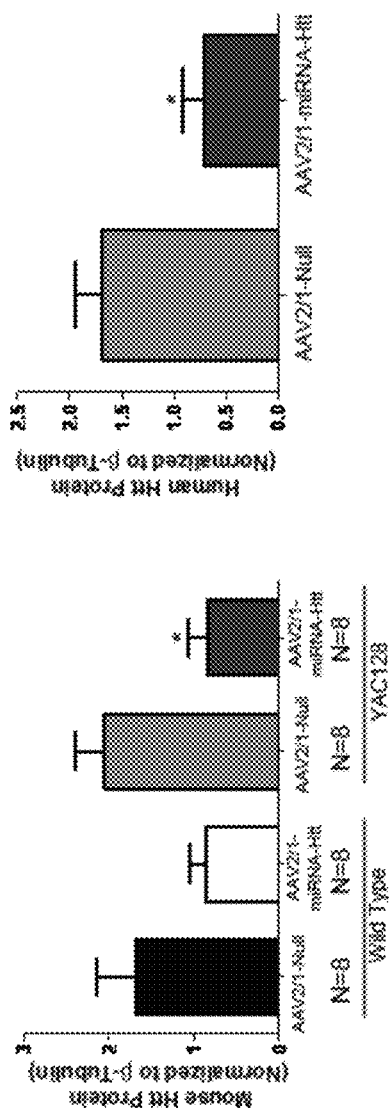
Figure 6D:
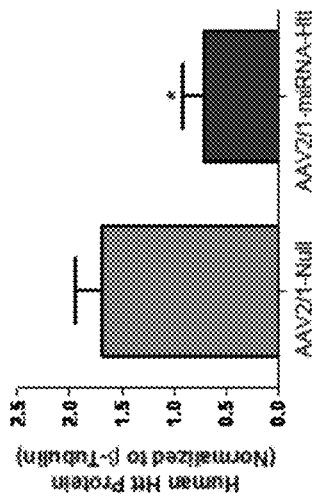

Age-matched (2 months-old) YAC128 and wild-type littermate mice received bilateral intra-striatal injections of either AAV2/1-miRNA-Htt or AAV2/1-Null vector and were then sacrificed 3 months after treatment (FIG. 6A). As expected, an analysis of brain sections demonstrated eGFP expression throughout the entire striatum and surrounding regions, as previously observed (FIG. 6B). Western blot analysis of brain homogenates showed the levels of both mutant human and endogenous mouse Htt proteins were significantly reduced in the striata of AAV2/1-miRNA-Htt injected YAC128 and wild-type mice (approximately 55% reduction, $p<0.01$) when compared to AAV2/1-Null-treated controls (FIGS. 6C&D). Real-time quantitative PCR analysis indicated a commensurate reduction in mRNA levels was also attained.

Figure 6E:
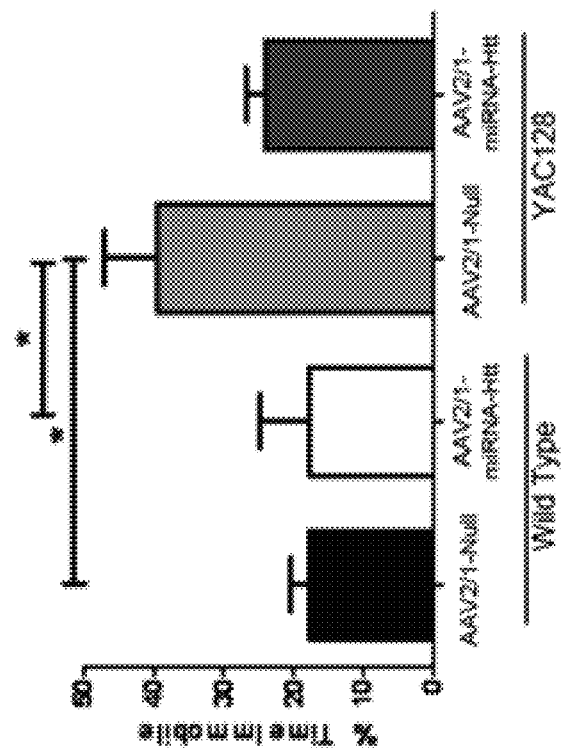
FIGS. 6E&F demonstrate that striatal administration of AAV2/1-miRNA-Htt reduced behavioral deficits in YAC128 mice.

Rotarod testing of AAV2/1-Null-treated YAC128 mice at 2 months post-injection showed significant motor coordination deficits when compared to AAV2/1-Null or AAV2/1- miRNA-Htt-treated wild-type littermates (ANOVA, p<0.01) (FIG. 6E). However, YAC128 mice that had been treated with AAV2/1-miRNA-Htt showed performance levels that were indistinguishable from those of wild-type mice (ANOVA, Tukey's post-hoc; WT Htt vs. YAC128 Htt, p=NS; WT Null vs. YAC128 Null, p<0.05). Hence, a partial lowering of mutant Htt levels was sufficient to correct the motor deficits of YAC128 mice. There were no significant differences in rotarod performance between wild-type mice that received AAV2/1-miRNA-Htt and wild-type mice that received AAV2/1-Null.

Figure 6F:
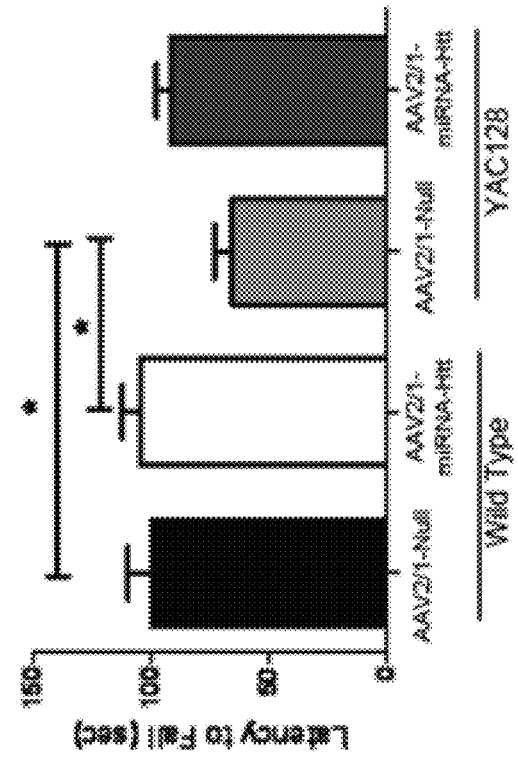
(FIG. 6F) Time spent immobile in the Porsolt swim test 3 months following the injection of AAV2/1-miRNA-Htt. Values are given as the means±SEM. *Significantly different from AAV2/1-Null mice, $p<0.05$; ANOVA followed by Tukey's post-hoc test.

Previous reports indicated that YAC128 mice (beginning at 3 months of age) exhibit a depressive phenotype that can be detected using the Porsolt swim test (Pouladi et al., (2009) Brain 132:919-932). Animals are deemed to exhibit a depressive state if they are immobile for an extended period when placed into a container of water. Using a basic swim speed test (where swim latency to reach a platform was measured) researchers have demonstrated that this depressive phenotype in the Porsolt swim test is unrelated to the swimming ability of YAC128 mice and is independent of the well documented motor coordination deficits observed in this model (Pouladi et al., (2009) Brain 132:919-932). Two-month-old YAC128 and WT littermate mice were injected with AAV2/1-miRNA-Htt- or AAV2/1-Null-vectors and tested 3 months later in the Porsolt swim test. Untreated YAC128 mice displayed an increased period of time in an immobile state when compared to either AAV2/1-miRNA-Htt-treated YAC mice or AAV2/1-Null-treated wild-type animals (FIG. 6F; ANOVA p<0.05). Again, there were no significant differences in the performance of wild-type mice that received either AAV2/1-miRNA-Htt or AAV2/1-Null. YAC128 mice that had been injected with AAV2/1-miRNA-Htt spent significantly less time in an immobile state than AAV2/1-Null-treated controls. Indeed, the performance of AAV2/1-miRNA-Htt treated YAC128 mice was similar to that of their wild-type littermates, suggesting a near-complete correction of this aberrant phenotype (ANOVA, Tukey's post-hoc; YAC Htt vs. YAC Null, p<0.05) (FIG. 6F).

Example 5: Treatment Using AAV2/1-miRNA-Htt Partially Corrects the Transcriptional Dysregulation of DARPP-32 and D1 Receptor in YAC128 Mice Transcriptional dysregulation of a number of genes enriched in the striatum has been observed in HD brains (Richfiel et al., (1995) Ann. Neurol. 37:335-343; Augood et al., (1997) Ann. Neurol. 42:215-221; Sugars et al., (2004) J. Biol. Chem. 279:4988-4999; Desplats et al., (2006) J. Neurochem. 96:743-757). This aberration is also evident in YAC128 mice, as illustrated, in particular, by their significantly lower striatal levels of DARPP-32 and D1 dopamine receptors compared to those of wild-type animals (Pouladi et al., (2012) Mol. Genet. 21:2219-2232). To examine whether the suppression of Htt levels in YAC128 mice corrected this altered transcriptional profile, real-time quantitative PCR analysis was performed on striatal tissues of YAC128 mice that had been treated at 2 months of age with AAV2/1-miRNA-Htt and analyzed 3 months later according to the methods described in Example 1.

Results

Figure 7B:
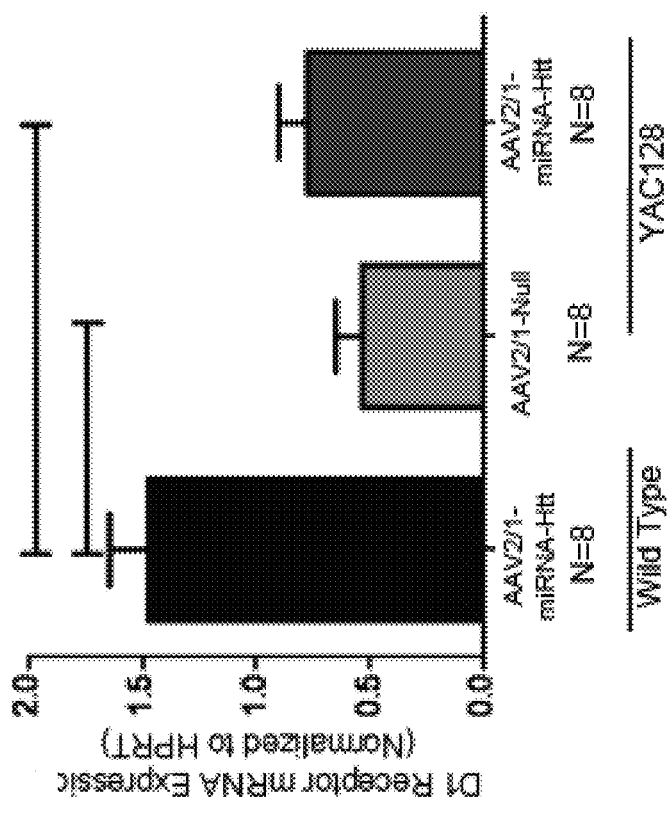
(FIG. 7B) Striatal D1 Receptor mRNA levels in YAC128 and FVB wild-type littermate mice following AAV2/1-Null or AAV2/1-miRNA-Htt treatment. Values are given as the means±SEM. *Significantly different from AAV2/1-Null samples, $p<0.05$; ANOVA followed by Tukey's post-hoc test.
Figure 7A:
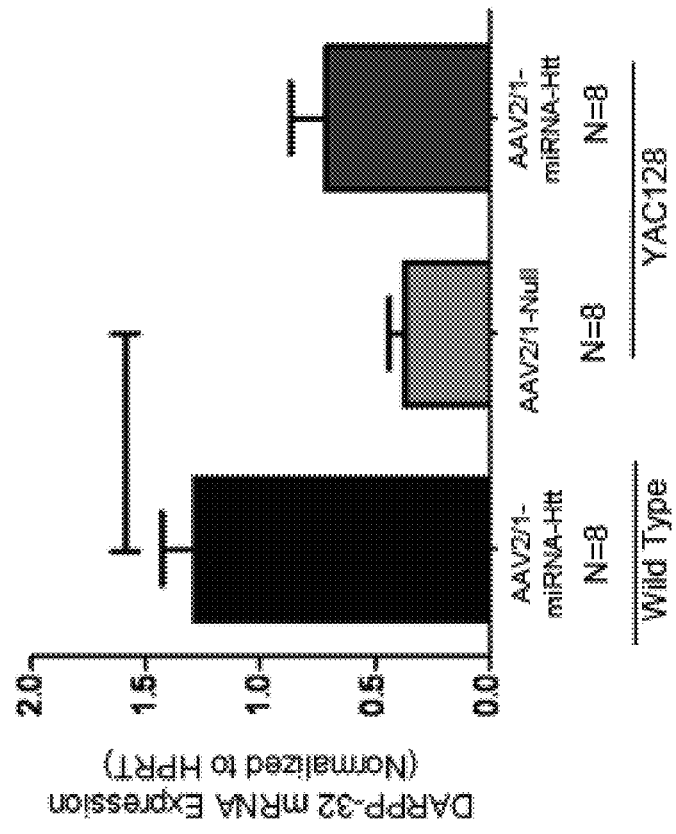
FIGS. 7A&B show that treatment using AAV2/1-miRNA-Htt partially corrected the transcriptional dysregulation of DARPP-32 and D1 receptor in YAC128 mice. DARPP-32 and D1 receptor mRNA levels in the striatum of YAC128 and wild-type mice assessed by QPCR at 3 months following the injection of either AAV2/1-miRNA-Htt (N=8 YAC and N=8 WT) or AAV2/1-Null control (N=8 YAC and N=8 WT).

An analysis of brain extracts of AAV2/1-Null-treated YAC 128 mice indicated that the mRNA levels of DARPP-32 and D1 dopamine receptor (D1R) were significantly lower when compared to age-matched wild-type controls (ANOVA, Tukey's post-hoc; WT Null vs. YAC128 Null, p<0.05) (FIGS. 7A&B). YAC128 mice that were administered AAV2/1-miRNA-Htt exhibited higher levels of DARPP-32 and D1R mRNA than those treated with AAV2/1-Null vector; however, these levels were still lower than those observed in the wild-type controls (ANOVA, Tukey's post-hoc; WT Null vs. YAC Htt, p=NS). Thus, the AAV2/1-miRNA-Htt-mediated reduction of Htt levels in YAC128 mice conferred a partial correction of the aberrant striatal transcriptional profile. It is possible that examination at later time points (greater than 5 months post-treatment) may reveal a more complete correction of this aberrant profile.

Together, these results corroborate earlier in vitro and in vivo findings that AAV2/1-miRNA-Htt is capable of mediating a sustained lowering of Htt levels. Importantly, it was demonstrated that this reduction in striatal Htt levels in YAC 128 mice results in measurable improvements in motor function and behavior as well as a partial correction of the well-characterized transcriptional dysregulation in the striatum.

Example 6: Striatal Delivery of AAV2/1-miRNA-Htt Reduces Htt Aggregates in the Brains of YAC128 Mice The appearance of Htt aggregates and inclusion bodies in the CNS is a neuropathological hallmark of HD. Lowering the levels of these aggregates in HD mice has been correlated with notable improvements in pathology (Harper et al., (2005) Proc. Natl. Acad. Sci. USA 102:5820-5825; Rodriguez-Lebron et al., (2005) Mol. Ther. 12:618-633). The YAC128 mouse model reportedly exhibits significant and widespread accumulation of Htt aggregates in the striatum by 12 months of age (Slow et al., (2003) Hum. Mol. Genet. 12:1555-1567, Pouladi et al., (2012) Hum. Mol. Genet. 21:2219-2232). The impact of AAV2/1-miRNA-Htt delivery on Htt aggregates in YAC128 mice was examined according to the methods described in Example 1.

Results

Immunohistochemical staining of brain sections of 6, 9, and 24 month-old YAC128 mice using the anti-Htt antibody EM48 showed evidence of aggregates in both the striatum and cortex as early as 6 months of age that progressed over time (FIG. 8A). Twelve month-old tissues (16 micron frozen sections) were also analyzed and shown to have a similar extent of aggregates as the 24 month-old cohort; however, non-specific background staining in frozen sections was significantly higher than in the vibratome sections (data not shown).

To examine whether the AAV-mediated reduction of mutant Htt levels lowered the extent of accumulation of Htt aggregates in the brains of post-symptomatic YAC128 mice (7 months old) and, in turn, correct the motor and behavioral deficits, mice were submitted to bilateral intra-striatal injections of either AAV2/1-miRNA-Htt or AAV2/1-GFP. The animals were subjected to testing on the rotarod at 3 months post-injection (the animals were 10 months old) and sacrificed at 5 months post-injection (when the mice were 12 months old) (FIG. 8B). AAV2/1-miRNA-Htt-treated YAC128 mice on the rotarod exhibited a level of competency that was comparable to that of their wild-type littermates (FIG. 8C; ANOVA, Tukey's post-hoc; p=NS). However, these results did not reach statistical significance due to the low numbers of mice used in the study (N=4 WT; N=6 YAC128). Immunohistochemical staining of striatal sections using the EM48 antibody showed the presence of significantly fewer Htt aggregates in AAV2/1-miRNA-Htt- than in AAV2/1-GFP-treatedYAC128 mice (FIG. 8D). The brains of AAV-miRNA-Htt-treated YAC128 mice were essentially indistinguishable from those of wild-type mice.

To confirm that the observed reduction in aggregates with AAV2/1-miRNA-Htt was not due to neuronal loss or potential neurotoxicity, H&E staining as well as immunohistochemical staining for NeuN (neuronal marker), GFAP (astrocytic marker), and Iba1 (microglial marker) was performed on adjacent sagittal brain sections. Compared to AAV-2/1-Null-injected controls, AAV2/1-miRNA-Htt injected animals showed the same abundance of NeuN-positive neurons in the striatum by fluorescent microscopy. Using light microscopy, H&E staining of adjacent coronal brain sections also appeared normal and provided supporting evidence of this lack of neuronal loss; however, because stereology was not performed, these results could not be quantified. Additionally, as observed in earlier studies, an increase in either GFAP or Iba-1 staining in AAV2/1-miRNA-Htt-treated mice at 5 months post-injection was not detected.

Conclusions

The present study show that lowering mutant Htt levels is a therapeutic strategy for HD and demonstrated that the partial reduction of mutant Htt in the striatum produced behavioral, biochemical, and neuropathological improvements in a full-length transgenic mouse model of HD, the YAC128 mouse model. Previous efforts at evaluating this therapeutic strategy were performed on mouse models harboring fragments of the mutant HTT gene, such as the R6/1 and N171-82Q HD mice (Harper et al., (2005) Proc. Natl. Acad. Sci. USA 102:5820-5825, Rodriguez-Lebron et al., (2005) Mol. Ther. 12:618-633, Machida et al., (2006) Biochem. Biophys. Res. Commun. 343:190-197). A partial reduction in the levels of the mutant Htt conferred a modest survival benefit in some of the more severe models, such as the N171-82Q HD mouse model, but not in others (e.g., the R6/1 mouse model) (Harper et al., (2005) Proc. Natl. Acad. Sci. USA 102:5820-5825, Rodriguez-Lebron et al., (2005) Mol. Ther. 12:618-633, Machida et al., (2006) Biochem. Biophys. Res. Commun. 343:190-197). Motor improvements were also noted in these studies using the rotarod and stride-length tests; however, the severity of these models precluded the long-term evaluation of treatment on behavioral, neuropathological, and biochemical aberrations.

The present study utilized the YAC128 mouse model (this model harbors a mutant human HTT gene containing 128 CAG repeats), which develops progressive motor abnormalities and age-dependent neuropathology. Compared to other HD mouse models, YAC128 mice are well suited for testing therapeutic efficacy because they recapitulate the salient genetic and clinical features of the human disease. The natural history of disease-related changes in YAC128 mice is well defined, and the animals exhibit phenotypically uniform disease characteristics that have low inter-animal variability. YAC128 mice develop an altered striatal transcriptional profile, a trait that is not observed in other similar mouse models, such as BAC HD mice (Pouladi et al., (2012) Hum. Mol. Genet. 21:2219-2232), and show age-dependent striatal neurodegeneration. As such, the testing of therapeutic interventions and the measurement of outcomes in this model may have more predictive value for clinical translation (Slow et al., (2003) Hum. Mol. Genet. 12:1555-1567).

Using the YAC128 mice, these studies demonstrated that AAV2/1-mediated expression of a miRNA targeting mutant human Htt led to a significant reduction in striatal levels of Htt mRNA and protein. Associated with the lowering of this offending entity were significant improvements in function as assessed using the rotarod and Porsolt swim tests at 5 months post-treatment as well as a significant reduction in Htt aggregates within the striatum. It is notable that the level of Htt reduction observed in these studies was only approximately 40% of control, indicating that a partial reduction of mutant Htt was sufficient to produce a significant therapeutic benefit in this mouse model. Moreover, 80% transduction of the striatum with the AAV vector led to only a partial Htt reduction. A similar phenomenon was seen in HEK293 cells in culture in which approximately 90-95% transduction efficiencies only yielded a consequent 40-50% reduction in endogenous Htt levels (see FIGS. 2A-D). These findings are consistent with previous studies in rodents and primates showing only a partial reduction of Htt levels using comparable strategies of miRNA-based silencing (McBride et al., (2008) Proc. Natl. Acad. Sci. USA 105:5868-5873; Boudreau et al., (2009b) Mol. Ther. 17:1053-1063; McBride et al., (2011) Mol. Ther. 19:2152-2162; Grondin et al., (2012) Brain 135:1197-1209). Without wishing to be bound by theory, there are a number of potential hypotheses as to why miRNA only produces partial target knock down in the transduced region. The miRNA stem-loop format used to mediate Htt silencing requires processing by the cell prior to generating functional small interfering RNAs. This requirement for cellular processing may thus set natural limits on the extent of RNA silencing imparted by miRNA-based hairpins. A report by Boudreau et al. (Boudreau et al., (2009a) Mol. Ther. 17:169-175) described the improved safety of miRNA-based platforms for therapeutic silencing in the mammalian brain and highlighted the improved toxicity profiles of miRNAs compared to traditional short hairpin structures. This improvement in safety could be due to the miRNA's reliance on endogenous cellular processing mechanisms (Boudreau et al., (2009a) Mol. Ther. 17:169-175). Despite these proposed hypotheses, it is still unknown as to the exact mechanisms behind miRNA-based Htt silencing in the brain; however the data presented here demonstrates that partial Htt reduction can achieve therapeutic benefits, at least in a mouse model of HD.

As the functional role of Htt remains unclear, there is an obvious concern associated with deploying therapeutic strategies that confer non-allele-specific silencing. The studies disclosed herein indicated that partial lowering of endogenous mouse Htt in the CNS of wild-type mice, as well as diseased YAC128 mice, for up to 5 months was well tolerated. Administration of AAV-miRNA-Htt reduced wild type mouse and mutant human Htt by approximately 40%, thus allowing for the preservation of at least 60% of wild type Htt levels while still maintaining the therapeutic benefits of silencing mutant toxic Htt. No overt toxicity or aberrant behaviors were observed. The current data is consistent with previous studies showing a similar lack of toxicity following non-allele-specific Htt silencing in HD mice and wild-type mice for up to 9 months after treatment (Boudreau et al., (2009b) Mol. Ther. 17:1053-1063). The safety of the partial suppression of wild-type Htt has also been reported in non-human primates (McBride et al., (2011) Mol. Ther. 19:2152-2162; Grondin et al., (2012) Brain 135:1197-1209), providing further confidence that the partial lowering of levels of normal Htt may not lead to significant detrimental consequences. This study further demonstrates that partial suppression (~40%) of both mutant and wild-type Htt in the YAC128 mice was therapeutic, as evidenced by their performance on a variety of behavioral tests and was not associated with any obvious adverse issues. Previous reports had suggested a role for Htt in embryogenesis and postnatal neurogenesis (Bhide et al., (1996) J. Neurosci. 16:5523-5535; Reiner et al., (2003) Mol. Neurobiol. 28:259-276; Cattaneo et al., (2005) Nat. Rev.

*Neurosci.* 6:919-930). However, to-date several preclinical studies demonstrate that partially reducing wild-type Htt levels in adult brain, appears to be well tolerated in both mouse and non-human primates (Boudreau et al., (2009b) *Mol. Ther.* 17:1053-1063; McBride et al., (2011) *Mol. Ther.* 19:2152-2162; Grondin et al., (2012) *Brain* 135:1197-1209).

A notable hallmark of HD pathology in both mouse models and human patients is the presence of mutant Htt-immunoreactive (IR) aggregates (DiFiglia et al., (1997) *Science* 277:1990-1993; Scherzinger et al., (1997) *Cell* 90:549-558). The precise role of aggregates within the cascade of pathophysiological events in HD continues to be a matter of debate (Lansbury et al., (2006) *Nature* 443:774-779) and the suggestion of a causal relationship between mutant Htt aggregates and disease remains controversial (Bates, (2003) *Lancet* 361:1642-1644; Arrasate et al., (2004) *Nature* 431:805-810). However, there is consensus that the formation of insoluble protein aggregates confers an increased burden on cellular degradative processes (Yamamoto et al., (2000) *Cell* 101:57-66). The studies disclosed herein demonstrated that YAC128 mice displayed widespread striatal aggregates as early at 6 months of age (earlier than previously reported) and injection of AAV2/1-miRNA-Htt at 7 months of age (after aggregates had already formed) significantly reduced the number of EM48-positive Htt aggregates within the striatum to nearly wild type levels. These data suggest, without wishing to be bound by theory, that AAV2/1-miRNA-Htt treatment may diminish the available pool of Htt, significantly alleviating the burden of mutant Htt aggregates and thus potentially contributing to the functional improvements noted in this mouse model.

In addition to the substantial removal of Htt aggregates, AAV-miRNA-Htt treatment also conferred a behavioral benefit in YAC128 mice. YAC128 mice begin to exhibit deficits on the Rotarod starting at 3 months of age, and by 7 months they show a severe impairment (Slow et al., (2003) *Hum. Mol. Genet.* 12:1555-1567). YAC128 mice treated with AAV2/1-miRNA-Htt at 7 months of age (when motor coordination would be significantly impaired) showed improvements on the Rotarod test suggesting a reversal of established motor deficits was obtained. Although reductions in Htt aggregates have been reported previously (N171 and R6/2 fragment models) (Rodriguez-Lebron et al., (2005) *Mol. Ther.* 12:618-633; Machida et al., (2006) *Biochem. Biophys. Res. Commun.* 343:190-197), the present studies demonstrate amelioration of aggregates and concomitant behavioral improvements in a full length mouse model of HD. A significant improvement in the Porsolt swim test following AAV-miRNA-Htt injection into the striatum was also observed. This is the first report to show an improvement in this depressive phenotype following AAV-RNAi and importantly these results suggest, without wishing to be bound by theory, that reduction of Htt levels in the striatum was sufficient to improve the depressive phenotype exhibited in the YAC128 model. Finally, when 7 month old YAC128 mice were treated with AAV-miRNA-Htt (post-symptomatic treatment) a significant reduction in Htt aggregates in the striatum and a potential a reversal in the motor coordination deficit exhibited by this model was observed. Without wishing to be bound by theory, these data indicate that post-symptomatic treatment with AAV2/1-miRNA-Htt may alleviate the mHtt burden within cells and provide a therapeutic benefit even after mHtt aggregates have formed.

Suppression of striatal Htt also resulted in a modest correction of DARPP-32 and D1 receptor mRNA levels, 2 transcripts that decline progressively with age in YAC128 mice and human HD patients. Mutant Htt is known to confound a number of cellular processes leading to neuronal dysfunction and transcriptional dysregulation (Cha, (2000) *Trends Neurosci.* 23:387-392).

In summary, these studies demonstrate that AAV-mediated RNAi significantly improves HD-related behavioral abnormalities in the YAC128 mouse model of HD. Furthermore it also shows that the AAV-mediated delivery of a miRNA targeting Htt can lead to the sustained suppression of Htt levels, the correction of the cellular and neuropathological aberrations, and improvements in motor and behavioral deficits in a transgenic mouse model of HD without overt toxicity.

Improved RNAi by Modification of shRNA Base Pairing

Figure 9B:
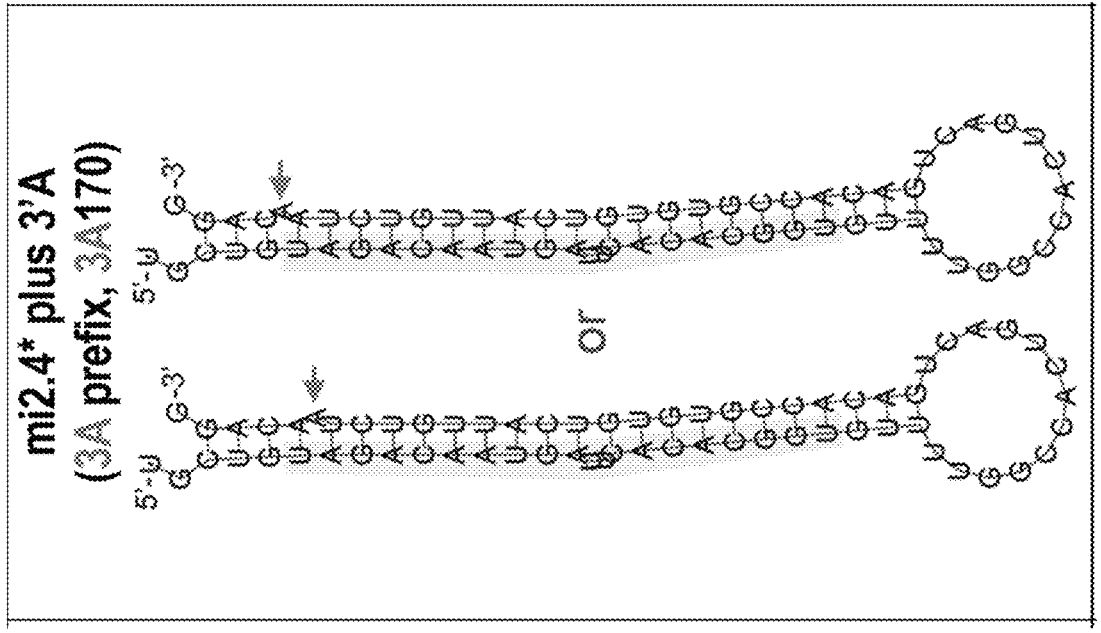
FIGS. 9A&B illustrate the internal bulge in the stem sequence of the shRNA used for the experiments described herein. As compared to the perfectly matching sequence shown in FIG. 9A (SEQ ID NO:23), the sequence used in the above experiments contained an additional adenine nucleotide (A) at the 3' end of the seed sequence (highlighted by arrows), which did not have a corresponding thymine nucleotide (T) in the guide strand (SEQ ID NO:24) (FIG. 9B). Sequences complementary to the target sequence are highlighted.
Figure 9A:
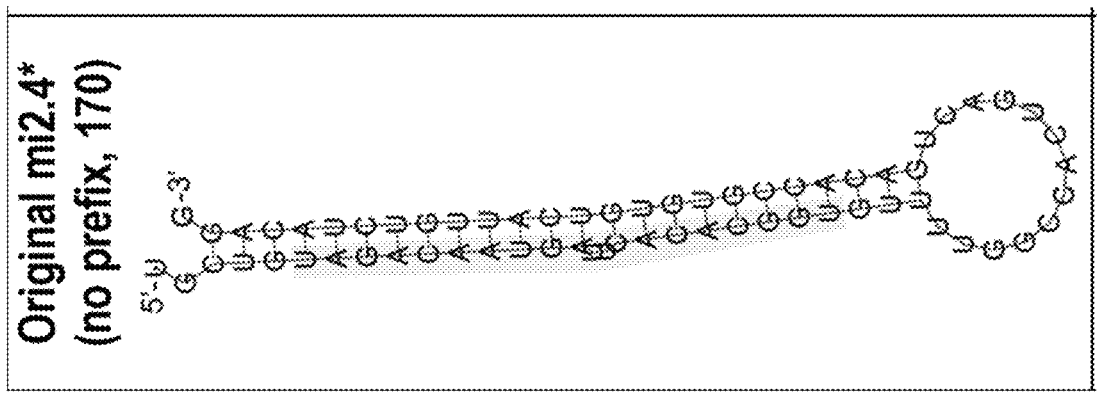

The present study utilized a recombinant AAV2/1 vector to encode a short hairpin against the Htt gene embedded in a miRNA scaffold (miR-155). The shRNA sequence used was modified from the previous published sequence mirR2.4, which targets exon 2 of mouse and human htt transcripts (McBride et al., (2008) *Proc. Natl. Acad. Sci. USA* 105:5868-5873). Modifications of short hairpin RNAs have been used to increase stability and biological activity, minimize off-target effects, and reduce innate immune responses (Castanotto et al., (2009) *Nature* 457:426-433; Jackson et al., (2010) *Nature Rev. Drug Disc.* 9:57-67). The modified sequence used in the present study contained the same guide strand sequence as miR2.4 (FIG. 9A); however, the construct was engineered to have an additional adenine nucleotide (A) at the 3' end of the seed sequence, which did not have a corresponding thymine nucleotide (T) in the guide strand (FIG. 9B). Without wishing to be bound by theory, thermodynamic modeling suggests that the additional of a bulge sequence in the non-guide strand opposite of the seed sequence on the guide strand can improve aspects of RNAi performance. Accordingly, the inventors have also developed an advancement that can be used to generate novel transformative nucleic acid therapies for treating a variety of disorders.

Example 7. Reduction of Off-Target Gene Silencing

RNA interference (RNAi) provides an approach for the treatment of many human diseases. However, the safety of RNAi-based therapies can be hampered by the ability of small inhibitory RNAs (siRNAs) to bind to unintended mRNAs and reduce their expression, an effect known as off-target gene silencing. Off-targeting primarily occurs when the seed region (nucleotides 2-8 of the small RNA) pairs with sequences in 3'-UTRs of unintended mRNAs and directs translational repression and destabilization of those transcripts. To date, most therapeutic RNAi sequences are selected primarily for gene silencing efficacy, and later evaluated for safety. Here, in designing siRNAs to treat Huntington's disease (HD), a dominant neurodegenerative disorder, two new sequences with minimal off-targeting potentials (i.e., those with a scarcity of seed complements within all known human and rhesus monkey 3'-UTRs) were generated which show potent silencing in the mouse brain with a low in silico off-target profile.

TABLE 1 miRNA sequences

| miRNA ID | miRNA sequence (anti-sense, 5'→3') | #siSPOTR off-targets (human) | Top seq for cloning (5'→3') Stem loop that contains actual miRNA sequence, including restriction site overhangs (underlined) |
|---|---|---|---|
| Original design | | | |
| 170XA | UAGACAAUGAUUCAC ACGGU (SEQ ID NO: 1) | 6001 | <u>TGCTGT</u>AGACAATGATTCACACGGTGTTTTGGCCACT GACTGACACCGTGTGTCATTGTCT<u>AA</u> (SEQ ID NO: 20) |
| Modified to be low off-targeting: | | | |
| 170XA L1 | UCGACAAUGAUUCAC ACGGU (SEQ ID NO: 15) | 786 | <u>TGCTGT</u>CGACAATGATTCACACGGTGTTTTGGCCACT GACTGACACCGTGTGTCATTGTCG<u>AA</u> (SEQ ID NO: 21) |
| 170XA L2 | UAGACGAUGAUUCAC ACGGU (SEQ ID NO: 17) | 1223 | <u>TGCTGT</u>AGACGATGATTCACACGGTGTTTTGGCCACT GACTGACACCGTGTGTCATCGTCT<u>AA</u> (SEQ ID NO: 21) |

Shown in Table 1 are the original PS170XA miRNA sequence and the two modified low-off targeting versions of this sequence: 170XAL1 and 170XAL2. The two low off-targeting versions of PS170XA were designed by substituting bases within the heptamer from bases 2-8 to create CpG motifs. (Boudreau et al, 2012). The 'A' at positions 2 was changed to a C in 170XAL1 (5'-UCGACAAUGAUUCA-CACGGU-3') (SEQ ID NO:15), and the 'A' at position 6 was changed to a 'G' in 170XAL2 (5'-UAGACGAUGAUU-CACACGGU-3') (SEQ ID NO:17). These substitutions resulted in a significantly lower off target score using the SiSPOTR algorithm, a specificity-focused siRNA design algorithm which identifies candidate sequences with minimal off-targeting potentials and potent silencing capacities (Boudreau et al, *Nucleic Acids Res.* 2013 January; 41(1) e9. The reduced SiSPOTR score would predict the new sequences would have a lower number of potential human off targets compared to the original 170XA sequence.

Figure 10:
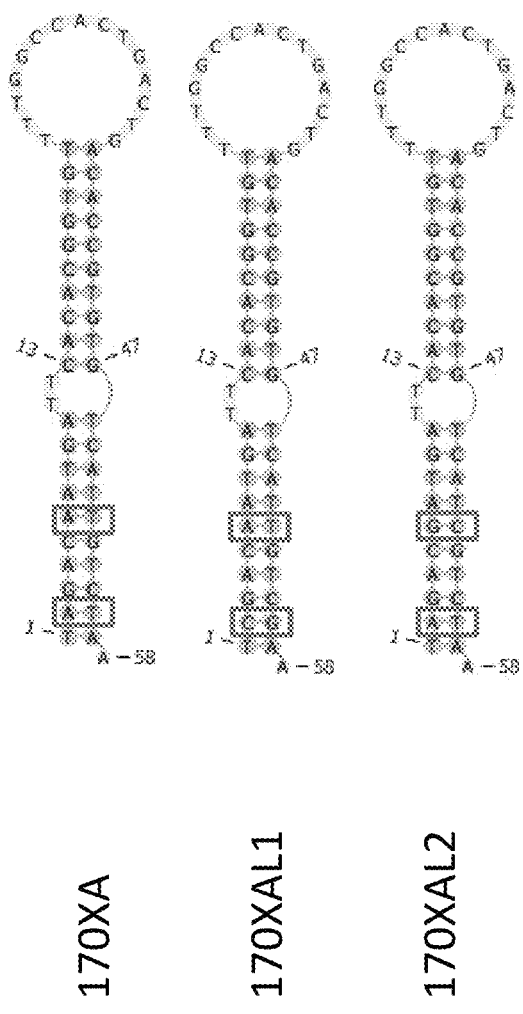
FIG. 10 shows the original PS170XA miRNA sequence (SEQ ID NO:19) and two modified low-off targeting versions, PS170XAL1 (SEQ ID NO:25) and PS170XAL2 (SEQ ID NO:26).

The original PS170XA miRNA sequence is 5'-UAGA-CAAUGAUUCACACGGU-3' (SEQ ID NO:1). The following sequence, including the guide strand, modified mir-155 internal loop (murine), and passenger strand, was cloned into an expression vector: 5'TAGACAATGATTCACACG-GTGTTTTGGCCACTGACTGACACCGTGTGTCATTGT CTAA-3' (SEQ ID NO:19). An additional 'A' is included at the 3' end. Guide and passenger strands are in bold, and bases 11 and 12 of the guide strand are not reverse-complemented in the passenger strand, creating a small internal loop in the mature, processed duplex. The 'A' at positions 2 was changed to a C in 170XAL1, and the 'A' at position 6 was changed to a 'G' in 170XAL2, otherwise, 170XAL1 and 170XAL2 have the same structure as the original PS170XA. Structures are shown in FIG. 10.

Figure 11:
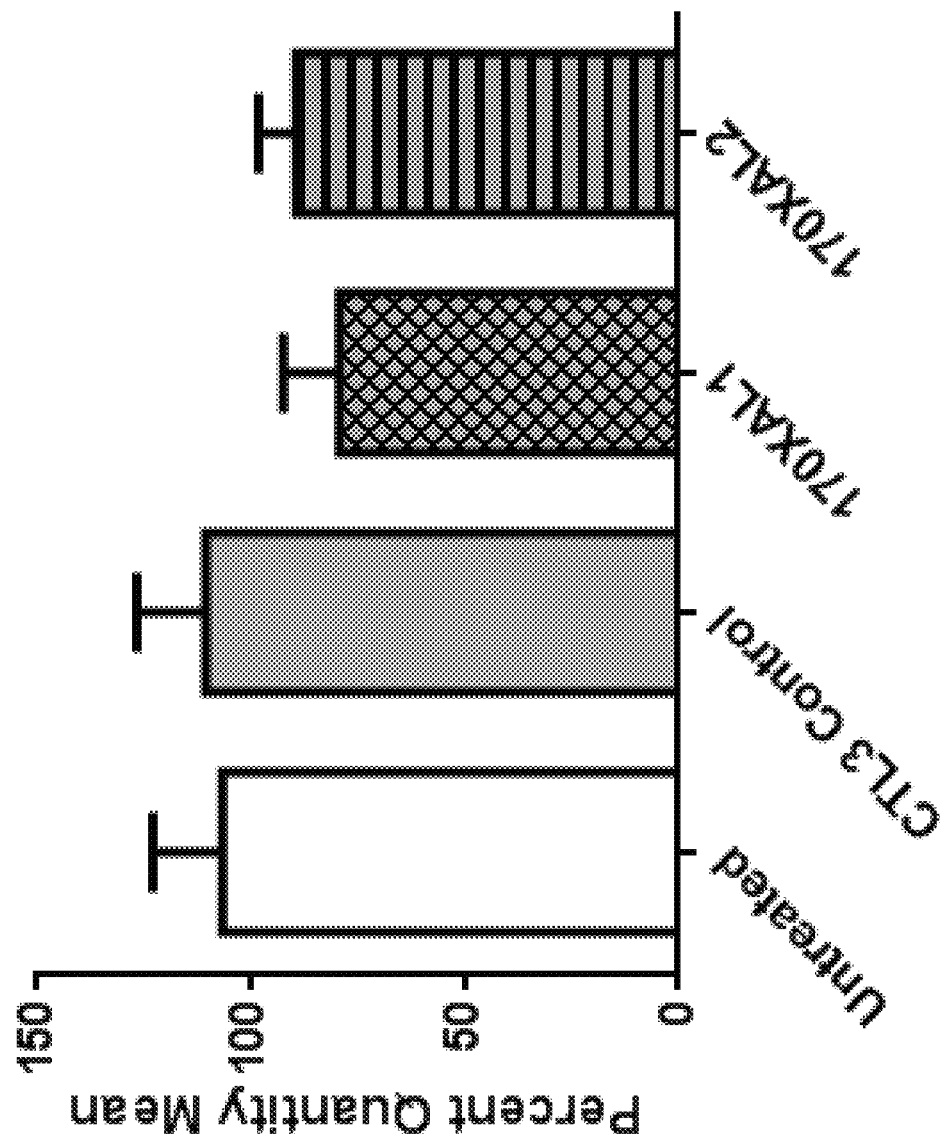
FIG. 11 shows the ability of AAV ability of AAV2/1-miRNA-Htt 170XAL1 and 170XAL2 to mediate Htt reduction in vitro. Values are given as the means±SEM.

The ability of AAV2/1-miRNA-Htt 170XAL1 and 170XAL2 to mediate Htt reduction in vitro in human embryonic kidney (HEK293) cells was tested. AAV2/1-miRNA-Htt 170XAL1 and 170XAL2 expression plasmids as well as a control plasmid containing an noncoding miRNA sequence (CTL3) were transfected HEK293 cells (8 replicates per treatment). Cells were transfected using Fugene transfection reagent and harvested 48 hours later. Total RNA was isolated using the TaqMan® Cells-to-CT™ Kit (Ambion). RNA levels were measured by quantitative real-time RT-PCR (conducted and analyzed on an ABI Prism 7500 Sequence Detector (Applied Biosystems)). Expression levels were normalized to human PPIA (peptidylprolyl isomerase). Human Htt mRNA levels were reduced following tranfection with both 170XAL2 and 170XAL2 plasmids compared to CTL3 and untreated controls, however this reduction did not reach statistical significant (FIG. 11).

Figure 12A:
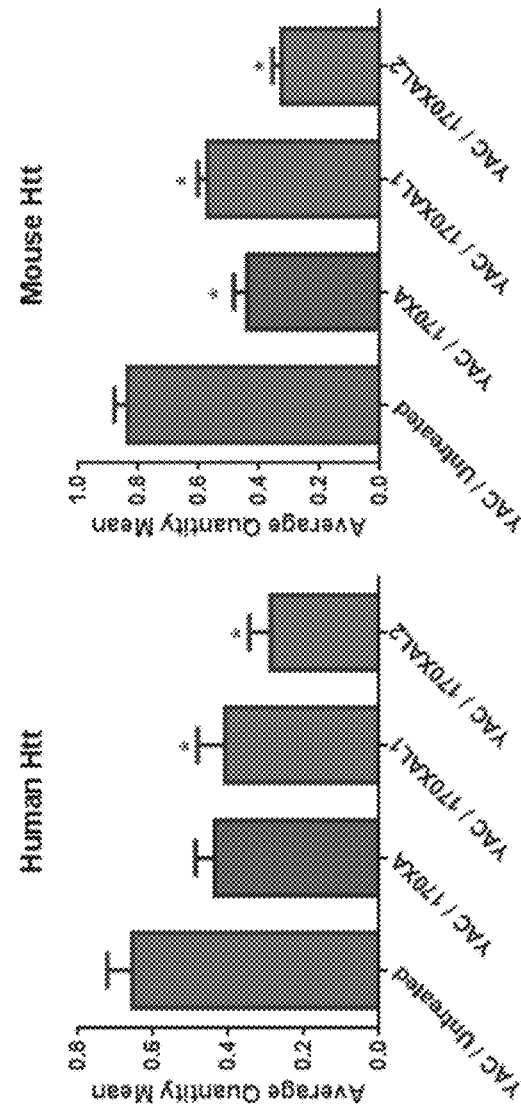
FIGS. 12A-12D show the ability of AAV ability of AAV2/1-miRNA-Htt 170XAL1 and 170XAL2 to silence Htt expression in the striatum of YAC128 mice. Human Htt is shown in FIGS. 12A and 12C. Mouse Htt is shown in FIGS. 12B and 12D. Beta-tubulin served as a normalization control gene for all western blots. *Significantly different from Untreated control mice, $p<0.05$; ANOVA followed by Tukey's post-hoc test.
Figure 12B:
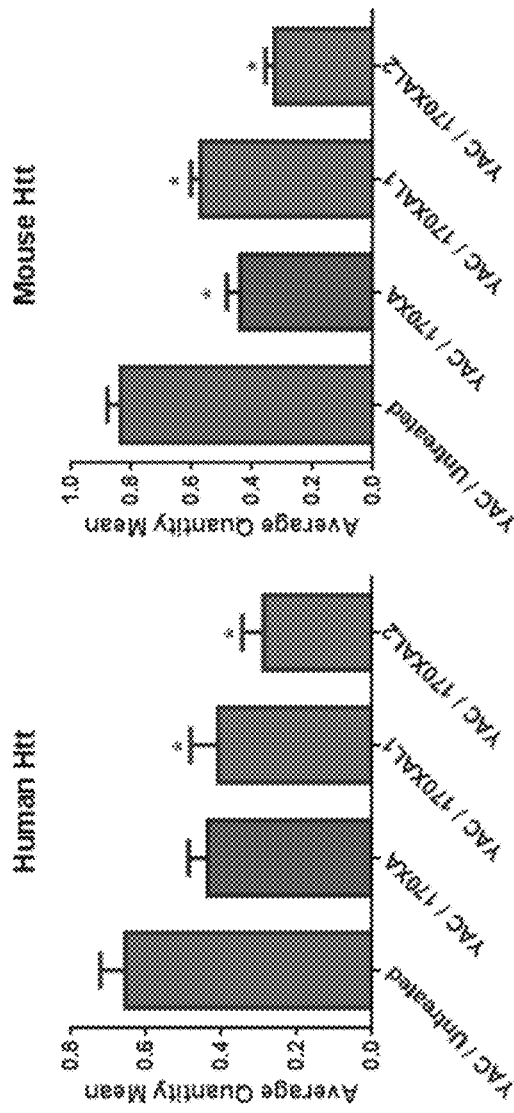
Figure 12C:
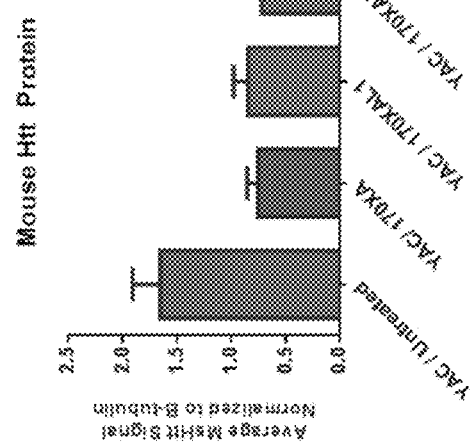
Figure 12D:
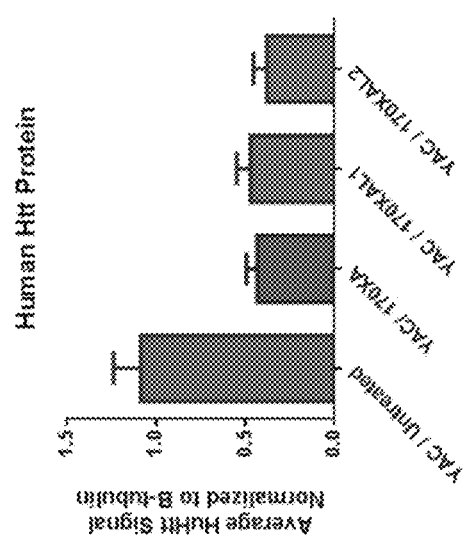

The ability of AAV2/1-miRNA-Htt 170XAL1 and 170XAL2 to silence Htt expression in the striatum of YAC128 mice was evaluated. Adult YAC128 mice received bilateral intra-striatal injections of AAV2/1-miRNA-Htt 170XA (2E10 vgs/site), AAV2/1-miRNA-Htt 170XAL1 (2E10 vgs/site), or AAV2/1-miRNA-Htt 170XAL2 (3E10 vgs/site). The original AAV2/1-miRNA-Htt 170XA served as a positive control while another group of untreated (no injection) served as the negative control. One month following injection, animals were sacrificed and perfused with PBS. Brains were collected for histology and biochemical analyses. For biochemical analyses the striatal region of one hemisphere was micro-dissected and snap frozen in liquid nitrogen. Striatal levels of mutant human and mouse Htt mRNA and protein were evaluated by QPCR and Western blot respectively. Mutant human Htt and mouse Htt mRNA was significantly reduced in AAV2/1-miRNA-Htt 170XAL1 and AAV2/1-miRNA-Htt 170XAL2 injected mice when compared to untreated control animals (FIGS. 12A and 12B). PPIA served as a normalization control gene for all QPCR assays. Mutant human and mouse Htt protein was significantly reduced in all AAV2/1-miRNA-Htt-injected mice when compared to untreated control animals and an equivalent extent of reduction (approximately 50%, p<0.05) was noted across all treatments (FIGS. 12C and 12D).

Figure 13A:
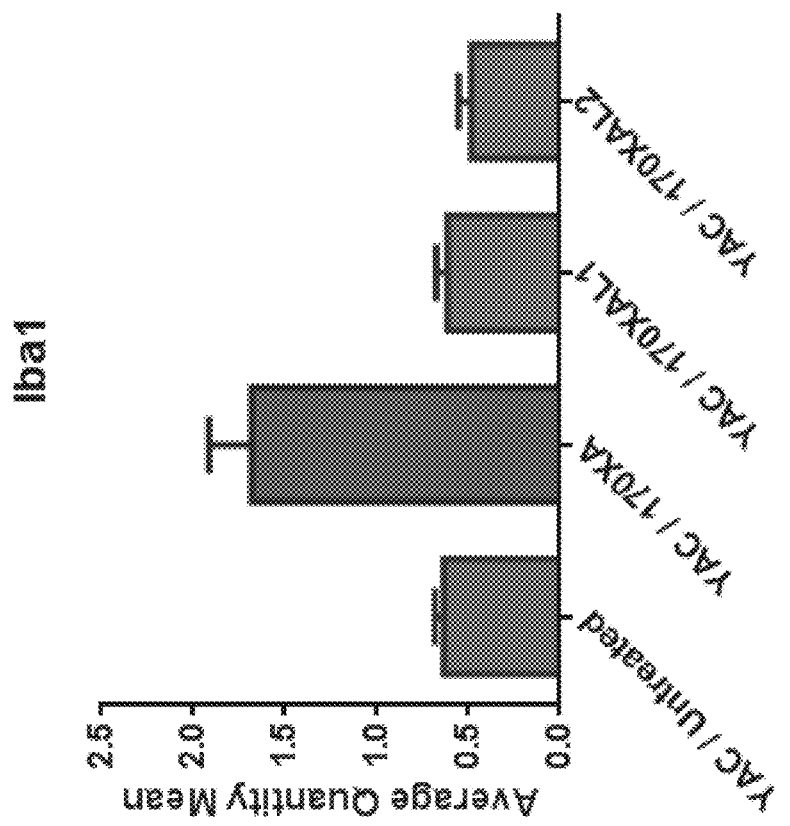
FIG. 13A shows GFAP and FIG. 13B shows Iba1 mRNA levels in the striatum. Human PPIA served as a normalization control gene. Values are given as the means±SEM. *Significantly different from Untreated control mice, $p<0.05$; ANOVA followed by Tukey's post-hoc test.
Figure 13B:
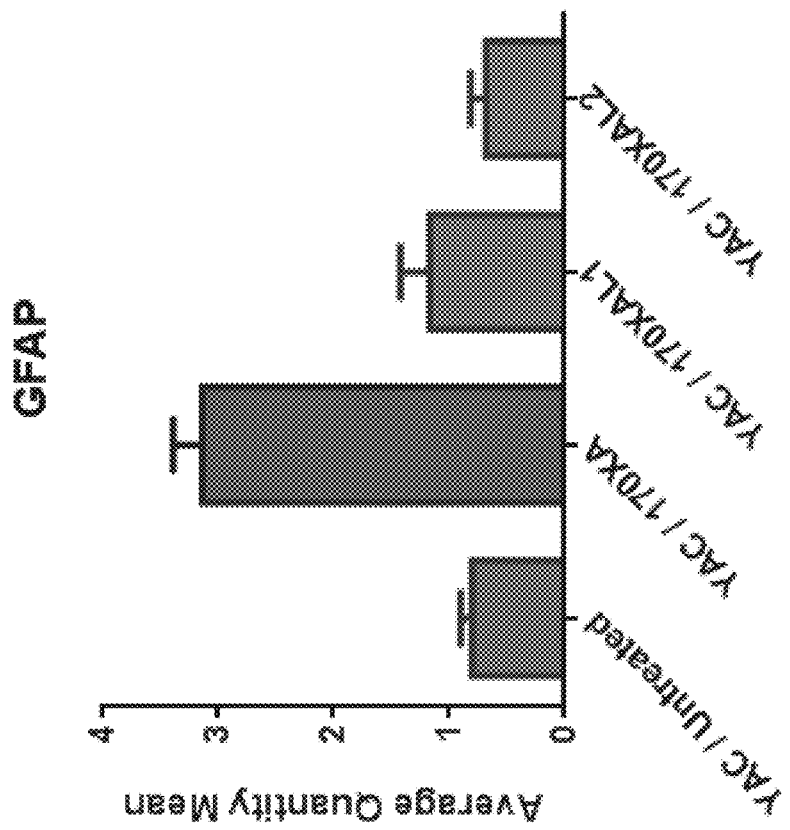

GFAP and Iba1 mRNA levels in the striatum by QPCR to determine if these inflammatory marker genes were unregulated following injection of our AAV-miRNA-Htt vectors were evaluated. GFAP is a marker of astrogliosis and Iba1 serves as a marker for microglial activation. We demonstrate that intra-striatal injections of AAV2/1-miRNA-Htt 170XA results in a significant increase in GFAP mRNA (FIG. 13A) and Iba1 mRNA (FIG. 13B) levels in the striatum 1 month injection. No increase in either GFAP or Iba1 was observed following injection of AAV2/1-miRNA-Htt 170XAL1 or AAV2/1-miRNA-Htt 170XAL2 and GFAP and Iba1 mRNA levels were equivalent to untreated controls. Human PPIA served as a normalization control gene. Values are given as the means±SEM. *Significantly different from Untreated control mice, $p<0.05$; ANOVA followed by Tukey's post-hoc test.

Figure 14:
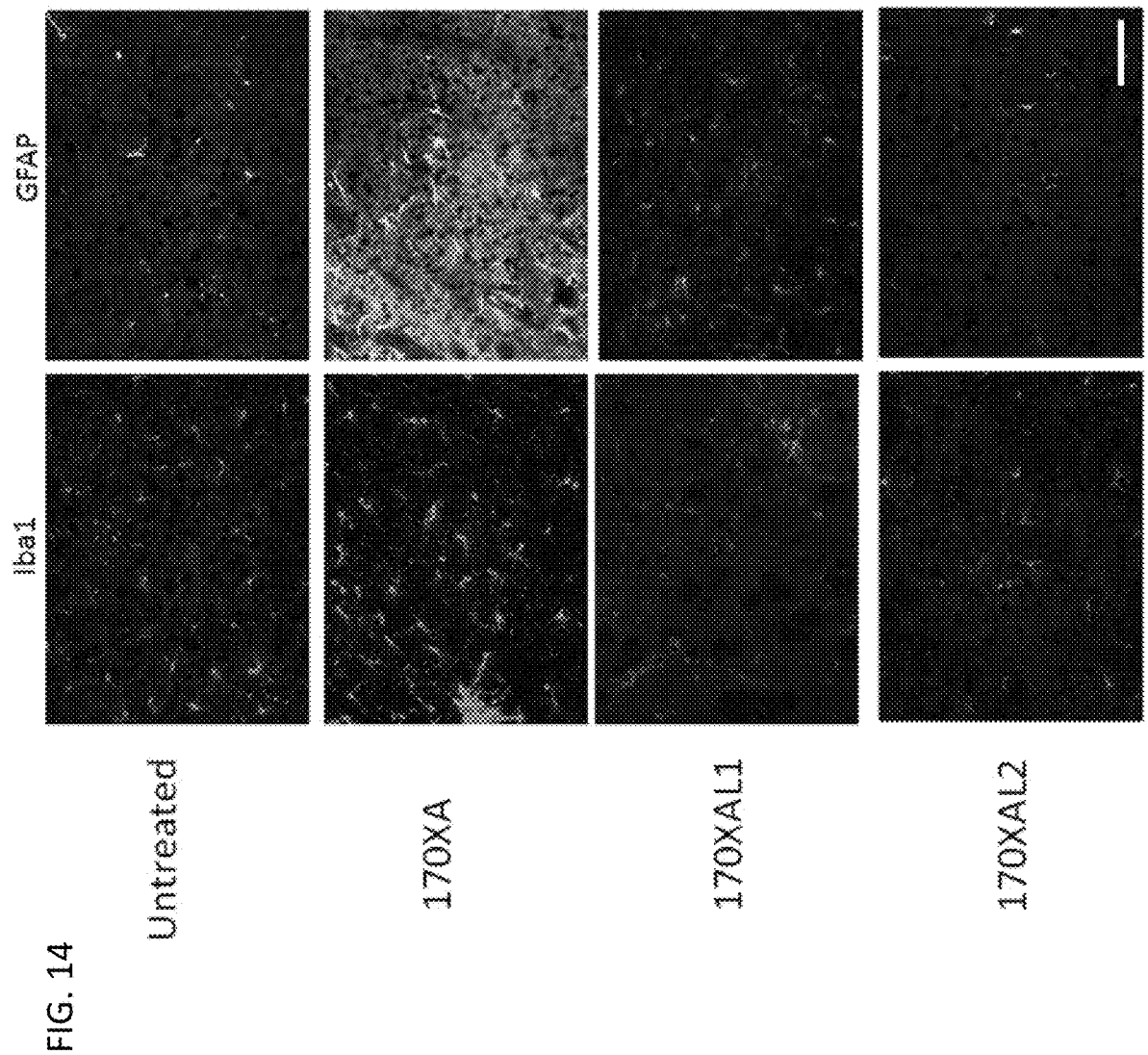
FIG. 14 shows GFAP and Iba1 immunohistochemical staining of striatal tissue sections from YAC128 mice treated with AAV2/1-miRNA-Htt 170XAL1 or AAV2/1-miRNA-Htt 170XAL2. Scale bar=50 µM.

GFAP and Iba1 immunohistochemical staining of striatal tissue sections from YAC128 mice treated with AAV2/1-miRNA-Htt 170XAL1 or AAV2/1-miRNA-Htt 170XAL2 1 month following injection confirmed that GFAP and Iba1 protein levels were not elevated in the striatum following injection (FIG. 14). Fluorescent microscopy was used to evaluate the level of GFAP and Iba1 immunostaining in the brain. Intra-striatal injections of AAV2/1-miRNA-Htt 170XA did result in a increase in GFAP and Iba-1 immunoreactivity as seen by fluorescent microscopy, however we did not observe any increase in either GFAP or Iba1 immunostaining following injection of AAV2/1-miRNA-Htt 170XAL1 or AAV2/1-miRNA-Htt 170XAL2 where level of staining were equivalent to untreated control brains. Scale bar=50 µM.

SEQUENCES

All polypeptide sequences are presented as N-terminal to C-terminal unless indicated otherwise. All nucleic acid sequences are presented as 5' to 3' unless indicated otherwise.

```
miRNA htt antisense strand
                                                                    (SEQ ID NO: 1)
UAGACAAUGAUUCACACGGU miRNA Passenger strand complement
                                                                    (SEQ ID NO: 2)
ACCGUGUGUCAUUGUCUAA Sense target sequence
                                                                    (SEQ ID NO: 3)
ACCGUGUGAAUCAUUGUCUAA miRNA htt antisense strand DNA sequence
                                                                    (SEQ ID NO: 4)
TAGACAATGATTCACACGGT miRNA Passenger strand complement
                                                                    (SEQ ID NO: 5)
ACCGTGTGTCATTGTCTAA Sense target sequence
                                                                    (SEQ ID NO: 6)
ACCGTGTGAATCATTGTCUTAA 3A170 RNA sequence
                                                                    (SEQ ID NO: 7)
UGCUGUAGACAAUGAUUCACACGGUGUUUUGGCCACUGACUGACACCGUGUCAUUGUCUAACAGG 3A170 DNA sequence
                                                                    (SEQ ID NO: 8)
TGCTGTAGACAATGATTCACACGGTGTTTTGGCCACTGACTGACACCGTGTCATTGTCTAACAGG Human Htt mRNA forward primer
                                                                    (SEQ ID NO: 9)
Ctccgtccggtagacatgct Human Htt mRNA reverse primer
                                                                    (SEQ ID NO: 10)
Ggaaatcagaaccctcaaatgg Human Htt mRNA probe
                                                                    (SEQ ID NO: 11)
Tgagcactgttcaactgtgtgtatcggga Variant AAV ITR for scAAV vectors
                                                                    (SEQ ID NO: 12)
CACTCCCTCTCTGCGCGCTCGCTCGCTCACTGAGGCCGGGCGACCAAAGGTCGCCCACGCCCGGGCTTTGCCCGGGCG.

Full AAV vector genome DNA sequence
                                                                    (SEQ ID NO: 13)
ttggccactccctctctgcgcgctcgctcgctcactgaggccgggcgaccaaaggtcgcccgacgcccgggctttgcccggc ggcctcagtgagcgagcgagcgcgcagagagggagtggccaactccatcactaggggttcctggaggggtggagtcgtgacaa ttcgcccttgggcctaggcaattggatcccggaccgtcgacattgattattgactagttattaatagtaatcaattacgggt cattagttcatagcccatatatggagttccgcgttacataacttacggtaaatggcccgcctggctgaccgcccaacgaccc cgcccattgacgtcaataatgacgtatgttcccatagtaacgccaatagggactttccattgacgtcaatgggtggagtattt acggtaaactgcccacttggcagtacatcaagtgtatcatatgccaagtacgccccctattgacgtcaatgacggtaaatggc ccgcctggcattatgcccagtacatgaccttatgggactttcctacttggcagtacatctacgtattagtcatcgctattacc atggtcgaggtgagccccacgttctgcttcactctccccatctcccccccctccccaccccaatttttgtatttatttatttt
```

-continued

```
ttaattattttgtgcagcgatgggggcgggggggggggggggcgcgcgccaggcggggcggggcggggcgaggggcggggcg gggcgaggcggagaggtgcggcggcagccaatcagagcggcgcgctccgaaagtttccttttatggcgaggcggcggcggcgg cggccctataaaaagcgaagcgcgcggcgggcgggagtcgctgcgcgctgccttcgcccgtgcccgctccgccgccgcctc gcgccgccgccccggctctgactgaccgcgttactcccacaggtgagcgggcgggacggccttctcctccgggctgtaatt agcgcttggtttaatgacggcttgtttcttttctgtggctgcgtgaaagccttgaggggctccgggagggcccttgtgcggg gggagcggctcggggggtcgtgcgtgtgtgtgtgcgtggggagcgccgcgtgcggctccgcgctgcccggcggctgtgagcg ctgcgggcgcggcgcggggctttgtgcgctccgcagtgtgcgcgaggggagcgcggccggggcggtgccccgcggtgcgggg ggggctgcgaggggaacaaaggctgcgtgcggggtgtgtgcgtggggggggtgagcagggggtgtgggcgcgtcggtcggctg caaccccccctgcaccccctccccgagttgctgagcacggcccggcttcgggtgcggggctccgtacggggcgtggcgcggg gctcgccgtgccggcggggggtggcggcaggtgggggtgccggcggggcggggccgcctcgggccggggagggctcggggg agggggcgcggcggccccggagcgccggcggctgtcgaggcgcggcgagccgcagccattgcctttatggtaatcgtgcgag agggcgcagggacttcctttgtcccaaatctgtgcggagccgaaatctggaggcgccgccgcaccccctctagcgggcgcgg ggcgaagcggtgcggcgccggcaggaaggaaatgggcgggagggccttcgtgcgtcgccgccgcgctccccttctccctc tccagcctcggggctgtccgcggggggacggctgccttcgggggggacggggcagggcggggttcggcttctggcgtgtgacc ggcggctctagagcctctgctaaccatgttcatgccttcttcttttttcctacagctcctgggcaacgtgctggttattgtgct gtctcatcattttggcaaagaattcttcgaaagatctgctagcttaattaacccggtcgccaccatggtgagcaagggcgagg agctgttcaccggggtggtgcccatcctggtcgagctggacggcgacgtaaacggccacaagttcagcgtgtccggcgagggc gagggcgatgccacctacggcaagctgaccctgaagttcatctgcaccaccggcaagctgcccgtgccctggcccaccctcgt gaccaccctgacctacggcgtgcagtgcttcagccgctaccccgaccacatgaagcagcacgacttcttcaagtccgccatgc ccgaaggctacgtccaggagcgcaccatcttcttcaaggacgacggcaactacaagacccgcgccgaggtgaagttcgagggc gacacccctggtgaaccgcatcgagctgaagggcatcgacttcaaggaggacggcaacatcctggggcacaagctggagtacaa ctacaacagccacaacgtctatatcatggccgacaagcagaagaacggcatcaaggtgaacttcaagatccgccacaacatcg aggacggcagcgtgcagctcgccgaccactaccagcagaacacccccatcggcgacggccccgtgctgctgcccgacaaccac tacctgagcacccagtccgccctgagcaaagaccccaacgagaagcgcgatcacatggtcctgctggagttcgtgaccgccgc cgggatcactctcggcatggacgagctgtaccctggaggcttgctgaaggctgtatgctgttagacaatgattcacacggtgt tttggccactgactgacaccgtgtgtcattgtctaacaggacacaaggcctgttactagcactcacatggaacaaatggccat gcatctagagggccctattctatagtgtcacctaaatgctagagctcgctgatcagcctcgactgtgccttctagttgccagc catctgttgtttgcccctcccccgtgccttccttgaccctggaaggtgccactcccactgtcctttcctaataaaatgaggaa attgcatcgcattgtctgagtaggtgtcattctattctggggggtgggtggggcaggacagcaaggggggaggattgggaaga caatagcaggcatgctggggagctagagtcgaccggaccggtggaagtcctcttcctcggtgtccttgacttcaaagggtctc tcccatttgcctggagagaggggaaggtgggcatcaccagggggtgagtgaaggtttggaagagtgtagcagaataagaaacca tgagtcccctccctgagaagccctgagccccttgacgacacacatccctcgaggctcagcttcatcatctgtaaaaggtgct gaaactgaccatccaagctgccgaaaaagattgtgtgggataattcaaaactagaggaagatgcagaatttctacatcgtgg cgatgtcaggctaagagatgccatcgtggctgtgcattttattggaatcatatgtttatttgagggtgtcttggatattaca aataaaatgttggagcatcaggcatatttggtaccttctgtctaaggctccctgcccctttgttaattggcagctcagttattc atccagggcaaacattctgcttactattcctgagagctttcctcatcctctagattggcaggggaaatgcagatgcctgagca gcctcccctctgccataccaacagagcttcaccatcgaggcatgcagagtggacaggggcctcagggacccctgatcccagct ttctcattggacagaaggaggagactgggggctggagagggacctgggcccccactaaggccacagcagagccaggactttagc tgtgctgactgcagcctggcttgcctccactgccctcctttgcctcaagagcaagggagcctcagagtggaggaagcagcccc tggccttgcctcccacctccctccctatgctgttttcctgggacagtgggagctggcttagaatgccctggggcccccagg accctggcatttaacccctcaggggcaggaaggcagcctgagatacagaagagtccatcacctgctgtatgccacacaccat
``` cccacagttacgtactagttcgaagccacgcgtccgaagggcgaattgtagataagtagcatggcgggttaatcattaacta caaggaaccccctagtgatggagttggccactccctctctgcgcgctcgctcgctcactgaggccgggcgaccaaaggtcgccc gacgcccgggctttgcccgggcggcctcagtgagcgagcgagcgcgcagagagggagtggccaa miRNA scaffold DNA sequence
(SEQ ID NO: 14)
ctggaggcttgctgaaggctgtatgctgttagacaatgattcacacggtgttttggccactgactgacaccgtgt gtcattgtctaacaggacacaaggcctgttactagcactcacatggaacaaatggcc 170XAL1 guide (antisense)
(SEQ ID NO: 15)
UCGACAAUGAUUCACACGGU 170XAL1 non-guide
(SEQ ID NO: 16)
ACCGUGUGUCAUUGUCGAA.

170XAL2 guide (antisense)
(SEQ ID NO: 17)
UAGACGAUGAUUCACACGGU

170XAL1 non-guide
(SEQ ID NO: 18)
ACCGUGUGUCAUCGUCUAA

170XA
(SEQ ID NO: 19)
TAGACAATGATTCACACGGTGTTTTGGCCACTGACTGACACCGTGTGTCATTGTCTAA

---

What is claimed is:

1. An RNAi comprising a first strand comprising a guide region which comprises the sequence 5'-UAGACAAUGAUUCACACGGU-3' (SEQ ID NO:1) or a sequence having about 90% identity to SEQ ID NO:1, and a second strand comprising a non-guide region which comprises the sequence 5'-ACCGUGUGUCAUUGUCUAA-3' (SEQ ID NO:2) or a sequence having about 90% identity to SEQ ID NO:2, wherein the first strand and second strand form a duplex and wherein the A residue at residue 18 or residue 19 of the second strand forms a bulge in the non-guide region.

2. The RNAi of claim 1, wherein the guide region comprises the nucleic acid sequence of SEQ ID NO:1.

3. The RNAi of claim 1, wherein the non-guide region comprises the nucleic acid sequence of SEQ ID NO:2.

4. The RNAi of claim 1, wherein the sequence is improved to reduce off-target gene silencing.

5. The RNAi of claim 1, wherein sequence comprises one or more CpG motifs.

6. The RNAi of claim 1, wherein the sequence comprises one or more CpG motifs in a seed region.

7. The RNAi of claim 1, wherein the RNAi comprises a first strand comprising a guide region which comprises the sequence 5'-UCGACAAUGAUUCACACGGU-3' (SEQ ID NO:15) and a second strand comprising a non-guide region which comprises the sequence 5'-ACCGUGUGUCAUUGUCGAA-3' (SEQ ID NO:16), wherein the first strand and second strand form a duplex and wherein the A residue at residue 18 or residue 19 of the second strand forms a bulge in the non-guide region.

8. The RNAi of claim 1, wherein the RNAi comprises a first strand comprising a guide region which comprises the sequence 5'-UAGACGAUGAUUCACACGGU-3' (SEQ ID NO:17) and a second strand comprising a non-guide region which comprises the sequence 5'-ACCGUGUGUCAUCGUCUAA-3' (SEQ ID NO:18), wherein the first strand and second strand form a duplex and wherein the A residue at residue 18 or residue 19 of the second strand forms a bulge in the non-guide region.

9. The RNAi of claim 1, wherein the guide region comprises the nucleic acid sequence of SEQ ID NO:15 and the non-guide region comprises the nucleic acid sequence of SEQ ID NO:16, or the nucleic acid sequence of SEQ ID NO:17 and the non-guide region comprises the nucleic acid sequence of SEQ ID NO:18.

10. The RNAi of claim 1, wherein U residues at residues 11 and 12 of the guide region forms a bulge in the guide region.

11. The RNAi of claim 1, wherein the duplex is between 19 and 25 or 19 and 23 base pairs in length.

12. The RNAi of claim 1, wherein the first and/or second strand further comprises a 3' overhang region, a 5' overhang region, or both 3' and 5' overhang regions.

13. The RNAi of claim 1, wherein the first strand and the second strand are linked by means of a RNA linker capable of forming a loop structure.

14. The RNAi of claim 13, wherein RNA linker capable of forming a loop structure comprises from 4 to 50 nucleotides.

15. The RNAi of claim 13, wherein the RNA linker capable of forming a loop structure comprises from 4 to 20 nucleotides, or the RNAi linker capable of forming a loop structure comprises 13 nucleotides.

16. The RNAi of claim 1, wherein the second strand of the RNAi comprises the nucleotide sequence of SEQ ID NO:3 or a nucleotide sequence about 90% identical to the nucleotide sequence of SEQ ID NO:3.

17. The RNAi of claim 1, wherein the RNAi is a small inhibitory RNA (siRNA), a microRNA (miRNA), or a small hairpin RNA (shRNA).

18. An expression construct comprising nucleic acid encoding the RNAi of claim 1.

19. The expression construct of claim 18 wherein the nucleic acid encoding the RNAi comprises a miRNA scaffold.

20. The expression construct of claim 19 wherein the nucleic acid encoding the RNAi comprises a miR-155 scaffold.

21. A vector comprising the expression construct of claim 18.

22. The vector of claim 21, wherein the vector is a recombinant adeno-associated virus (rAAV) vector, a recombinant adenoviral vector, a recombinant lentiviral vector or a recombinant herpes simplex virus (HSV) vector.

23. The vector of claim 22, wherein the vector is a recombinant AAV (rAAV) vector.

24. The rAAV vector of claim 23, wherein the expression construct is flanked by one or more AAV inverted terminal repeat (ITR) sequences.

25. The rAAV vector of claim 23, wherein the AAV ITRs are AAV2 ITRs.

26. The rAAV vector of claim 25, wherein the rAAV vector comprises 5' to 3' an AAV2 ITR, a promoter, nucleic acid encoding the RNAi, a polyadenylation signal, and an AAV2 ITR.

27. The rAAV vector of claim 26, wherein the rAAV vector comprises 5' to 3' an AAV2 ITR, the CBA promoter, nucleic acid encoding the RNAi, a bovine growth hormone polyadenylation signal, and an AAV2 ITR.

28. The rAAV vector of claim 27, wherein the vector further comprise a stuffer nucleic acid.

29. The rAAV vector of claim 27, wherein the stuffer nucleic acid comprises nucleic acid encoding a green fluorescent protein (GFP).

30. The rAAV vector of claim 23, wherein the vector is a self-complementary vector.

31. A cell comprising the vector of claim 21.

32. The cell of claim 31, wherein the cell is a central nervous system (CNS) cell.

33. A viral particle comprising the vector of claim 22, wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector.

34. A recombinant AAV particle comprising the rAAV vector of claim 23.

35. The rAAV particle of claim 34, wherein the expression construct is flanked by one or more AAV inverted terminal repeat (ITR) sequences, wherein the ITR and the capsid of the rAAV viral particle are derived from the same AAV serotype.

36. The rAAV particle of claim 34, wherein the expression construct is flanked by one or more AAV inverted terminal repeat (ITR) sequences, wherein the ITR and the capsid of the rAAV viral particles are derived from different AAV serotypes.

37. The rAAV particle of claim 34, wherein the rAAV viral particle comprises AAV2 capsid.

38. The rAAV particle of claim 37, wherein the rAAV viral particle comprises an AAV1 capsid, and wherein the vector comprises AAV2 ITRs.

39. A composition comprising the viral particle of claim 33.

40. The composition of claim 39 further comprises a pharmaceutically acceptable carrier.

41. A kit for inducing RNA interference in a mammal with Huntington's disease comprising the RNAi of claim 1.

* * * * *

SEQUENCE LISTING

<160> NUMBER OF SEQ ID NOS: 26

<210> SEQ ID NO 1
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1
uagacaauga uucacacggu                                                    20

<210> SEQ ID NO 2
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2
accguguguc auugucuaa                                                     19

<210> SEQ ID NO 3
<211> LENGTH: 21
<212> TYPE: RNA
<213> ORGANISM: Artificial Sequence
<220> FEATURE:
<223> OTHER INFORMATION: Synthetic Construct

<400> SEQUENCE: 3
accgugugaa ucauugucua a                                                  21

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tagacaatga ttcacacggt                                                  20

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
accgtgtgtc attgtctaa                                                   19

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
accgtgtgaa tcattgtcut aa                                               22

<210> SEQ ID NO 7
<211> LENGTH: 65
<212> TYPE: RNA
<213> ORGANISM: Artificial Sequence
<220> FEATURE:
<223> OTHER INFORMATION: Synthetic Construct

<400> SEQUENCE: 7
ugcuguagac aaugauucac acgguguuuu ggccacugac ugacaccgug ucauugucua      60
acagg                                                                  65

<210> SEQ ID NO 8
<211> LENGTH: 65
<212> TYPE: DNA
<213> ORGANISM: Artificial Sequence
<220> FEATURE:
<223> OTHER INFORMATION: Synthetic Construct

<400> SEQUENCE: 8
tgctgtagac aatgattcac acggtgtttt ggccactgac tgacaccgtg tcattgtcta      60
acagg                                                                  65

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ctccgtccgg tagacatgct                                                  20

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

```
<400> SEQUENCE: 10
ggaaatcaga accctcaaat gg                                             22

<210> SEQ ID NO 11
<211> LENGTH: 29
<212> TYPE: DNA
<213> ORGANISM: Artificial Sequence
<220> FEATURE:
<223> OTHER INFORMATION: Synthetic Construct

<400> SEQUENCE: 11
tgagcactgt tcaactgtgt gtatcggga                                      29

<210> SEQ ID NO 12
<211> LENGTH: 78
<212> TYPE: DNA
<213> ORGANISM: Artificial Sequence
<220> FEATURE:
<223> OTHER INFORMATION: Synthetic Construct

<400> SEQUENCE: 12
cactccctct ctgcgcgctc gctcgctcac tgaggccggg cgaccaaagg tcgcccacgc    60
ccgggctttg cccgggcg                                                  78

<210> SEQ ID NO 13
<211> LENGTH: 4297
<212> TYPE: DNA
<213> ORGANISM: Artificial Sequence
<220> FEATURE:
<223> OTHER INFORMATION: Synthetic Construct

<400> SEQUENCE: 13
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg    120
gccaactcca tcactagggg ttcctggagg ggtggagtcg tgacaattcg cccttgggcc    180
taggcaattg gatcccggac cgtcgacatt gattattgac tagttattaa tagtaatcaa    240
ttacggggtc attagttcat agcccatata tggagttccg cgttacataa cttacggtaa    300
atggcccgcc tggctgaccg cccaacgacc cccgcccatt gacgtcaata atgacgtatg    360
ttcccatagt aacgccaata gggactttcc attgacgtca atgggtggag tatttacggt    420
aaactgccca cttggcagta catcaagtgt atcatatgcc aagtacgccc cctattgacg    480
tcaatgacgg taaatggccc gcctggcatt atgcccagta catgacctta tgggactttc    540
ctacttggca gtacatctac gtattagtca tcgctattac catggtcgag gtgagcccca    600
cgttctgctt cactctcccc atctccccc cctccccacc cccaattttg tatttattta    660
ttttttaatt attttgtgca gcgatggggg cggggggggg ggggggcgc gcgccaggcg    720 gggcggggcg gggcgagggg cgggcgggg cgaggcggag aggtgcggcg gcagccaatc    780
agagcggcgc gctccgaaag tttccttttta tggcgaggcg gcggcggcgg cggccctata    840
aaaagcgaag cgcgcggcgg gcgggagtcg ctgcgcgctg ccttcgcccc gtgccccgct    900
ccgccgccgc ctcgcgccgc ccgccccggc tctgactgac cgcgttactc ccacaggtga    960
gcgggcggga cggcccttct cctccgggct gtaattagcg cttggtttaa tgacggcttg    1020
tttcttttct gtggctgcgt gaaagccttg aggggctccg ggagggccct ttgtgcgggg    1080
ggagcggctc ggggggtgcg tgcgtgtgtg tgtgcgtggg gagcgccgcg tgcggctccg    1140
cgctgcccgg cggctgtgag cgctgcgggc gcggcgcggg gctttgtgcg ctccgcagtg    1200
```

```
tgcgcgaggg gagcgcggcc gggggcggtg ccccgcggtg cggggggggc tgcgagggga    1260
acaaaggctg cgtgcggggt gtgtgcgtgg ggggtgagc aggggggtgtg ggcgcgtcgg    1320 tcgggctgca accccccctg caccccccctc cccgagttgc tgagcacggc ccggcttcgg    1380
gtgcggggct ccgtacgggg cgtggcgcgg ggctcgccgt gccgggcggg gggtggcggc    1440
aggtgggggt gccgggcggg gcggggccgc ctcgggccgg ggagggctcg ggggaggggc    1500
gcggcggccc ccggagcgcc ggcggctgtc gaggcgcggc gagccgcagc cattgccttt    1560
tatggtaatc gtgcgagagg gcgcaggac ttcctttgtc ccaaatctgt gcggagccga    1620
aatctgggag gcgccgccgc accccctcta gcgggcgcgg ggcgaagcgg tgcggcgccg    1680
gcaggaagga aatgggcggg gagggccttc gtgcgtcgcc gcgccgccgt ccccttctcc    1740
ctctccagcc tcgggctgt ccgcgggggg acggctgcct tcgggggga cggggcaggg    1800 cggggttcgg cttctggcgt gtgaccggcg gctctagagc ctctgctaac catgttcatg    1860
ccttcttctt tttcctacag ctcctgggca acgtgctggt tattgtgctg tctcatcatt    1920
ttggcaaaga attcttcgaa agatctgcta gcttaattaa cccggtcgcc accatggtga    1980
gcaagggcga ggagctgttc accggggtgg tgcccatcct ggtcgagctg gacggcgacg    2040
taaacggcca caagttcagc gtgtccggcg agggcgaggg cgatgccacc tacggcaagc    2100
tgaccctgaa gttcatctgc accaccggca agctgcccgt gccctggccc accctcgtga    2160
ccaccctgac ctacggcgtg cagtgcttca gccgctaccc cgaccacatg aagcagcacg    2220
acttcttcaa gtccgccatg cccgaaggct acgtccagga gcgcaccatc ttcttcaagg    2280
acgacggcaa ctacaagacc cgcgccgagg tgaagttcga gggcgacacc ctggtgaacc    2340
gcatcgagct gaagggcatc gacttcaagg aggacggcaa catcctgggg cacaagctgg    2400
agtacaacta caacagccac aacgtctata tcatggccga caagcagaag aacggcatca    2460
aggtgaactt caagatccgc cacaacatcg aggacggcag cgtgcagctc gccgaccact    2520
accagcagaa cacccccatc ggcgacggcc ccgtgctgct gcccgacaac cactacctga    2580
gcacccagtc cgccctgagc aaagacccca acgagaagcg cgatcacatg gtcctgctgg    2640
agttcgtgac cgccgccggg atcactctcg gcatggacga gctgtaccct ggaggcttgc    2700
tgaaggctgt atgctgttag acaatgattc acacggtgtt ttggccactg actgacaccg    2760
tgtgtcattg tctaacagga cacaaggcct gttactagca ctcacatgga acaaatggcc    2820
atgcatctag agggccctat tctatagtgt cacctaaatg ctagagctcg ctgatcagcc    2880
tcgactgtgc cttctagttg ccagccatct gttgtttgcc cctcccccgt gccttccttg    2940
accctggaag gtgccactcc cactgtcctt tcctaataaa atgaggaaat tgcatcgcat    3000
tgtctgagta ggtgtcattc tattctgggg gtgggtgg ggcaggacag caaggggag    3060 gattgggaag acaatagcag gcatgctggg gagctagagt cgaccggacc ggtggaagtc    3120
ctcttcctcg gtgtccttga cttcaaaggg tctctcccat ttgcctggag agaggggaag    3180
gtgggcatca ccagggtga gtgaaggttt ggaagagtgt agcagaataa gaaaccatga    3240 gtccctccc tgagaagccc tgagcccccct tgacgacaca catccctcga ggctcagctt    3300
catcatctgt aaaaggtgct gaaactgacc atccaagctg ccgaaaaaga ttgtgtgggg    3360
ataattcaaa actagaggaa gatgcagaat ttctacatcg tggcgatgtc aggctaagag    3420
atgccatcgt ggctgtgcat ttttattgga atcatatgtt tatttgaggg tgtcttggat    3480
attacaaata aaatgttgga gcatcaggca tatttggtac cttctgtcta aggctccctg    3540
```

```
ccccttgtta attggcagct cagttattca tccagggcaa acattctgct tactattcct    3600
gagagctttc ctcatcctct agattggcag gggaaatgca gatgcctgag cagcctcccc    3660
tctgccatac caacagagct tcaccatcga ggcatgcaga gtggacaggg gcctcaggga    3720
cccctgatcc cagctttctc attggacaga aggaggagac tggggctgga gagggacctg    3780
ggcccccact aaggccacag cagagccagg actttagctg tgctgactgc agcctggctt    3840
gcctccactg ccctcctttg cctcaagagc aagggagcct cagagtggag gaagcagccc    3900
ctggccttgc ctcccacctc ccctccccta tgctgttttc ctgggacagt gggagctggc    3960
ttagaatgcc ctggggcccc caggaccctg gcattttaac ccctcagggg caggaaggca    4020
gcctgagata cagaagagtc catcacctgc tgtatgccac acaccatccc cacagttacg    4080
tactagttcg aagccacgcg tccgaagggc gaattgtaga taagtagcat ggcgggttaa    4140
tcattaacta caaggaaccc ctagtgatgg agttggccac tccctctctg cgcgctcgct    4200
cgctcactga ggccgggcga ccaaaggtcg cccgacgccc gggctttgcc cgggcggcct    4260
cagtgagcga gcgagcgcgc agagagggag tggccaa                             4297
```

<210> SEQ ID NO 14
<211> LENGTH: 132
<212> TYPE: DNA
<213> ORGANISM: Artificial Sequence
<220> FEATURE:
<223> OTHER INFORMATION: Synthetic Construct

<400> SEQUENCE: 14

```
ctggaggctt gctgaaggct gtatgctgtt agacaatgat tcacacggtg ttttggccac     60
tgactgacac cgtgtgtcat tgtctaacag gacacaaggc ctgttactag cactcacatg    120
gaacaaatgg cc                                                        132
```

<210> SEQ ID NO 15
<211> LENGTH: 20
<212> TYPE: RNA
<213> ORGANISM: Artificial Sequence
<220> FEATURE:
<223> OTHER INFORMATION: Synthetic Construct

<400> SEQUENCE: 15

```
ucgacaauga uucacacggu                                                 20
```

<210> SEQ ID NO 16
<211> LENGTH: 19
<212> TYPE: RNA
<213> ORGANISM: Artificial Sequence
<220> FEATURE:
<223> OTHER INFORMATION: Synthetic Construct

<400> SEQUENCE: 16

```
accguguguc auugucgaa                                                  19
```

<210> SEQ ID NO 17
<211> LENGTH: 20
<212> TYPE: RNA
<213> ORGANISM: Artificial Sequence
<220> FEATURE:
<223> OTHER INFORMATION: Synthetic Construct

<400> SEQUENCE: 17

```
uagacgauga uucacacggu                                                 20
```

```
<210> SEQ ID NO 18
<211> LENGTH: 19
<212> TYPE: RNA
<213> ORGANISM: Artificial Sequence
<220> FEATURE:
<223> OTHER INFORMATION: Synthetic Construct

<400> SEQUENCE: 18
accguguguc aucgucuaa                                                19

<210> SEQ ID NO 19
<211> LENGTH: 58
<212> TYPE: DNA
<213> ORGANISM: Artificial Sequence
<220> FEATURE:
<223> OTHER INFORMATION: Synthetic Construct

<400> SEQUENCE: 19
tagacaatga ttcacacggt gttttggcca ctgactgaca ccgtgtgtca ttgtctaa     58

<210> SEQ ID NO 20
<211> LENGTH: 63
<212> TYPE: DNA
<213> ORGANISM: Artificial Sequence
<220> FEATURE:
<223> OTHER INFORMATION: Synthetic Construct

<400> SEQUENCE: 20
tgctgtagac aatgattcac acggtgtttt ggccactgac tgacaccgtg tgtcattgtc   60
taa                                                                 63

<210> SEQ ID NO 21
<211> LENGTH: 63
<212> TYPE: DNA
<213> ORGANISM: Artificial Sequence
<220> FEATURE:
<223> OTHER INFORMATION: Synthetic Construct

<400> SEQUENCE: 21
tgctgtcgac aatgattcac acggtgtttt ggccactgac tgacaccgtg tgtcattgtc   60
gaa                                                                 63

<210> SEQ ID NO 22
<211> LENGTH: 63
<212> TYPE: DNA
<213> ORGANISM: Artificial Sequence
<220> FEATURE:
<223> OTHER INFORMATION: Synthetic Construct

<400> SEQUENCE: 22
tgctgtagac gatgattcac acggtgtttt ggccactgac tgacaccgtg tgtcatcgtc   60
taa                                                                 63

<210> SEQ ID NO 23
<211> LENGTH: 66
<212> TYPE: RNA
<213> ORGANISM: Artificial Sequence
<220> FEATURE:
<223> OTHER INFORMATION: Synthetic Construct

<400> SEQUENCE: 23
ugcuguagac aaugauucac acgguguuuu ggccacugac ugacaccgug ugucauuguc   60
uacagg                                                              66
```

```
<210> SEQ ID NO 24
<211> LENGTH: 67
<212> TYPE: RNA
<213> ORGANISM: Artificial Sequence
<220> FEATURE:
<223> OTHER INFORMATION: Synthetic Construct

<400> SEQUENCE: 24
ugcuguagac aaugauucac acgguguuuu ggccacugac ugacaccgug ugucauuguc      60
uaacagg                                                               67

<210> SEQ ID NO 25
<211> LENGTH: 58
<212> TYPE: DNA
<213> ORGANISM: Artificial Sequence
<220> FEATURE:
<223> OTHER INFORMATION: Synthetic Construct

<400> SEQUENCE: 25
tcgacaatga ttcacacggt gttttggcca ctgactgaca ccgtgtgtca ttgtcgaa       58

<210> SEQ ID NO 26
<211> LENGTH: 58
<212> TYPE: DNA
<213> ORGANISM: Artificial Sequence
<220> FEATURE:
<223> OTHER INFORMATION: Synthetic Construct

<400> SEQUENCE: 26
tagacgatga ttcacacggt gttttggcca ctgactgaca ccgtgtgtca tcgtctaa       58
```